(12) United States Patent
Kramps et al.

(10) Patent No.: US 11,965,000 B2
(45) Date of Patent: Apr. 23, 2024

(54) RESPIRATORY SYNCYTIAL VIRUS (RSV) VACCINE

(71) Applicant: CureVac SE, Tübingen (DE)

(72) Inventors: Thomas Kramps, Tübingen (DE); Margit Schnee, Tübingen (DE); Daniel Voss, Tübingen (DE); Benjamin Petsch, Tübingen (DE)

(73) Assignee: CureVac SE, Tübingen (DE)

( * ) Notice: Subject to any disclaimer, the term of this patent is extended or adjusted under 35 U.S.C. 154(b) by 0 days.

(21) Appl. No.: 18/463,276

(22) Filed: Sep. 7, 2023

(65) Prior Publication Data

US 2024/0002449 A1 Jan. 4, 2024

Related U.S. Application Data

(60) Continuation of application No. 18/348,042, filed on Jul. 6, 2023, which is a division of application No. 17/316,834, filed on May 11, 2021, now Pat. No. 11,739,125, which is a continuation of application No. 16/168,747, filed on Oct. 23, 2018, now Pat. No. 11,034,729, which is a continuation of application No. 15/488,815, filed on Apr. 17, 2017, now Pat. No. 10,150,797, which is a continuation of application No. 15/048,439, filed on Feb. 19, 2016, now Pat. No. 9,688,729, which is a continuation of application No. PCT/EP2014/002301, filed on Aug. 21, 2014.

(51) Int. Cl.
| | |
|---|---|
| *C07K 14/005* | (2006.01) |
| *A61K 39/12* | (2006.01) |
| *A61K 39/155* | (2006.01) |
| *C07K 16/10* | (2006.01) |
| *C12N 7/00* | (2006.01) |
| *A61K 39/00* | (2006.01) |
| *A61K 48/00* | (2006.01) |

(52) U.S. Cl.
CPC ............ *C07K 14/005* (2013.01); *A61K 39/12* (2013.01); *A61K 39/155* (2013.01); *C07K 16/1027* (2013.01); *C12N 7/00* (2013.01); *A61K 2039/505* (2013.01); *A61K 2039/53* (2013.01); *A61K 2039/6031* (2013.01); *A61K 48/00* (2013.01); *C07K 2317/24* (2013.01); *C12N 2760/18534* (2013.01)

(58) Field of Classification Search
None
See application file for complete search history.

(56) References Cited

U.S. PATENT DOCUMENTS

| | | |
|---|---|---|
| 3,906,092 A | 9/1975 | Hilleman et al. |
| 4,373,071 A | 2/1983 | Itakura |
| 4,401,796 A | 8/1983 | Itakura |
| 4,415,732 A | 11/1983 | Caruthers et al. |
| 4,578,399 A | 3/1986 | Schorlemmer et al. |
| 5,516,652 A | 5/1996 | Abramovitz et al. |
| 5,663,153 A | 9/1997 | Hutcherson et al. |
| 5,663,163 A | 9/1997 | Takaya et al. |
| 5,844,075 A | 12/1998 | Kawakami et al. |
| 5,965,720 A | 10/1999 | Gryaznov et al. |
| 6,096,307 A | 8/2000 | Braswell et al. |
| 6,218,371 B1 | 4/2001 | Krieg et al. |
| 6,239,116 B1 | 5/2001 | Krieg et al. |
| 6,322,967 B1 | 11/2001 | Parkin |
| 6,406,705 B1 | 6/2002 | Davis et al. |
| 6,498,148 B1 | 12/2002 | Raz |
| 6,514,948 B1 | 2/2003 | Raz et al. |
| 6,552,006 B2 | 4/2003 | Raz et al. |
| 6,589,940 B1 | 7/2003 | Raz et al. |
| 6,610,661 B1 | 8/2003 | Carson et al. |
| 6,689,757 B1 | 2/2004 | Craig |
| 6,716,434 B1 | 4/2004 | Ansley et al. |
| 7,001,890 B1 | 2/2006 | Wagner et al. |

(Continued)

FOREIGN PATENT DOCUMENTS

| | | |
|---|---|---|
| AU | 776268 | 12/2000 |
| DE | 102004035227 | 2/2002 |

(Continued)

OTHER PUBLICATIONS

"Cell-penetrating peptide," *Wikipedia*, located at http://en.wikipedia.org/wiki/Cell-penetrating_peptide, downloaded Dec. 11, 2012.
"DOC/Alum Complex," Violin: Vaccine investigation and online information network, located at http://www.violinet.org/vaxjo/vaxjo_detail.php?c_vaxjo_id=49, downloaded on Aug. 28, 2012.
"QS21," Wikipedia, located at http://en.wikipedia.org/wiki/QS21, downloaded on Dec. 11, 2012.
"Ribi vaccine adjuvant," Violin: Vaccine investigation and online information network, located at http://www.violinet.org/vaxjo/vaxjo_detail.php?c_vaxjo_id=21, downloaded on Dec. 17, 2012.

(Continued)

*Primary Examiner* — Agnieszka Boesen
(74) *Attorney, Agent, or Firm* — Parker Highlander PLLC

(57) ABSTRACT

The present invention relates to an mRNA sequence, comprising a coding region, encoding at least one antigenic peptide or protein of RSV infections Respiratory syncytial virus (RSV) or a fragment, variant or derivative thereof. Additionally the present invention relates to a composition comprising a plurality of mRNA sequences comprising a coding region, encoding at least one antigenic peptide or protein of RSV infections Respiratory syncytial virus (RSV) or a fragment, variant or derivative thereof. Furthermore it also discloses the use of the mRNA sequence or the composition comprising a plurality of mRNA sequences for the preparation of a pharmaceutical composition, especially a vaccine, e.g. for use in the prophylaxis or treatment of RSV infections Respiratory syncytial virus (RSV) infections. The present invention further describes a method of treatment or prophylaxis of RSV infections using the mRNA sequence.

30 Claims, 23 Drawing Sheets
Specification includes a Sequence Listing.

(56) References Cited

U.S. PATENT DOCUMENTS

| | | | |
|---|---|---|---|
| 7,208,478 B2 | 4/2007 | Carson et al. |
| 7,407,944 B2 | 8/2008 | Agrawal et al. |
| 7,470,674 B2 | 12/2008 | Agrawal et al. |
| 7,517,862 B2 | 4/2009 | Agrawal et al. |
| 7,709,007 B2 | 5/2010 | Murphy et al. |
| 8,206,990 B2 | 6/2012 | Ritt et al. |
| 8,217,016 B2 | 7/2012 | Hoerr et al. |
| 8,383,340 B2 | 2/2013 | Ketterer et al. |
| 8,460,941 B2 | 6/2013 | Ritt et al. |
| 8,703,906 B2 | 4/2014 | Baumhof et al. |
| 8,771,728 B2 | 7/2014 | Huang et al. |
| 8,852,472 B2 | 10/2014 | Keil et al. |
| 8,968,746 B2 | 3/2015 | Baumhof et al. |
| 8,969,543 B2 | 3/2015 | Jeong et al. |
| 9,155,788 B2 | 10/2015 | Hoerr et al. |
| 9,226,959 B2 | 1/2016 | Kramps et al. |
| 9,234,013 B2 | 1/2016 | Thess et al. |
| 9,314,535 B2 | 4/2016 | Baumhof et al. |
| 9,352,028 B2 | 5/2016 | Barner et al. |
| 9,402,887 B2 | 8/2016 | Probst et al. |
| 9,421,255 B2 | 8/2016 | Baumhof et al. |
| 9,433,669 B2 | 9/2016 | Hoerr et al. |
| 9,433,670 B2 | 9/2016 | Hoerr et al. |
| 9,439,956 B2 | 9/2016 | Hoerr et al. |
| 9,447,431 B2 | 9/2016 | Thess et al. |
| 9,463,228 B2 | 10/2016 | Hoerr et al. |
| 9,572,874 B2 | 2/2017 | Fotin-Mleczek et al. |
| 9,616,084 B2 | 4/2017 | Mutzke |
| 9,623,095 B2 | 4/2017 | Kallen et al. |
| 9,629,812 B2 | 4/2017 | Medarova et al. |
| 9,655,955 B2 | 5/2017 | Hoerr et al. |
| 9,669,089 B2 | 6/2017 | Thess et al. |
| 9,683,233 B2 | 6/2017 | Thess |
| 9,687,262 B2 | 6/2017 | Rousseau et al. |
| 9,688,729 B2 * | 6/2017 | Kramps ............... A61P 37/04 |
| 9,737,595 B2 | 8/2017 | Lorenz et al. |
| 9,839,697 B2 | 12/2017 | Thess et al. |
| 9,890,391 B2 | 2/2018 | Thess et al. |
| 9,907,862 B2 | 3/2018 | Baumhof et al. |
| 9,974,845 B2 | 5/2018 | Fotin-Mleczek et al. |
| 10,010,592 B2 | 7/2018 | Thess et al. |
| 10,017,826 B2 | 7/2018 | von der Mülbe et al. |
| 10,047,375 B2 | 8/2018 | Thess |
| 10,080,809 B2 | 9/2018 | Thess |
| 10,111,967 B2 | 10/2018 | Fotin-Mleczek et al. |
| 10,111,968 B2 | 10/2018 | Thess et al. |
| 10,117,920 B2 | 11/2018 | Fotin-Mleczek et al. |
| 10,150,797 B2 * | 12/2018 | Kramps ............ C07K 16/1027 |
| 10,166,283 B2 | 1/2019 | Thess et al. |
| 10,172,935 B2 | 1/2019 | Kallen et al. |
| 10,188,748 B2 | 1/2019 | von der Mülbe et al. |
| 10,232,024 B2 | 3/2019 | Thess et al. |
| 10,293,058 B2 | 5/2019 | Fotin-Mleczek et al. |
| 10,293,060 B2 | 5/2019 | Baumhof |
| 10,307,472 B2 | 6/2019 | Fotin-Mleczek et al. |
| 10,369,216 B2 | 8/2019 | Fotin-Mleczek et al. |
| 10,434,154 B2 | 10/2019 | Probst et al. |
| 10,434,158 B2 | 10/2019 | Fotin-Mleczek et al. |
| 10,441,653 B2 | 10/2019 | Hoerr et al. |
| 10,501,768 B2 | 12/2019 | Eber et al. |
| 10,517,827 B2 | 12/2019 | Eber et al. |
| 10,568,958 B2 | 2/2020 | Baumhof et al. |
| 10,568,972 B2 | 2/2020 | von der Mülbe et al. |
| 10,588,959 B2 | 3/2020 | Kallen et al. |
| 10,596,252 B2 | 3/2020 | Kallen et al. |
| 10,610,605 B2 | 4/2020 | Thess et al. |
| 10,648,017 B2 | 5/2020 | Wochner |
| 10,653,768 B2 | 5/2020 | Mutzke et al. |
| 10,653,799 B2 | 5/2020 | Thess et al. |
| 10,682,406 B2 | 6/2020 | Thess et al. |
| 10,682,426 B2 | 6/2020 | Schnee et al. |
| 10,711,315 B2 | 7/2020 | von der Mülbe et al. |
| 10,729,654 B2 | 8/2020 | Eber et al. |
| 10,729,761 B2 | 8/2020 | Kallen et al. |
| 10,738,306 B2 | 8/2020 | Thess |
| 10,751,424 B2 | 8/2020 | Baumhof et al. |
| 10,760,070 B2 | 9/2020 | Funkner et al. |
| 10,780,054 B2 | 9/2020 | Ketterer et al. |
| 10,799,577 B2 | 10/2020 | Thess et al. |
| 10,799,602 B2 | 10/2020 | Baumhof |
| 10,837,039 B2 | 11/2020 | Wochner et al. |
| 10,869,935 B2 | 12/2020 | Fotin-Mleczek et al. |
| 10,898,584 B2 | 1/2021 | Schlake et al. |
| 10,898,589 B2 | 1/2021 | Thess et al. |
| 10,912,826 B2 | 2/2021 | Thess et al. |
| 10,918,740 B2 | 2/2021 | Fotin-Mleczek et al. |
| 10,988,754 B2 | 4/2021 | Fotin-Mleczek et al. |
| 11,034,729 B2 * | 6/2021 | Kramps ............... A61P 37/04 |
| 11,078,247 B2 | 8/2021 | Fotin-Mleczek et al. |
| 11,110,156 B2 | 9/2021 | Thess et al. |
| 11,110,157 B2 | 9/2021 | Fotin-Mleczek et al. |
| 11,110,166 B2 | 9/2021 | Fotin-Mleczek et al. |
| 11,135,312 B2 | 10/2021 | von der Mülbe et al. |
| 11,141,474 B2 | 10/2021 | Rauch et al. |
| 11,141,476 B2 | 10/2021 | Rauch |
| 11,149,278 B2 | 10/2021 | Thess et al. |
| 11,179,337 B2 | 11/2021 | Eber et al. |
| 11,225,682 B2 | 1/2022 | Reichert et al. |
| 11,241,493 B2 | 2/2022 | Rauch et al. |
| 11,248,223 B2 | 2/2022 | Yazdan Panah et al. |
| 11,254,951 B2 | 2/2022 | Thess |
| 11,266,735 B2 | 3/2022 | Kallen et al. |
| 11,268,157 B2 | 3/2022 | von der Mülbe et al. |
| 11,274,293 B2 | 3/2022 | Funkner et al. |
| 11,279,923 B2 | 3/2022 | Funkner et al. |
| 11,286,492 B2 | 3/2022 | Thess et al. |
| 11,345,920 B2 | 5/2022 | Thess et al. |
| 11,369,691 B2 | 6/2022 | von der Mülbe et al. |
| 11,369,694 B2 | 6/2022 | Schnee et al. |
| 11,384,375 B2 | 7/2022 | Roos et al. |
| 11,413,346 B2 | 8/2022 | Rauch et al. |
| 11,421,038 B2 | 8/2022 | Hoerr et al. |
| 11,433,027 B2 | 9/2022 | Eber et al. |
| 11,446,250 B2 | 9/2022 | Ketterer et al. |
| 11,458,193 B2 | 10/2022 | Lorenz et al. |
| 11,458,195 B2 | 10/2022 | Fotin-Mleczek et al. |
| 11,464,836 B2 | 10/2022 | Horscroft et al. |
| 11,464,847 B2 | 10/2022 | Jasny et al. |
| 11,471,525 B2 | 10/2022 | Rauch et al. |
| 11,478,552 B2 | 10/2022 | Baumhof et al. |
| 11,491,112 B2 | 11/2022 | Ketterer et al. |
| 11,524,066 B2 | 12/2022 | Jasny et al. |
| 11,525,158 B2 | 12/2022 | Yazdan Panah et al. |
| 11,534,405 B2 | 12/2022 | Eber et al. |
| 11,542,490 B2 | 1/2023 | Horscroft et al. |
| 11,559,570 B2 | 1/2023 | Fotin-Mleczek et al. |
| 11,576,966 B2 | 2/2023 | Rauch et al. |
| 11,596,686 B2 | 3/2023 | Rauch et al. |
| 11,596,699 B2 | 3/2023 | Fotin-Mleczek et al. |
| 11,602,557 B2 | 3/2023 | Petsch et al. |
| 11,608,513 B2 | 3/2023 | Roos et al. |
| 11,661,634 B2 | 5/2023 | von der Mülbe et al. |
| 11,667,910 B2 | 6/2023 | Funkner et al. |
| 11,690,910 B2 | 7/2023 | Baumhof et al. |
| 11,692,002 B2 | 7/2023 | Heinz et al. |
| 11,697,816 B2 | 7/2023 | Grund et al. |
| 11,723,967 B2 | 8/2023 | Petsch et al. |
| 11,739,125 B2 * | 8/2023 | Kramps ............... A61K 39/12 424/211.1 |
| 11,739,335 B2 | 8/2023 | Chevessier-Tünnesen et al. |
| 11,760,992 B2 | 9/2023 | Funkner et al. |
| 11,761,009 B2 | 9/2023 | Thess et al. |
| 11,786,590 B2 | 10/2023 | Rauch et al. |
| 2003/0133942 A1 | 7/2003 | Segal |
| 2003/0225016 A1 | 12/2003 | Fearon et al. |
| 2004/0006010 A1 | 1/2004 | Carson et al. |
| 2004/0006034 A1 | 1/2004 | Raz et al. |
| 2004/0019007 A1 | 1/2004 | Monahan et al. |
| 2004/0047869 A1 | 3/2004 | Garcon et al. |
| 2004/0052763 A1 | 3/2004 | Mond et al. |
| 2005/0032730 A1 | 2/2005 | Von der Mulbe et al. |
| 2005/0037494 A1 | 2/2005 | Hecker et al. |
| 2005/0059624 A1 | 3/2005 | Hoerr et al. |
| 2005/0130918 A1 | 6/2005 | Agrawal et al. |

(56) References Cited

U.S. PATENT DOCUMENTS

| | | |
|---|---|---|
| 2005/0215501 A1 | 9/2005 | Lipford et al. |
| 2005/0250723 A1 | 11/2005 | Hoerr et al. |
| 2006/0142227 A1 | 6/2006 | Lamensdorf et al. |
| 2006/0172966 A1 | 8/2006 | Lipford et al. |
| 2006/0188490 A1 | 8/2006 | Hoerr et al. |
| 2006/0188990 A1 | 8/2006 | Kretschmer et al. |
| 2006/0251623 A1 | 11/2006 | Bachmann et al. |
| 2007/0280929 A1 | 12/2007 | Hoerr et al. |
| 2008/0025944 A1 | 1/2008 | Hoerr et al. |
| 2008/0145375 A1 | 6/2008 | Bembridge et al. |
| 2008/0153166 A1 | 6/2008 | Huang et al. |
| 2008/0171711 A1 | 7/2008 | Hoerr et al. |
| 2008/0248067 A1 | 10/2008 | Frazer et al. |
| 2008/0267873 A1 | 10/2008 | Hoerr et al. |
| 2009/0081157 A1 | 3/2009 | Kornbluth et al. |
| 2009/0111765 A1 | 4/2009 | Harmann et al. |
| 2009/0123467 A1 | 5/2009 | Bedi et al. |
| 2009/0324584 A1 | 12/2009 | Hoerr et al. |
| 2010/0047261 A1 | 2/2010 | Hoerr et al. |
| 2010/0048883 A1 | 2/2010 | Ketterer et al. |
| 2010/0062967 A1 | 3/2010 | Keil et al. |
| 2010/0184953 A1 | 7/2010 | Huang et al. |
| 2010/0189729 A1 | 7/2010 | Hoerr et al. |
| 2010/0203076 A1 | 8/2010 | Fotin-Mleczek et al. |
| 2010/0239608 A1 | 9/2010 | von der Mülbe et al. |
| 2010/0291156 A1 | 11/2010 | Barner et al. |
| 2010/0303851 A1 | 12/2010 | Hoerr et al. |
| 2010/0305196 A1 | 12/2010 | Probst et al. |
| 2011/0053829 A1 | 3/2011 | Baumhof et al. |
| 2011/0077287 A1 | 3/2011 | von der Mülbe et al. |
| 2011/0243897 A1 | 10/2011 | Seymour et al. |
| 2011/0250225 A1 | 10/2011 | Fotin-Mleczek et al. |
| 2011/0269950 A1 | 11/2011 | von der Mülbe et al. |
| 2011/0311472 A1 | 12/2011 | Hoerr et al. |
| 2012/0009221 A1 | 1/2012 | Hoerr et al. |
| 2012/0021043 A1 | 1/2012 | Kramps et al. |
| 2012/0058153 A1 | 3/2012 | Ilyinskii et al. |
| 2012/0213818 A1 | 8/2012 | Hoerr et al. |
| 2012/0219573 A1 | 8/2012 | Baumhof et al. |
| 2012/0258046 A1 | 10/2012 | Mutzke |
| 2012/0258104 A1 | 10/2012 | Echeverri et al. |
| 2013/0121998 A1 | 5/2013 | Hoerr et al. |
| 2013/0129754 A1 | 5/2013 | Thess et al. |
| 2013/0142818 A1 | 6/2013 | Baumhof et al. |
| 2013/0195867 A1 | 8/2013 | Hoerr et al. |
| 2013/0202645 A1 | 8/2013 | Barner et al. |
| 2013/0251742 A1 | 9/2013 | Probst et al. |
| 2013/0259879 A1 | 10/2013 | Baumhof et al. |
| 2013/0273001 A1 | 10/2013 | Hoerr et al. |
| 2013/0280283 A1 | 10/2013 | Lorenz et al. |
| 2013/0281382 A1 | 10/2013 | Huang et al. |
| 2013/0295043 A1 | 11/2013 | Kallen et al. |
| 2013/0336998 A1 | 12/2013 | Kallen et al. |
| 2014/0037660 A1 | 2/2014 | Fotin-Mleczek |
| 2014/0241996 A1 | 8/2014 | Medarova et al. |
| 2014/0294877 A1 | 10/2014 | Baumhof |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 | 4/2015 | Thess et al. |
| 2015/0118183 A1 | 4/2015 | Baumhof |
| 2015/0118264 A1 | 4/2015 | Baumhof et al. |
| 2015/0165006 A1 | 6/2015 | Thess et al. |
| 2015/0184195 A1 | 7/2015 | Thess et al. |
| 2015/0218554 A1 | 8/2015 | Thess |
| 2015/0258214 A1 | 9/2015 | Baumhof et al. |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0317679 A1 | 11/2016 | Baumhof et al. |
| 2016/0326575 A1 | 11/2016 | Von der Mulbe et al. |
| 2016/0331844 A1 | 11/2016 | Fotin-Mleczek et al. |
| 2017/0014496 A1 | 1/2017 | Fotin-Mleczek et al. |
| 2017/0028059 A1 | 2/2017 | Baumhof et al. |
| 2017/0029847 A1 | 2/2017 | Thess |
| 2017/0114378 A1 | 4/2017 | Wochner et al. |
| 2017/0182150 A1 | 6/2017 | Kallen et al. |
| 2017/0239372 A1 | 8/2017 | Baumhof et al. |
| 2017/0252430 A1 | 9/2017 | Fotin-Mleczek et al. |
| 2017/0326225 A1 | 11/2017 | Rauch et al. |
| 2018/0044687 A1 | 2/2018 | Thess et al. |
| 2018/0125952 A1 | 5/2018 | Fotin-Mleczek et al. |
| 2018/0126003 A1 | 5/2018 | Hoerr |
| 2018/0126005 A1 | 5/2018 | Fotin-Mleczek et al. |
| 2018/0142275 A1 | 5/2018 | Roos et al. |
| 2018/0147146 A1 | 5/2018 | Eber et al. |
| 2018/0148727 A1 | 5/2018 | Grund et al. |
| 2018/0201967 A1 | 7/2018 | Eber et al. |
| 2018/0208957 A1 | 7/2018 | Roos et al. |
| 2018/0214537 A1 | 8/2018 | Mutzke et al. |
| 2018/0237786 A1 | 8/2018 | Schlake et al. |
| 2018/0237817 A1 | 8/2018 | Roos et al. |
| 2018/0243219 A1 | 8/2018 | Ketterer et al. |
| 2018/0296663 A1 | 10/2018 | Hipp et al. |
| 2018/0298372 A1 | 10/2018 | Funkner et al. |
| 2018/0312545 A1 | 11/2018 | Baumhof et al. |
| 2018/0371392 A1 | 12/2018 | Mayer et al. |
| 2019/0010485 A1 | 1/2019 | Yazdan Panah et al. |
| 2019/0017100 A1 | 1/2019 | Wochner et al. |
| 2019/0024096 A1 | 1/2019 | Schmid et al. |
| 2019/0040378 A1 | 2/2019 | Fotin-Mleczek et al. |
| 2019/0049414 A1 | 2/2019 | Wochner et al. |
| 2019/0083602 A1 | 3/2019 | Roos et al. |
| 2019/0100784 A1 | 4/2019 | Eber et al. |
| 2019/0125857 A1 | 5/2019 | Rauch et al. |
| 2019/0133950 A1 | 5/2019 | Eber et al. |
| 2019/0160164 A1 | 5/2019 | Rauch et al. |
| 2019/0177714 A1 | 6/2019 | Kunze et al. |
| 2019/0185859 A1 | 6/2019 | Fotin-Mleczek et al. |
| 2019/0194760 A1 | 6/2019 | Koch et al. |
| 2019/0225971 A1 | 7/2019 | Williams |
| 2019/0241633 A1 | 8/2019 | Fotin-Mleczek et al. |
| 2019/0249219 A1 | 8/2019 | Reichert et al. |
| 2019/0336608 A1 | 11/2019 | Baumhof et al. |
| 2019/0336611 A1 | 11/2019 | Baumhof et al. |
| 2019/0343933 A1 | 11/2019 | Horscroft et al. |
| 2019/0343942 A1 | 11/2019 | Fotin-Mleczek et al. |
| 2019/0351044 A1 | 11/2019 | Jasny et al. |
| 2019/0351047 A1 | 11/2019 | Jasny et al. |
| 2019/0351048 A1 | 11/2019 | Rauch |
| 2019/0381180 A1 | 12/2019 | Baumhof et al. |
| 2020/0023076 A1 | 1/2020 | Fotin-Mleczek et al. |
| 2020/0085852 A1 | 3/2020 | Fotin-Mleczek |
| 2020/0085944 A1 | 3/2020 | Heidenreich et al. |
| 2020/0149026 A1 | 5/2020 | Horscroft et al. |
| 2020/0163878 A1 | 5/2020 | Baumhof et al. |
| 2020/0179526 A1 | 6/2020 | Baumhof et al. |
| 2020/0318097 A1 | 10/2020 | Funkner et al. |
| 2020/0392572 A1 | 12/2020 | Yazdan Panah et al. |
| 2021/0030864 A1 | 2/2021 | Petsch et al. |
| 2021/0069315 A1 | 3/2021 | Baumhof et al. |
| 2021/0162037 A1 | 6/2021 | Jasny et al. |
| 2021/0170017 A1 | 6/2021 | Lutz et al. |
| 2021/0180106 A1 | 6/2021 | Wochner et al. |
| 2021/0205434 A1 | 7/2021 | Petsch et al. |
| 2021/0260178 A1 | 8/2021 | Jasny et al. |
| 2021/0261897 A1 | 8/2021 | Yazdan Panah et al. |
| 2021/0361761 A1 | 11/2021 | Lutz et al. |
| 2021/0403925 A1 | 12/2021 | Chevessier-Tünnesen et al. |

(56) References Cited

U.S. PATENT DOCUMENTS

2022/0040281 A1 2/2022 Schwendt et al.
2022/0073962 A1 3/2022 Schwenger et al.

FOREIGN PATENT DOCUMENTS

| | | |
|---|---|---|
| DE | 10148886 | 4/2003 |
| DE | 69819150 | 7/2004 |
| DE | 102006007433 | 8/2007 |
| EP | 0347501 | 12/1989 |
| EP | 0772619 | 5/1997 |
| EP | 0839912 | 5/1998 |
| EP | 1063232 | 3/2001 |
| EP | 1083232 | 3/2001 |
| EP | 1167379 | 1/2002 |
| EP | 1374894 | 1/2004 |
| EP | 1393745 | 3/2004 |
| EP | 1564291 | 8/2005 |
| EP | 1905844 | 2/2008 |
| JP | 2005-521749 | 7/2005 |
| JP | 2008-507271 | 3/2008 |
| JP | 2008-542500 | 11/2008 |
| KR | 10-1003622 | 9/2003 |
| KR | 10-1051785 | 1/2005 |
| KR | 10-1032853 | 4/2005 |
| RU | 2407749 C2 | 12/2007 |
| RU | 2010135630 A1 | 3/2012 |
| WO | WO 1991/005560 | 5/1991 |
| WO | WO 1994/017093 | 8/1994 |
| WO | WO 1994/017792 | 8/1994 |
| WO | WO 1998/019710 | 5/1998 |
| WO | WO 1998/047913 | 10/1998 |
| WO | WO 1999/053961 | 10/1999 |
| WO | WO 2000/075304 | 12/2000 |
| WO | WO 2001/004135 | 1/2001 |
| WO | WO 2001/054720 | 8/2001 |
| WO | WO 2001/075164 | 10/2001 |
| WO | WO 2001/093902 | 12/2001 |
| WO | WO 2001/097843 | 12/2001 |
| WO | WO 2002/000594 | 1/2002 |
| WO | WO 2002/000694 | 1/2002 |
| WO | WO 2002/078614 | 10/2002 |
| WO | WO 2002/085434 | 10/2002 |
| WO | WO 2002/098443 | 12/2002 |
| WO | WO 2003/000227 | 1/2003 |
| WO | WO 2003/028656 | 4/2003 |
| WO | WO 2003/057822 | 7/2003 |
| WO | WO 2003/059381 | 7/2003 |
| WO | WO 2003/066649 | 8/2003 |
| WO | WO 2003/068942 | 8/2003 |
| WO | WO 2003/086280 | 10/2003 |
| WO | WO 2004/004743 | 1/2004 |
| WO | WO 2004/058159 | 7/2004 |
| WO | WO 2004/064782 | 8/2004 |
| WO | WO 2004/092329 | 10/2004 |
| WO | WO 2005/001022 | 1/2005 |
| WO | WO 2005/030259 | 4/2005 |
| WO | WO 2005/035549 | 4/2005 |
| WO | WO 2005/039501 | 5/2005 |
| WO | WO 2005/062947 | 7/2005 |
| WO | WO 2005/097993 | 10/2005 |
| WO | WO 2006/015789 | 2/2006 |
| WO | WO 2006/022712 | 3/2006 |
| WO | WO 2006/029223 | 3/2006 |
| WO | WO 2006/046978 | 5/2006 |
| WO | WO 2006/050280 | 5/2006 |
| WO | WO 2006/069782 | 7/2006 |
| WO | WO 2006/080946 | 8/2006 |
| WO | WO 2006/116458 | 11/2006 |
| WO | WO 2007/008300 | 1/2007 |
| WO | WO 2007/031319 | 3/2007 |
| WO | WO 2007/031322 | 3/2007 |
| WO | WO 2007/042554 | 4/2007 |
| WO | WO 2007/051303 | 5/2007 |
| WO | WO 2007/062107 | 5/2007 |
| WO | WO 2007/069068 | 6/2007 |
| WO | WO 2007/124755 | 11/2007 |
| WO | WO 2008/014979 | 2/2008 |
| WO | WO 2008/022046 | 2/2008 |
| WO | WO 2009/030254 | 3/2009 |
| WO | WO 2009/030481 | 3/2009 |
| WO | WO 2009/046739 | 4/2009 |
| WO | WO 2009/053700 | 4/2009 |
| WO | WO 2009/086640 | 7/2009 |
| WO | WO 2009/095226 | 8/2009 |
| WO | WO 2009/127230 | 10/2009 |
| WO | WO 2009/144230 | 12/2009 |
| WO | WO 2010/027827 | 3/2010 |
| WO | WO 2010/037408 | 4/2010 |
| WO | WO 2010/037539 | 4/2010 |
| WO | WO 2010/088927 | 8/2010 |
| WO | WO 2011/011631 | 1/2011 |
| WO | WO 2011/026641 | 3/2011 |
| WO | WO 2011/069528 | 6/2011 |
| WO | WO 2011/069587 | 6/2011 |
| WO | WO 2011/144358 | 11/2011 |
| WO | WO 2012/013326 | 2/2012 |
| WO | WO 2012/019630 | 2/2012 |
| WO | WO 2012/019780 | 2/2012 |
| WO | WO 2012/037078 | 3/2012 |
| WO | WO 2012/089338 | 7/2012 |
| WO | WO 2012/113413 | 8/2012 |
| WO | WO 2012/113513 | 8/2012 |
| WO | WO 2012/116714 | 9/2012 |
| WO | WO 2012/116715 | 9/2012 |
| WO | WO 2012/116810 | 9/2012 |
| WO | WO 2012/116811 | 9/2012 |
| WO | WO 2013/113325 | 8/2013 |
| WO | WO 2013/113326 | 8/2013 |
| WO | WO 2013/113501 | 8/2013 |
| WO | WO 2013/113502 | 8/2013 |
| WO | WO 2013/113736 | 8/2013 |
| WO | WO 2013/120626 | 8/2013 |
| WO | WO 2013/120627 | 8/2013 |
| WO | WO 2013/120628 | 8/2013 |
| WO | WO 2013/120629 | 8/2013 |
| WO | WO 2013/143698 | 10/2013 |
| WO | WO 2013/143699 | 10/2013 |
| WO | WO 2013/143700 | 10/2013 |
| WO | WO 2013/174409 | 11/2013 |
| WO | WO 2014/127917 | 8/2014 |
| WO | WO 2015/024664 | 2/2015 |
| WO | WO 2015/024665 | 2/2015 |
| WO | WO 2015/024666 | 2/2015 |
| WO | WO 2015/024667 | 2/2015 |
| WO | WO 2015/024668 | 2/2015 |
| WO | WO 2015/024669 | 2/2015 |
| WO | WO 2015/101414 | 7/2015 |
| WO | WO 2015/149944 | 10/2015 |
| WO | WO 2016/091391 | 6/2016 |
| WO | WO 2016/097065 | 6/2016 |
| WO | WO 2016/107877 | 7/2016 |
| WO | WO 2016/170176 | 10/2016 |

OTHER PUBLICATIONS

"SPT (Antigen Formulation)," Violin: Vaccine investigation and online information network, located at http://www.violinet.org/vaxjo/vaxjo_detail.php?c_vaxjo_id=72, downloaded on Aug. 21, 2012.
"Virus-like particle," Wikipedia, located at http://en.wikipedia.org/wiki/virus-like_particle, downloaded on Sep. 3, 2012.
Adams et al., "Preparation and hybridization properties of oligonucleotides containing 1-alpha-D-arabinofuranosylthymine", *Nucleic Acids Res.*, 19(13):3647-51, 1991.
Agrawal, "Antisense oligonucleotides: towards clinical trials", *Trends Biotechnol.*, 14(10):376-387, 1996.
Anderson et al., "Strategic priorities for respiratory syncytial virus (RSV) vaccine development," *Vaccine*, 31S:B209-B215, 2013.
Andreu et al., "Formation of disulfide bonds in synethetic peptides and proteins," Chapter 7, *Methods in Molecular Biology*, vol. 35, Peptide Synthesis Protocols, Pennington and Dunn, 1994.
Ara et al., "Zymosan enhances the immune response to DNA vaccine for human immunodeficiency virus type-1 through the

(56) References Cited

OTHER PUBLICATIONS activation of complement system", *Immunology*, 103(1):98-105, 2001.
Bauer et al., "The impact of intragenic CpG content on gene expression," *Nucleic Acids Research*, 38(12):3891-3908, 2010.
Bayard et al., "Antiviral activity in L1210 cells of liposome-encapsulated (2'- 5')oligo(adenylate)analogues", *Eur J Biochem.*, 151(2):319-326, 1985.
Berzofsky et al., "Progress on new vaccine strategies against chronic viral infections", *J Clin Invest.*, 114(4):450-62, 2004.
Bettinger T. et al., "Peptide-mediated RNA delivery: a novel approach for enhanced transfection of primary and Post-mitotic cells," *Nucleic Acids Research*, vol. 29, No. 18, pp. 3882-3891, 2001.
Blaxter et al., "The *Brugia malayi* genome project: expressed sequence tags and gene discovery", *Transactions of the Royal Society of Tropical Medicine and Hygiene*, 96(1):1-17, 2002.
Bocchia et al., "Antitumor vaccination: where we stand", *Heamatologica*, 85(11):1172-1206, 2000.
Bolhassani A et al., "Improvement of different vaccine delivery systems for cancer therapy," *Molecular Cancer*, vol. 10, No. 1, p. 3, Jan. 7, 2011.
Bot A. et al., "Enhanced protection against influenza virus of mice immunized as newborns with a mixture of plasmids expressing hemagglutinin and nucleoprotein," *Vaccine*, 16, No. 17, pp. 1675-1682, Oct. 1, 1998.
Bot A. et al., "Genetic immunization of neonates, Microbes and Infection, Institut Pasteur," vol. 4, No. 4, pp. 511-520, Apr. 2002.
Bot A. et al., "Induction of humoral and cellular immunity against influenza virus by immunization of newborn mice with a plasmid bearing a hemagglutinin gene," *International Immunology*, vol. 9, No. 11, pp. 1641-1650, Dec. 31, 1997.
Brito et al., "Non-viral eNOS gene delivery and transfection with stents for the treatment of restenosis," *BioMedical Engineering OnLine*, 9:56, 2010.
Burke R.S. et al., "Extracellular barriers to in Vivo PEI and PEGylated PEI polyplex-mediated gene delivery to the liver," *Bioconjug Chem.* Mar. 2008;19(3):693-704. Epub Feb. 23, 2008.
Buteau et al., "Challenges in the development of effective peptide vaccines for cancer", *Mayo Clin Proc.*, 77:339-349, 2002.
Cancer.net, "What are Cancer Vaccines?" Jun. 2018, 4 pages (Year: 2018).
CAPLUS accession No. 190686-49-8; *Brugia malayi* strain TRS Labs conie RRAMCA1537 EST; *Chemical Abstracts Services*; Database Caplus; Jun. 2009.
Carralot J-P. et al., "Polarization of immunity induced by direct injection of naked sequence-stabilized mRNA vaccines," *CMLS Cellular and Molecular Life Sciences*, vo. 61, No. 18, pp. 2418-2424, Sep. 1, 2004.
Casciato et al., Manual of Clinical Oncology, 6th Edition, Lippincott Williams & Wilkins, 2009.
Cooper et al., "CPG 7909 adjuvant improves hepatitis B virus vaccine seroprotection in antiretroviral-treated HIV-infected adults," *AIDS*, 19:1473-1479, 2005.
Danhier et al., "PLGA-based nanoparticles: An overview of biomedical applications," *Journal of Controlled Release*, 161:505-522, 2012.
Declaration of Regina Heidenreich Under 37 C.F.R. §1.132, regarding Lipford et al., submitted in U.S. Appl. No. 14/375,215, executed Jun. 1, 2018.
Declaration of Regina Heidenreich Under 37 C.F.R. §1.132, regarding Heidenreich et al., submitted in U.S. Appl. No. 14/375,215, executed Jun. 1, 2018.
Deshayes S. et al., "Cell-penetrating peptides: tools for intracellular delivery of therapeutics," *Cell Mol Life Sci.*, 62(16):1839-49. Review. 2005.
Diebold et al., "Innate antiviral responses by means of TLR7-mediated recognition of single-stranded RNA", *Science*, 1529-1531, 2004.

Dmitriev, "Bactenecin 7 peptide fragment as a tool for intracellular delivery of a phosphorescent oxygen sensor," *FEBS Journal*, 277:4651-4661, 2010.
Dohmen et al., "Nanoparticle-based programmed drug and nucleic acid delivery—an option for nanomedicine," *J. Vascular Res.*, 48/s1:67, Abstract IS45, 2011.
EBI Database accession No. BP836659; *Arabidopsis thaliana* clone RAFL22-17-C17 EST; Database EMBL; Jan. 2005.
EBI Database accession No. CZ193289; PST12107-MICB1 *Mus musculus* genomic clone PST12107-NR; Database EMBL; Feb. 2005.
EBI Database accession No. DN868844; NEIBank analysis of Dog lens; Wistow, G., Database EMBL; Apr. 2005.
Eliyahu et al., "Polymers for DNA delivery," *Molecules*, 10:34-64, 2005.
EMBL accession No. AA430815; Brugia malayi strain TRS Labs clone RRAMCA1537 Est; Database EMBL; May 1997.
Fajac I. et al., "Histidylated polylysine as a synthetic vector for gene transfer into immortalized cystic fibrosis airway surface and airway gland serous cells," *J Gene Med*. 2(5):368-78. Sep.-Oct., 2000.
Feroze-Merzoug et al., "Molecular profiling in prostate cancer", *Cancer and Metastasis Reviews*, 20:165-171, 2001.
Fire et al., "Potent and specific genetic interferences by double-stranded RNA in *Caenorhabditis elegans*", 391:806-811, 1998.
Foerg C. et al., "On the biomedical promise of cell penetrating peptides: limits versus prospects," *J Pharm Sci.*, 97(1):144-62, 2008.
Fotin-Mleczek et al., "Highly potent mRNA based cancer vaccines represent an attractive platform for combination therapies supporting an improved therapeutic effect," *The Journal of Gene Medicine*, 14(6):428-439, 2012.
Fotin-Mleczek et al., "Messenger RNA-based vaccines with dual activity induce balanced TLR-7 dependent adaptive immune responses and provide antitumor activity", *Journal of Immunotheraphy*, 34(1):1-15, 2011.
Fox, "Squalene emulsions for parenteral vaccine and drug delivery," *Molecules*, 14:3286-3312, 2009.
Fujita T. et al., "Calcium enhanced delivery of tetraarginine-PEG-lipid-coated DNA/protamine complexes," *International Journal of Pharmaceutics*, vol. 368, No. 1-2, pp. 186-192, Feb. 23, 2009.
Galbraith et al., "Complement activation and hemodynamic changes following intravenous administration of phosphorothioate oligonucleotides in the monkey", *Antisense Research and Development*, 4:201-206, 1994.
Gao X et al., Nonviral gene delivery: what we know and what is next, *AAPS J.* 23;9(1):E92-104. Review. Mar. 2007.
Garinot et al., "PEGylated PLGA-based nanoparticles targeting M cells for oral vaccination," *Journal of controlled release*, vol. 120, No. 3, pp. 195-204, Jul. 17, 2007.
GenBank Accession No. JK489756.1, Gi; 346421249, publicly available Sep. 2011.
GenBank Accession No. EF566942, 2007, p. 1-2.
Gerogieva et al., "Comparative study on the changes in photosynthetic activity of the homoiochlorophyllous desiccation-tolerant *Haberlea rhodopensis* and desiccation-sensitive spinach leaves during desiccation and rehydration", *Photosynthesis Research*, 65:191-203, 2005.
Giel-Peitraszuk M et al., "Database Biosis," DB Acc. No. Prev199800116011, 1997.
Gravekamp et al., "Cancer vaccines in old age," *Experimental Gerontology*, vol. 42, No. 5, pp. 441-450, Apr. 14, 2007.
Gryaznov, "Oligonucleotide N3'—P5' phosphoramidates as potential therapeutic agents", *Biochimica et Biophysica Acta*, 1489:131-140, 1999.
Hamidi M. et al., "Pharmacokinetic consequences of pegylation," *Drug Deliv.*; 13(6) pp. 399-409, 2006.
Hamm et al., "Immunostimulatory RNA is a potent inducer of antigen-specific cytotoxic and humoral immune response in vivo," *International Immunology*, 19(3):297-304, 2007.
Hardy et al., "Synergistic effects of gene delivery—co-formulation of small disulfide-linked dendritic polycations with Lipofectamine 2000", *Organic and Biomolecular Chemistry*, 7(4):789-793, 2009.

(56) References Cited

OTHER PUBLICATIONS

Hashimoto et al., "Neutralizing epitopes of RSV and palivizumab resistance in Japan", Fukushima J. Med. Sci., 63(3):127-134, 2017.
Hausch et al., "A novel carboxy-functionalized photocleavable dinucleotide analog for the selection to RNA catalysts", Tetrahedron Letters, 39(34):6157-6158, 1998.
Hause et al., "Sequence variability of the respiratory syncytial virus (RSV) fusion gene among contemporary and historical genotypes of RSV/A and RSV/B", PLoS ONE, 12(4):e0175792, 2017.
Heffernan et al., " Disulfide-crosslinke plyion micelles for delivery of protein therapeutics", Annals of Biomedical Engineering, 37(10):1993-2002, 2009.
Heidenreich et al., "A novel RNA-based adjuvant combines strong immunostimulatory capacities with a favorable safety profile," Int. J. Cancer, 137(2):372-384, 2015.
Heidenreich et al., "Chemically modified RNA: approaches and applications", The FASEB Journal, 7(1):90-6, 1993.
Heidenreich et al., "RNAdjuvant, a novel highly potent RNA-based adjuvant supports induction of balanced immune response (TH1 and TH2) and anti-tumor activity," J. Immunotherapy, Meeting Info: 26th Annual Scientific Meeting of Society of Immunotherapy of Cancer, Abstract only, 34(9):663-664, 2011.
Heil et al., "Species-specific recognition of single-stranded RNA via Toll-like receptor 7 and 8", Science, vol. 303, pp. 1526-1529, 2004.
Herbert et al., "Lipid modification of GRN163, an N3'—P5' thio-phosphoramidate oligonucleotide enhances the potency telomerase inhibition", Oncogene, 24:5262-5268, 2005.
Herbert et al., The Dictionary of Immunology, Academic Press: San Diego, $4^{th}$ ed. 1995. Print.
Heyman, "The immune complex: possible ways of regulating the antibody response", Immunology Today, 11(9):310-313, 1990.
Higgins et al., "Advances in RSV vaccine research and development—A global agenda," Vaccine, 34(26):2870-2875, 2016.
Hoerr et al., "In vivo application of RNA leads to induction of specific cytotoxic T lymphocytes and antibodies", Eur J Immunol., 30(1):1-7, 2000.
Huang et al., "Recent development of therapeutics for chronic HCV infection", Antiviral Res., 71:351-362, 2006.
Huget et al., "Adjuvant and suppressor activity of the polycation protamine hydrochloride in the primary immune response of mice", Z Immunitatsforsch Immunobiol., 152(3):190-9, 1976. (English Abstract).
Hwang et al., "A brain-targeted rabies virus glycoprotein-disulfide linked PEI nanocarrier for delivery of neurogenic microRNA," Biomaterials, 32:4968-4975, 2011.
Janssens et al., "Role of toll-like receptors in pathogen recognition", Clinical Microbiology Reviews, 16(4):637-646, 2003.
Jones et al., "Sendai virus-based RSV vaccine protects African green monkeys from RSV infection," Vaccine, 30(5):959-968, 2012.
Kallen et al., "A novel, disruptive vaccination technology," Human Vaccines & Immunotherapeutics, 9(10):2263-2276, 2013.
Kilk, "Cell-penetrating peptides and bioactive cargoes. Strategies and mechanisms," Department of Neurochemistry and Neurotoxicology, Stockholm University, Doctoral dissertation, 2004.
Kim et al., "Bioreducible polymers for gene delivery," React Funct Polym, 71(3):344-349, 2011.
Kim et al., "VeGF siRNA delivery system using arginine-grafted bioreducible poly(disulfide amine)", Molecular Pharmaceutics, 6(3):718-726, 2009.
Knop et al., "Poly(ethylene glycol) in drug delivery: pros and cons as well as potential alternatives," Angew. Chem. Int. Ed., 49:6288-6308, 2010.
Kovarik J. et al., "Optimization of vaccine responses in early life: the role of delivery systems and immunomodulators," Immunology and Cell Biology, vol. 76, No. 3, pp. 222-236, Jun. 1998.
Koziel et al., "Hepatitis C virus (HCV)-specific cytotoxic T lymphocytes recognize epitopes in the core and envelope proteins of HCV", J Virol., 67(12):7522-32, 1993.
Kwiatkowski et al., "The 9-(4-Octadecyloxyphenylxanthen)-9-yl-Group. A new Acid-labile Hydroxyl Protective Group and Its Application in the Preparative Reverse-phase Chromatographic Separation of Oligoribonucleotides", Acta Chemica Scandinavica, 38b:657-671, 1984.
Kwok KY et al., "Formulation of highly soluble poly(ethylene glycol)-peptide DNA condensates," J Pharm Sci.; 88(10):996-1003, Oct. 1999.
Lo et al., "An endosomolytic Tat peptide produced by incorporation of histidine and cysteine residues as a nonviral vector for DNA transfection", Biomaterials, 29(15):2408-2414, 2008.
Lochmann et al., "Drug delivery of oligonucleotides by peptides," European Journal of Pharmaceutics and Biopharmaceutics; vol. 58, No. 2, pp. 237-251, 2004.
Martin M.E et al., "Peptide-guided gene delivery," AAPS J. 9;9(1):E18-29. Review. Feb. 2007.
Mateo et al., "An HLA-A2 polyepitope vaccine for melanoma immunotheraphy", J Immunol., 163:4058-4063, 1999.
Matray and Gryaznov., "Synthesis and properties of RNA analogs-oligoribonucleotide N3'P5' phosphoramidates", Nucleic Acids Research, 27(20):3976-85, 1999.
Mattner et al., "Vaccination with poly-L-arginine as immunostimulant for peptide vaccines: induction of potent and long-lasting T-cell responses against cancer antigens," Cancer Research, 62(5): 1477-1480, 2002.
McKkenzie et al., "A potent new class of reductively activated peptide gene delivery agents", Journal of Biological Chemistry, 275(14):9970-9977, 2000.
McKenzie et al., "Low molecular weight disulfide cross-linking peptides as nonviral gene discovery carriers", Bioconjugate Chemistry, 11(6):901-909, 2000.
McLellan et al., "Structure and Function of Respiratory Syncytial Virus Surface Glycoproteins", Curr. Top. Microbiol. Immunol., 372:83-104, 2014.
Melief et al., "Immunotherapy of established (pre)malignant disease by synthetic long peptide vaccines," Nature Reviews Cancer, 8:351-360, 2008.
Milich et al., "The hepatitis B virus core and e antigens elicit different Th cell subsets: antigen structure can affect Th cell phenotype", J Virol., 71(3):2192-201, 1997.
Minks et al., "Structural requirements of double-stranded RNA for the activation of 2',5'-oligo(A)polymerase and protein kinase of interferon-treated HeLa cells", The Journal of Biological Chemistry, 254(20):10180-10183, 1979.
Miyata et al., "Block catiomer polyplexes with regulated densities of charge and disulfide cross-linking directed to enhance gene expression", Journal of the American Chemical Society, 126(8):2355-2361, 2004.
Mocellin et al., "Part I: Vaccines for solid tumours," The Lancet/Oncology, 5:681-689, 2004.
Nakamura Y et al., "Octaarginine-modified multifunctional envelope-type nano device for siRNA," J Control Release. Jun. 22, 2007, 119(3):360-7. Epub Mar. 23, 2007.
National Cancer Institute, Fact Sheet, Cancer Vaccines, Jun. 21, 2011, 9 pages (Year: 2011).
Neu M et al., "Recent advances in rational gene transfer vector design based on poly( ethylene imine) and its derivatives," J Gene Med., 7(8):992-1009, Aug. 2005.
Nicholson et al., "Accurate in vitro cleavage by RNase III of phosphorothioate-substituted RNA processing signals in bacteriophage T7 early mRNA", Nucleic Acids Res., 16(4):1577-91, 1988.
Office Communication issued in corresponding Japanese Application No. 2019-180689, dated Oct. 6, 2020. English translation appended.
Office Communication issued in U.S. Appl. No. 13/824,449, dated Jan. 29, 2016.
Office Communication issued in U.S. Appl. No. 13/824,449, dated May 8, 2015.
Office Communication issued in U.S. Appl. No. 13/824,449, dated Sep. 17, 2014.
Office Communication issued in U.S. Appl. No. 14/375,215, dated Feb. 4, 2016.
Office Communication issued in U.S. Appl. No. 14/375,215, dated Jan. 16, 2018.

(56) References Cited

OTHER PUBLICATIONS

Office Communication issued in U.S. Appl. No. 14/375,215, dated Jul. 9, 2015.
Office Communication issued in U.S. Appl. No. 14/375,215, dated May 30, 2019.
Office Communication issued in U.S. Appl. No. 14/375,215, dated Nov. 17, 2016.
Office Communication issued in U.S. Appl. No. 14/375,215, dated Oct. 5, 2018.
Office Communication issued in U.S. Appl. No. 15/048,439, dated Feb. 22, 2017.
Office Communication issued in U.S. Appl. No. 15/206,036, dated Mar. 23, 2017.
Office Communication issued in U.S. Appl. No. 15/206,036, dated Nov. 22, 2017.
Office Communication issued in U.S. Appl. No. 15/206,036, dated Sep. 11, 2018.
Office Communication issued in U.S. Appl. No. 15/206,036, dated Jun. 25, 2019.
Office Communication issued in U.S. Appl. No. 15/300,682, dated Jan. 29, 2018.
Office Communication issued in U.S. Appl. No. 15/300,682, dated May 25, 2018.
Office Communication issued in U.S. Appl. No. 15/300,682, dated Jan. 7, 2019.
Office Communication issued in U.S. Appl. No. 15/300,682, dated Mar. 20, 2019.
Office Communication issued in U.S. Appl. No. 15/488,815, dated Jan. 9, 2018.
Office Communication issued in U.S. Appl. No. 15/488,815, dated Jul. 25, 2018.
Office Communication issued in U.S. Appl. No. 16/168,747, dated Apr. 30, 2020.
Office Communication issued in U.S. Appl. No. 16/168,747, dated Feb. 11, 2021.
Office Communication issued in U.S. Appl. No. 16/445,134, dated Oct. 1, 2020.
Office Communication issued in U.S. Appl. No. 16/445,134, dated May 13, 2021.
Office Communication issued in U.S. Appl. No. 16/555,881, dated Mar. 5, 2020.
Office Communication issued in U.S. Appl. No. 16/555,881, dated Aug. 6, 2020.
Office Communication issued in U.S. Appl. No. 16/555,881, dated Jun. 24, 2021.
Office Communication issued in U.S. Appl. No. 17/316,834, dated Oct. 6, 2022.
Office Communication issued in U.S. Appl. No. 17/316,834, dated May 19, 2023.
Oomens et al., "The cytoplasmic tail of the human respiratory syncytial virus F protein Plays critical roles in cellular localization of the F protein and infectious progeny production," *Journal of Virology*, 80(21):10465-10477, 2006.
Oupicky D. et al., "Importance of lateral and steric stabilization of polyelectrolyte gene delivery vectors for extended systemic circulation," Mol Ther., 5(4):463-72, Apr. 2002.
Oupicky D. et al., "Laterally stabilized complexes of DNA with linear reducible polycations: strategy for triggered intracellular activation of DNA delivery vectors," *J Am Chem. Soc.*, 124(1):8-9, Soc., Jan. 9, 2002.
Parker A.L. et al., "Enhanced gene transfer activity of peptide-targeted gene-delivery vectors," *J Drug Target.*, 13(1):39-51, Jan. 2005.
Parkinson et al., "A transcriptomic analysis of the phylum Nematoda", *Nature Genetics*, 36(12):1259-1267, 2004.
PCT International Search Report and Written Opinion issued in International Application No. PCT/EP2015/000706, dated Oct. 13, 2015.
PCT International Search Report and Written Opinion issued in International Application No. PCT/EP2014/002301, dated Mar. 6, 2015.
Petsch et al., "Protective efficacy of in vitro synthesized, specific mRNA vaccines against influenza A virus infection," *Nature Biotechnology*, 30(12):1210-1216, 2012.
Pichon C. et al., "Poly[Lys-(AEDTP)]: a cationic polymer that allows dissociation of pDNA/cationic polymer complexes in a reductive medium and enhances polyfection," *Bioconjug Chem.*, 13(1):76-82, Jan.-Feb. 2002.
Pomroy N.C. et al., "Solubilization of hydrophobic peptides by reversible cysteine PEGylation," Biochem Biophys Res Commun., 245(2):618-21, Apr. 17, 1998.
Racanelli et al., "Presentation of HCV antigens to naïve CD8+T cells: why the where, when, what and how are important for virus control and infection outcome", *Clin Immunol.*, 124(1):5-12, 2007.
Radu D.L. et al., "Plasmid expressing the influenza HA gene protects old mice from lethal challenge with influenza viraus," *Viral Immunology*, vol. 12, No. 3, pp. 217-226, 1999.
Ramazeilles et al., "Antisense phosphorothioate oligonucleotides: selective killing of the intracellular parasite *Leishmania amazonensis*", Proc Natl Acad Sci USA, 91(17):7859-63, 1994.
Read et al., "Vectors based on reducible polycations facilitate intracellular release of nucleic acids", *The Journal of Gene Medicine*, 5(3):232-245, 2003.
Read M.L. et al., "A versatile reducible polycation-based system for efficient delivery of a broad range of nucleic acids," *Nucleic Acids Res.*, 33(9): e86, May 24, 2005.
Read M.L. et al., "RNA-based therapeutic strategies for cancer," *Expert Opinion on Therapeutic Patents*, vol. 13, No. 5, pp. 627-638, 2003.
Riedl et al., "Priming Th1 immunity to viral core particles is facilitated by trace amounts of RNA bound to its arginine-rich domain", *J Immunol.*, 168(10):4951-9, 2002.
Rittner et al., "New basic membrane-destabilizing peptides for plasmid-based gene delivery in Vitro and in Vivo," *Molecular Therapy*, 5(2)104-114, 2002.
Rollier et al., "Control of heterologous hepatitis C virus infection in chimpanzees is associated with the quality of vaccine-induced peripheral t-helper immune response", *J Virol.*, 78(1):187-196, 2004.
Romagne et al., "Current and future drugs targeting one class of innate immunity receptors: the toll-like receptors", *Drug Discov Today*, 12(1-2):80-7, 2007.
Rozenfeld et al., "Stable assemblies of cationic bilayer fragments and CpG oligonucleotide with enhanced immunoadjuvant activity in vivo", *Journal of Controlled Release*, 160(2):367-373, 2011.
Saenz-Badillos et al., "RNA as a tumor vaccine: a review of the literature", *Exp Dermatol.*, 10(3):143-154, 2001.
Sakae M. et al., "Highly efficient in vivo gene transfection by plasmid/PEI complexes coated by anionic PEG derivatives bearing carboxyl groups and RGD peptide," *Biomedicine and Pharmacotherapy*, vol. 62, No. 7, pp. 448-453, Sep. 1, 2008.
Scheel et al., "Therapeutic anti-tumor immunity triggered by injections of immunostimulating single-stranded RNA," *Eur J Immunol*, vol. 36, No. 10, pp. 2807-2816, 2006.
Scheel et al., "Toll-like receptor-dependent activation of several human blood cell types by protamine-condensed mRNA," *Eur J Immunol*, vol. 35, No. 5, pp. 1557-1566, 2005.
Scheel et al., "Immunostimulating capacities of stabilized RNA molecules", *Eur J Immunol.*, 24:537-547, 2004.
Scheel et al., "mRNA as immunostimulatory molecule", Krebsimmuntherapie Annual Meeting, Oral Presentation May 9, 2003. (Abstract).
Schirrmacher et al., "Intra-pinna anti-tumor vaccinaton with self-replicating infectious RNA or with DNA encoding a model tumor antigen and a cytokine", *Gene Therapy*, 7(13):1137-1147, 2000.
Schlake et al., "Developing mRNA-vaccine technologies," *RNA Biology*, 9(11):1319-1330, 2012.
Shea et al., "Synthesis, hybridization properties and antiviral activity of lipid-oligodeoxynucleotide conjugates", *Nucleic Acids Research*, 18(13):3777-3783, 1990.

(56) References Cited

OTHER PUBLICATIONS

Shiffman et al., "Protein dissociation from DNA in model systems and chromatin," *Nucleic Acids Res.*, 5(9):3409-3426, 1978.
Shirai et al., "An epitope in hepatitis C virus core region recognized by cytotoxic T cells in mice and humans", *J Virol.*, 68(5):3334-3342, 1994.
Stephens et al., "Sequence analysis of the major outer membrane protein gene from *Chlamydia trachomatis* serovar L2", *Journal of Bacteriology*, 168(3):1277-1282, 1986.
Sun et al., "Advances in saponin-based adjuvants," *Vaccine*, 27:1787-1796, 2009.
Takae S. et al., "PEG-detachable polyplex micelles based on disulfide-linked block catiomers as bioresponsive nonviral gene vectors," *J Am Chem Soc.*, 130(18):6001-9, May 7, 2008. Epub Apr. 9, 2008.
Tan et al., "Strategies for hepatitis C therapeutic intervention: now and next", *Curr Opin in Pharmacology*, 4:465-470, 2004.
Tanaka et al., "Disulfide crosslinked stearoyl carrier peptides containing arginine and histidine enhance siRNA uptake and gene silencing," *International Journal of Pharmaceutics*, 398:219-224, 2010.
Teplova et al., "Crystal structure and improved antisense properties of 2'-O-(2-methoxyethyl)-RNA", *Nature Structural Biology*, 6(6):535-539, 1999.
Ternette et al. "Expression of RNA virus proteins by RNA polymerase II dependent expression plasmids is hindered at multiple steps," Virology Journal, 4:51, 2007, p. 1-10.
Tokunaga et al., "Effect of oligopeptides on gene expression: comparison of DNA/peptide and DNA/peptide/liposome complexes", *International Journal of Pharmaceutics*, 269(1):71-80, 2004.
Tönges L. et al., "Stearylated octaarginine and artificial virus-like particles for transfection of siRNA into primary rat neurons," *RNA*, 12(7):1431-8. Epub May 12, 2006.
Trinchieri et al., "Cooperation of toll-like receptor signals in innate immune defence", *Nature Reviews Immunology*, 7:179-190, 2007.
Tse et al., "Update on toll-like receptor-directed therapies for human disease", *Ann Rheum Dis.*, 66 Suppl 3:iii77-80, 2007.
Unnamalai N. et al., "Cationic oligopeptide-mediated delivery of dsRNA for posttranscriptional gene silencing in plant cells," *FEBS Lett.*, 566(1-3):307-10, May 21, 2004.
Vivès E. et al., "A truncated HIV-1 Tat protein basic domain rapidly translocates through the plasma membrane and accumulates in the cell nucleus," *J Biol Chem.*, 272(25):16010-7, Jun. 20, 1997.
Wang Y.H. et al., "An intracellular delivery method for siRNA by an arginine-rich peptide," *J Biochem Biophys Methods*, 70(4):579-86, Jun. 10, 2007. Epub Jan. 30, 2007.
Weide et al., "Direct injection of protamine-protected mRNA: results of a phase 1/2 vaccination trial in metastatic melanoma patients," J Immunother., 32(5):498-507, 2009.
Wyman et al., "Design, synthesis, and characterization of a cationic peptide that binds to nucleic acids and permeabilizes bilayers," *Biochemistry*, 36:3008-3017, 1997.
Xiong et al., "pH-responsive multi-PEGylated dual cationic nanoparticles enable charge modulations for safe gene delivery," *Chem Med Chem*, 2:1321-1327, 2007.
Yoshitomi et al., "Design of core-shell-type nanoparticles carrying stable radicals in the core," *Biomacromolecules*, 10:596-601, 2009.
Zhang et al., "Delivery of telomerase reverse transcriptase small interfering RNA in complex with positively charged single-walled carbon nanotubes suppresses tumor growth," *Clinical Cancer Research*, 12:4933-4939, 2006.
Zhang et al., "Personalized cancer vaccines: targeting the cancer mutanome," Vaccine 35:1094-1100, 2017.
Zhao et al., "N/P ratio significantly influences the transfection efficiency and cytotoxicity of a polyethylenimine/chitosan/DNA complex," Biol. Pharm. Bull., 32(4):706-710, 2009.
Zhou et al., "RNA melanoma vaccine: induction of antitumor immunity by human glycoprotein 100 mRNA immunization", *Human Gene Therapy*, 10:2719-2724, 1999.
Zimmermann et al., "Immunostimulatory DNA as adjuvant: efficacay of phosphodiester CpG oligonucleotides is enhanced by 3' sequence modifications", *Vaccine*, 21(9-10):990-5, 2003. (abstract only).
Zohra et al., "Effective delivery with enhanced translational activity synergistically accelerates mRNA-based transfection," *Biochem Biphys Res Commun.*, 358(1):373-378, 2007.

* cited by examiner

RSV-F long (GC) R1691

```
GGGAGAAAGCUUACCAUGGAGCUGCCCAUCCUCAAGGCCAACGCCAUCACCACCAUCCUG
GCGGCCGUGACGUUCUGCUUCGCCAGCUCCCAGAACAUCACCGAGGAGUUCUACCAGAGC
ACCUGCUCCGCCGUCAGCAAGGGCUACCUGUCCGCCCUCCGGACCGGGUGGUACACGAGC
GUGAUCACCAUCGAGCUGUCCAACAUCAAGGAGAACAAGUGCAACGGCACCGACGCGAAG
GUGAAGCUGAUCAACCAGGAGCUCGACAAGUACAAGAACGCCGUCACCGAGCUGCAGCUG
CUCAUGCAGAGCACGACCGCCGCCAACAACCGCGCGCGGCGCGAGCUGCCGCGGUUCAUG
AACUACACCCUGAACAACACCAAGAAGACGAACGUGACCCUCUCCAAGAAGCGCAAGCGG
CGCUUCCUGGGGUUCCUGCUCGGCGUGGGGAGCGCCAUCGCCUCCGGCAUCGCCGUCAGC
AAGGUGCUGCACCUGGAGGGCGAGGUGAACAAGAUCAAGUCCGCCCUCCUGAGCACCAAC
AAGGCGGUCGUGUCCCUGAGCAACGGGGUGUCCGUCCUCACCAGCAAGGUGCUGGACCUG
AAGAACUACAUCGACAAGCAGCUCCUGCCCAUCGUGAACAAGCAGUCCUGCCGGAUCAGC
AACAUCGAGACGGUCAUCGAGUUCCAGCAGAAGAACAACCGCCUGCUCGAGAUCACCCGG
GAGUUCAGCGUGAACGCCGGCGUGACCACCCCCGUCUCCACGUACAUGCUGACCAACAGC
GAGCUGCUCUCCCUGAUCAACGACAUGCCCAUCACCAACGACCAGAAGAAGCUGAUGAGC
AACAACGUGCAGAUCGUGCGCCAGCAGUCCUACAGCAUCAUGUCCAUCAUCAAGGAGGAG
GUCCUCGCCUACGUGGUGCAGCUGCCGCUGUACGGGGUCAUCGACACCCCCUGCUGGAAG
CUCCACACGAGCCCCCUGUGCACCACCAACACCAAGGAGGGCUCCAACAUCUGCCUGACG
CGGACCGACCGCGGGUGGUACUGCGACAACGCCGGCAGCGUGUCCUUCUUCCCCCAGGCC
GAGACCUGCAAGGUCCAGAGCAACCGGGUGUUCUGCGACACCAUGAACUCCCUCACGCUG
CCGAGCGAGGUGAACCUGUGCAACGUCGACAUCUUCAACCCCAAGUACGACUGCAAGAUC
AUGACCUCCAAGACCGACGUGAGCUCCAGCGUGAUCACCUCCCUCGGCGCGAUCGUCAGC
UGCUACGGGAAGACGAAGUGCACCGCCAGCAACAAGAACCGCGGCAUCAUCAAGACCUUC
UCCAACGGGUGCGACUACGUGAGCAACAAGGGCGUGGACACCGUCUCCGUGGGCAACACC
CUGUACUACGUGAACAAGCAGGAGGGGAAGAGCCUGUACGUCAAGGGCGAGCCCAUCAUC
AACUUCUACGACCCCCUCGUGUUCCCGUCCGACGAGUUCGACGCCAGCAUCUCCCAGGUG
AACGAGAAGAUCAACCAGAGCCUGGCCUUCAUCCGGAAGUCCGACGAGCUGCUGCACCAC
GUCAACGCCGGGAAGAGCACGACCAACAUCAUGAUCACCACCAUCAUCAUCGUGAUCAUC
GUGAUCCUCCUGUCCCUGAUCGCGGUCGGCCUCCUGCUGUACUGCAAGGCCCGCAGCACG
CCCGUGACCCUCUCCAAGGACCAGCUGAGCGGGAUCAACAACAUCGCCUUCUCCAACUGA
GGACUAGUUAUAAGACUGACUAGCCCGAUGGGCCUCCCAACGGGCCCUCCUCCCCUCCUU
GCACCGAGAUUAAUAAAAAAAAAAAAAAAAAAAAAAAAAAAAAAAAAAAAAAAAAAAAAA
AAAAAAAAAAAAAAAAUGCAUCCCCCCCCCCCCCCCCCCCCCCCCCCCCCAAAGGC
UCUUUUCAGAGCCACCAGAAUU
```

Fig. 1

RSV-F long (GC) R2510

```
GGGGCGCUGCCUACGGAGGUGGCAGCCAUCUCCUUCUCGGCAUCAAGCUUACCAUGGAGC
UGCCCAUCCUCAAGGCCAACGCCAUCACCACCAUCCUGGCGGCCGUGACGUUCUGCUUCG
CCAGCUCCCAGAACAUCACCGAGGAGUUCUACCAGAGCACCUGCUCCGCCGUCAGCAAGG
GCUACCUGUCCGCCCUCCGGACCGGGUGGUACACGAGCGUGAUCACCAUCGAGCUGUCCA
ACAUCAAGGAGAACAAGUGCAACGGCACCGACGCGAAGGUGAAGCUGAUCAACCAGGAGC
UCGACAAGUACAAGAACGCCGUCACCGAGCUGCAGCUGCUCAUGCAGAGCACGACCGCCG
CCAACAACCGCGCGGCGCGAGCUGCCGCGGUUCAUGAACUACACCCUGAACAACACCA
AGAAGACGAACGUGACCCUCUCCAAGAAGCGCAAGCGGCGCUUCCUGGGGUUCCUGCUCG
GCGUGGGGAGCGCCAUCGCCUCCGGCAUCGCCGUCAGCAAGGUGCUGCACCUGGAGGGCG
AGGUGAACAAGAUCAAGUCCGCCCUCCUGAGCACCAACAAGGCGGUCGUGUCCCUGAGCA
ACGGGGUGUCCGUCCUCACCAGCAAGGUGCUGGACCUGAAGAACUACAUCGACAAGCAGC
UCCUGCCCAUCGUGAACAAGCAGUCCUGCCGGAUCAGCAACAUCGAGACGGUCAUCGAGU
UCCAGCAGAAGAACAACCGCCUGCUCGAGAUCACCCGGGAGUUCAGCGUGAACGCCGGCG
UGACCACCCCCGUCUCCACGUACAUGCUGACCAACAGCGAGCUGCUCUCCCUGAUCAACG
ACAUGCCCAUCACCAACGACCAGAAGAAGCUGAUGAGCAACAACGUGCAGAUCGUGCGCC
AGCAGUCCUACAGCAUCAUGUCCAUCAUCAAGGAGGAGGUCCUCGCCUACGUGGUGCAGC
UGCCGCUGUACGGGGUCAUCGACACCCCCUGCUGGAAGCUCCACACGAGCCCCCUGUGCA
CCACCAACACCAAGGAGGGCUCCAACAUCUGCCUGACGCGGACCGACCGCGGGUGGUACU
GCGACAACGCCGGCAGCGUGUCCUUCUUCCCCCAGGCCGAGACCUGCAAGGUCCAGAGCA
ACCGGGUGUUCUGCGACACCAUGAACUCCCUCACGCUGCCGAGCGAGGUGAACCUGUGCA
ACGUCGACAUCUUCAACCCCAAGUACGACUGCAAGAUCAUGACCUCCAAGACCGACGUGA
GCUCCAGCGUGAUCACCUCCCUCGGCGCGAUCGUCAGCUGCUACGGGAAGACGAAGUGCA
CCGCCAGCAACAAGAACCGCGGCAUCAUCAAGACCUUCUCCAACGGGUGCGACUACGUGA
GCAACAAGGGCGUGGACACCGUCUCCGUGGGCAACACCCUGUACUACGUGAACAAGCAGG
AGGGGAAGAGCCUGUACGUCAAGGGCGAGCCCAUCAUCAACUUCUACGACCCCCUCGUGU
UCCCGUCCGACGAGUUCGACGCCAGCAUCUCCCAGGUGAACGAGAAGAUCAACCAGAGCC
UGGCCUUCAUCCGGAAGUCCGACGAGCUGCUGCACCACGUCAACGCCGGGAAGAGCACGA
CCAACAUCAUGAUCACCACCAUCAUCAUCGUGAUCAUCGUGAUCCUCCUGUCCCUGAUCG
CGGUCGGCCUCCUGCUGUACUGCAAGGCCCGCAGCACGCCCGUGACCCUCUCCAAGGACC
AGCUGAGCGGGAUCAACAACAUCGCCUUCUCCAACUGAGGACUAGUGCAUCACAUUUAAA
AGCAUCUCAGCCUACCAUGAGAAUAAGAGAAAGAAAAUGAAGAUCAAUAGCUUAUUCAUC
UCUUUUUCUUUUUCGUUGGUGUAAAGCCAACACCCUGUCUAAAAAACAUAAAUUUCUUUA
AUCAUUUUGCCUCUUUUCUCUGUGCUUCAAUUAAUAAAAAAUGGAAAGAACCUAGAUCUA
AAAAAAAAAAAAAAAAAAAAAAAAAAAAAAAAAAAAAAAAAAAAAAAAAAAAAAAAAAAA
AAAUGCAUCCCCCCCCCCCCCCCCCCCCCCCCCCCCCAAAGGCUCUUUUCAGAGCCAC
CAGAAUU
```

Fig. 2

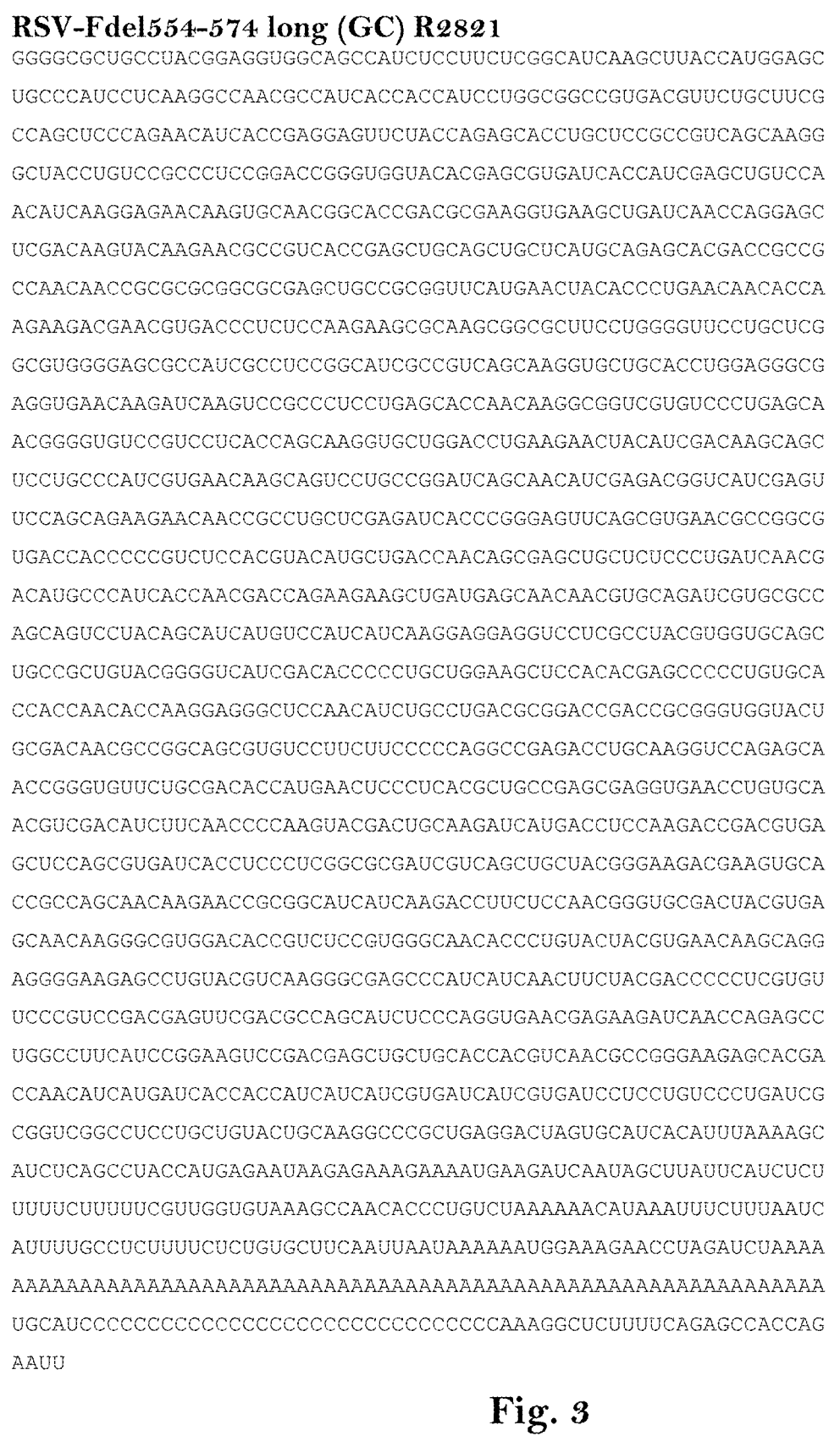

RSV-Fdel554-574 long (GC) R2821

```
GGGGCGCUGCCUAC

RSV-N (GC) R2831

GGGGCGCUGCCUACGGAGGUGGCAGCCAUCUCCUUCUCGGCAUCAAGCUUACCAUGGCCC
UGAGCAAGGUGAAGCUCAACGACACCCUGAACAAGGACCAGCUGCUCUCCAGCUCCAAGU
ACACCAUCCAGCGCAGCACGGGCGACUCCAUCGACACCCCCAACUACGACGUCCAGAAGC
ACAUCAACAAGCUGUGCGGGAUGCUGCUCAUCACCGAGGACGCCAACCACAAGUUCACCG
GCCUGAUCGGGAUGCUGUACGCGAUGAGCCGGCUCGGCCGCGAGGACACGAUCAAGAUCC
UGCGGGACGCCGGGUACCACGUGAAGGCCAACGGCGUGGACGUCACCACCCACCGCCAGG
ACAUCAACGGCAAGGAGAUGAAGUUCGAGGUGCUGACCCUCGCCUCCCUGACGACCGAGA
UCCAGAUCAACAUCGAGAUCGAGAGCCGGAAGUCCUACAAGAAGAUGCUGAAGGAGAUGG
GGGAGGUGGCCCCGGAGUACCGCCACGACAGCCCCGACUGCGGCAUGAUCAUCCUCUGCA
UCGCGGCCCUGGUCAUCACCAAGCUGGCCGCCGGGGACCGGUCCGGCCUCACCGCGGUGA
UCCGCCGGGCCAACAACGUGCUGAAGAACGAGAUGAAGCGCUACAAGGGGCUGCUCCCCA
AGGACAUCGCCAACAGCUUCUACGAGGUCUUCGAGAAGCACCCCCACUUCAUCGACGUGU
UCGUGCACUUCGGCAUCGCCCAGUCCAGCACGCGGGGCGGGUCCCGCGUCGAGGGCAUCU
UCGCCGGGCUGUUCAUGAACGCGUACGGCGCCGGCCAGGUGAUGCUGCGGUGGGGCGUGC
UCGCCAAGAGCGUCAAGAACAUCAUGCUGGGGCACGCCUCCGUGCAGGCCGAGAUGGAGC
AGGUGGUCGAGGUGUACGAGUACGCGCAGAAGCUGGGCGGCGAGGCCGGGUUCUACCACA
UCCUCAACAACCCGAAGGCCAGCCUGCUGUCCCUCACCCAGUUCCCGCACUUCAGCAGCG
UGGUCCUGGGGAACGCCGCCGGCCUGGGGAUCAUGGGCGAGUACCGCGGGACCCCGCGGA
ACCAGGACCUCUACGACGCGGCCAAGGCCUACGCCGAGCAGCUGAAGGAGAACGGCGUGA
UCAACUACUCCGUGCUGGACCUCACCGCCGAGGAGCUGGAGGCGAUCAAGCACCAGCUGA
ACCCCAAGGACAACGACGUCGAGCUCUGAGGACUAGUGCAUCACAUUUAAAAGCAUCUCA
GCCUACCAUGAGAAUAAGAGAAAGAAAAUGAAGAUCAAUAGCUUAUUCAUCUCUUUUUCU
UUUUCGUUGGUGUAAAGCCAACACCCUGUCUAAAAAACAUAAAUUUCUUUAAUCAUUUUG
CCUCUUUUCUCUGUGCUUCAAUUAAUAAAAAAUGGAAAGAACCUAGAUCUAAAAAAAAAA
AAAAAAAAAAAAAAAAAAAAAAAAAAAAAAAAAAAAAAAAAAAAAAAAAAAAAAUGCAUC
CCCCCCCCCCCCCCCCCCCCCCCCCCCCCCAAAGGCUCUUUUCAGAGCCACCAGAAUU

Fig. 4

RSV-M$_{2-1}$ (GC) R2833

GGGGCGCUGCCUACGGAGGUGGCAGCCAUCUCCUUCUCGGCAUCAAGCUUACCAUGAGCC
GCCGGAACCCCUGCAAGUUCGAGAUCCGCGGCCACUGCCUGAACGGGAAGCGGUGCCACU
UCUCCCACAACUACUUCGAGUGGCCGCCCCACGCCCUCCUGGUGCGCCAGAACUUCAUGC
UGAACCGGAUCCUCAAGAGCAUGGACAAGUCCAUCGACACCCUGAGCGAGAUCUCCGGCG
CCGCGGAGCUGGACCGCACCGAGGAGUACGCCCUCGGGGUCGUGGGCGUGCUGGAGAGCU
ACAUCGGGUCCAUCAACAACAUCACGAAGCAGAGCGCCUGCGUCGCCAUGUCCAAGCUGC
UCACCGAGCUGAACAGCGACGACAUCAAGAAGCUGCGGGACAACGAGGAGCUCAACUCCC
CCAAGAUCCGCGUGUACAACACCGUGAUCAGCUACAUCGAGUCCAACCGGAAGAACAACA
AGCAGACCAUCCACCUGCUGAAGCGCCUCCCCGCCGACGUCCUGAAGAAGACGAUCAAGA
ACACCCUGGACAUCCACAAGAGCAUCACCAUCAACAACCCGAAGGAGCUCACCGUGUCCG
ACACGAACGACCACGCGAAGAACAACGACACCACCUGAGGACUAGUGCAUCACAUUUAAA
AGCAUCUCAGCCUACCAUGAGAAUAAGAGAAAGAAAAUGAAGAUCAAUAGCUUAUUCAUC
UCUUUUUCUUUUUCGUUGGUGUAAAGCCAACACCCUGUCUAAAAAACAUAAAUUUCUUUA
AUCAUUUUGCCUCUUUUCUCUGUGCUUCAAUUAAUAAAAAAUGGAAAGAACCUAGAUCUA
AAAAAAAAAAAAAAAAAAAAAAAAAAAAAAAAAAAAAAAAAAAAAAAAAAAAAAAAAAAA
AAAUGCAUCCCCCCCCCCCCCCCCCCCCCCCCCCCCCCCAAAGGCUCUUUUCAGAGCCAC
CAGAAUU

Fig. 5

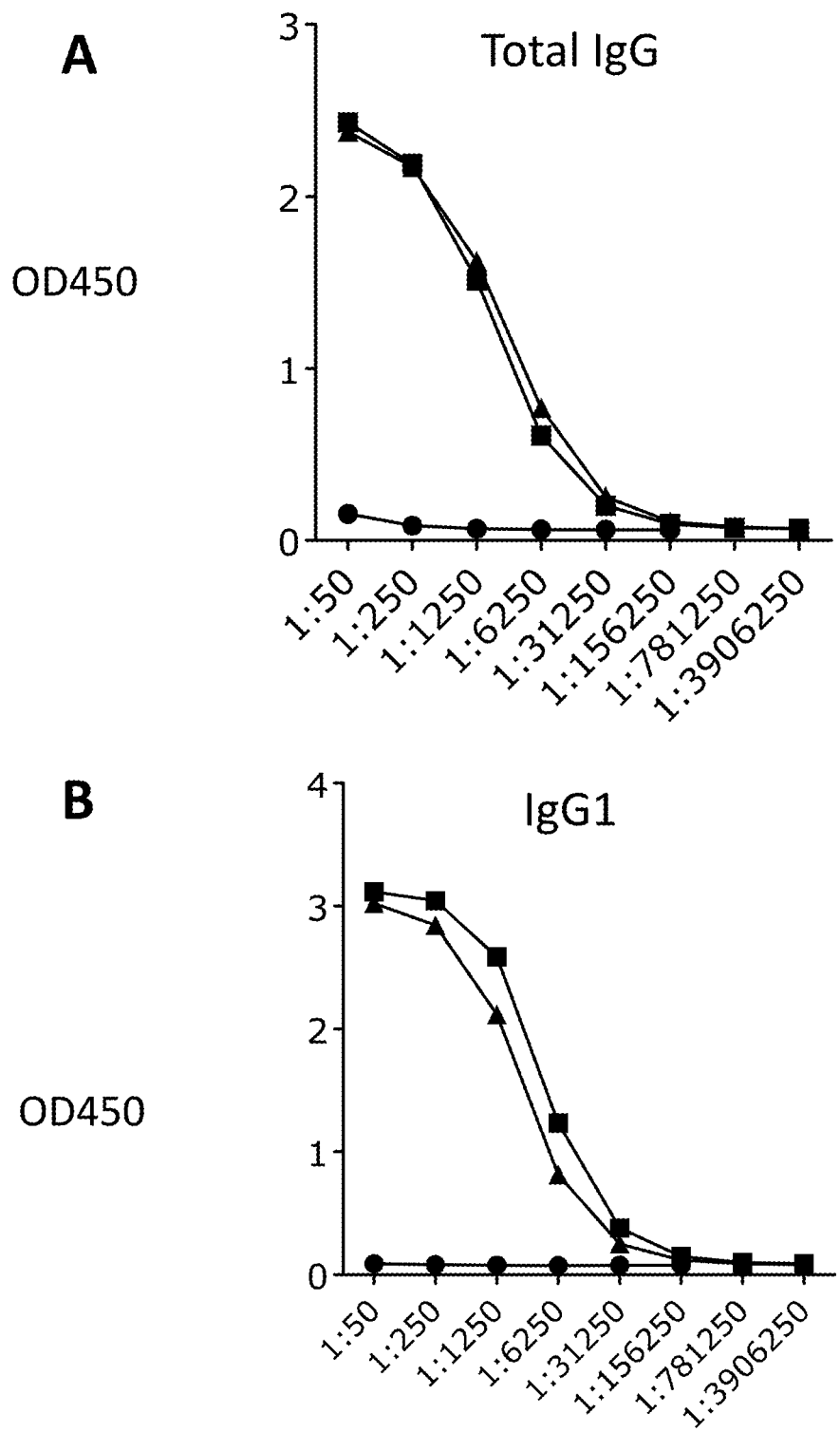
Figs. 6A-B

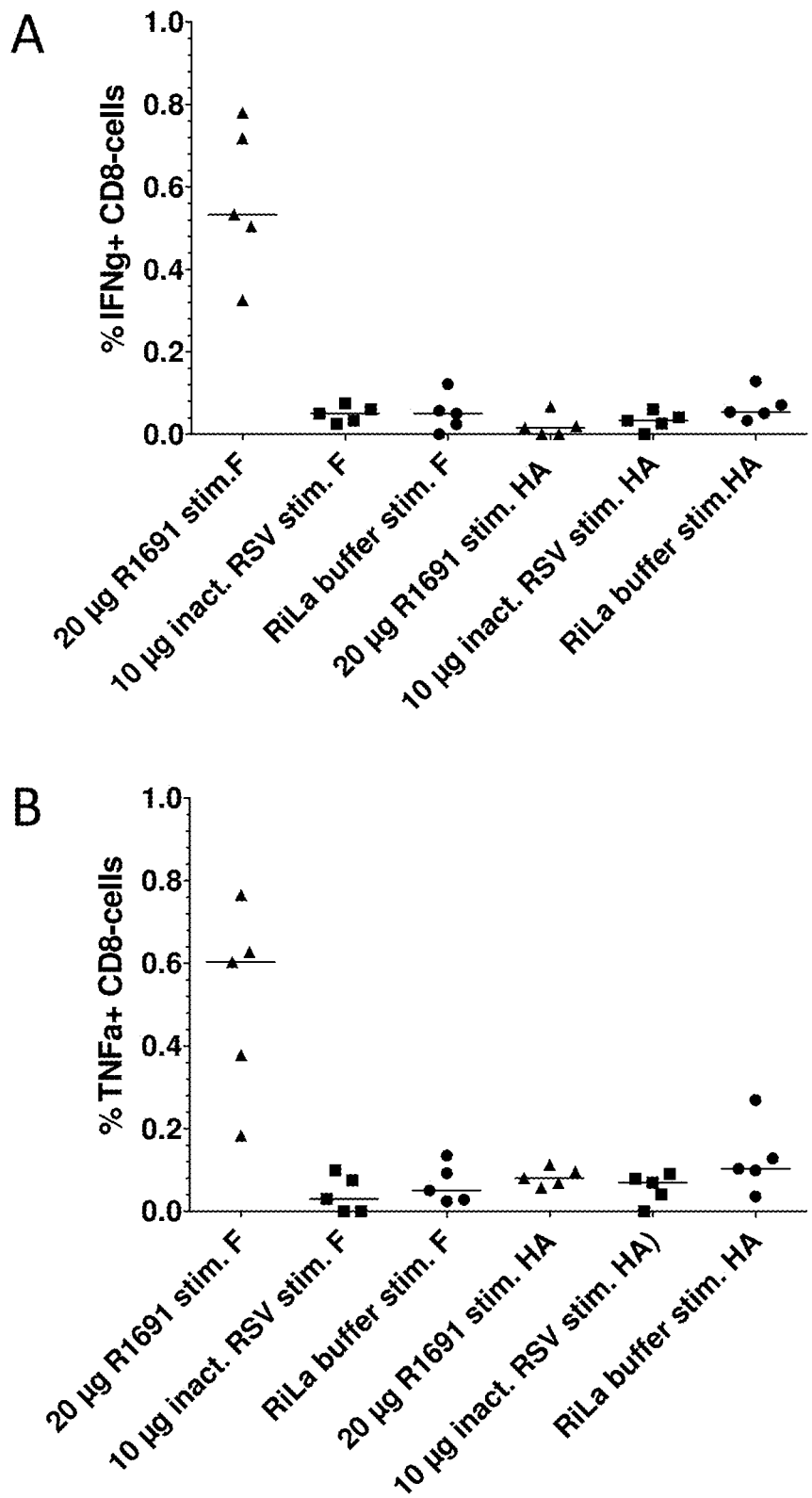
Figs. 8A-B

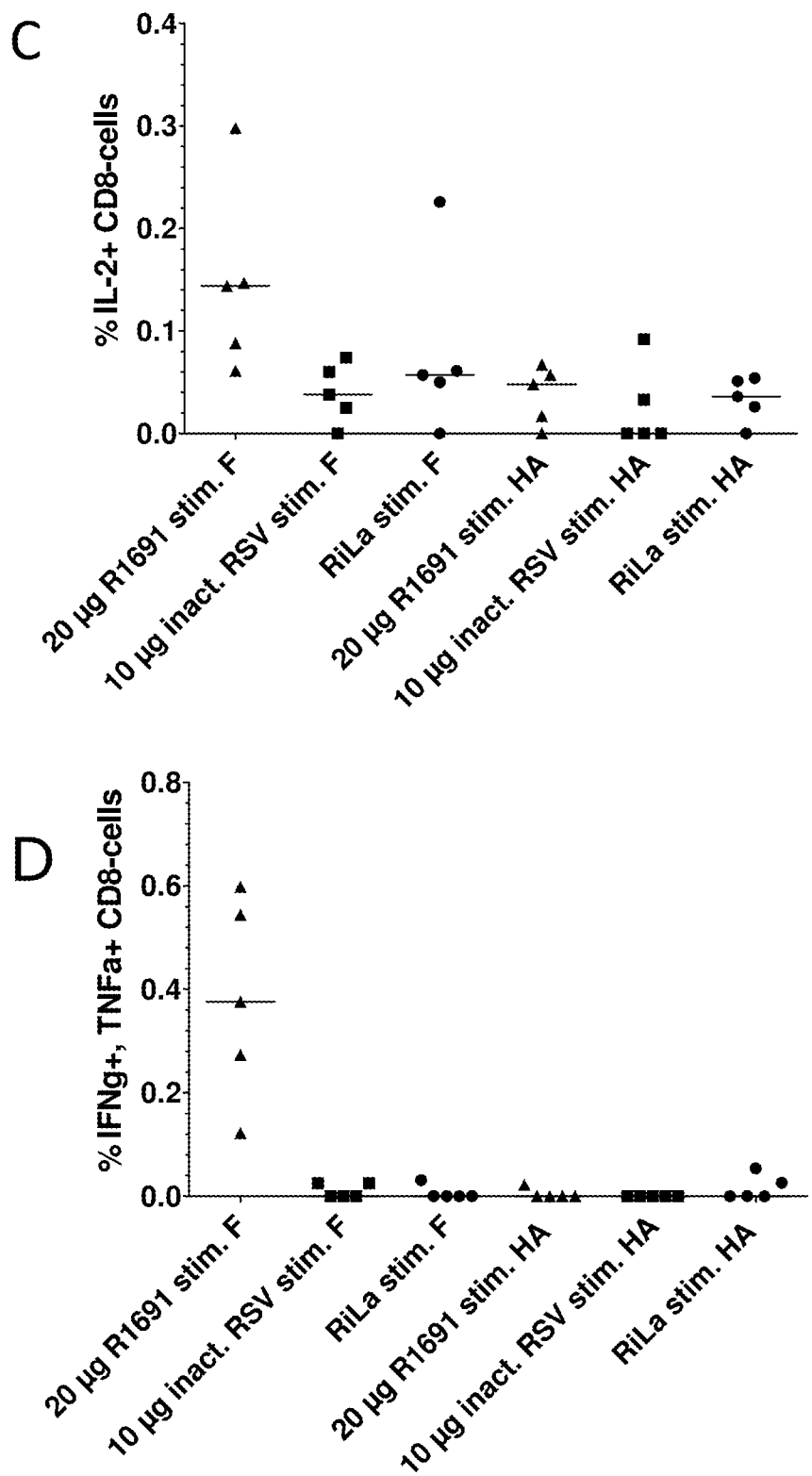
Figs. 8C-D

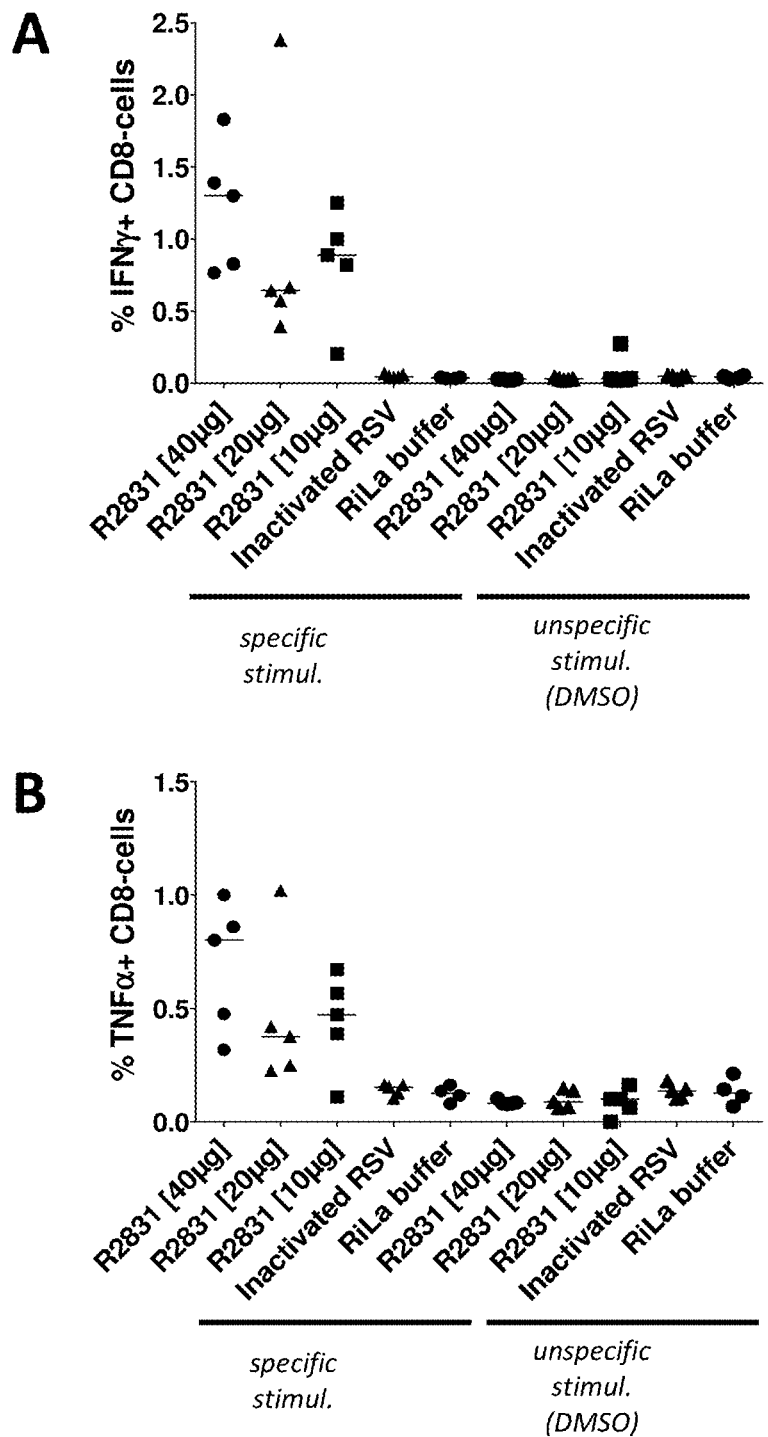
Figs. 9A-B

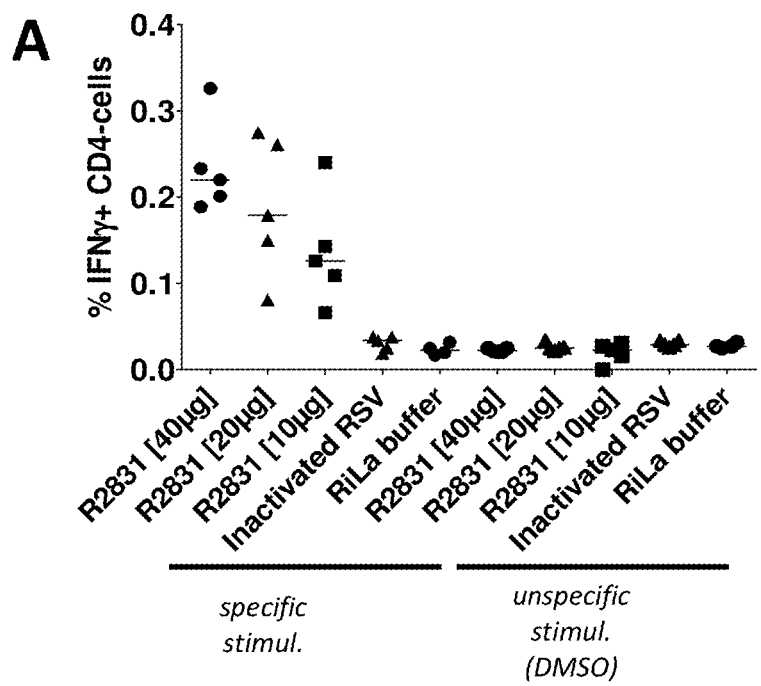
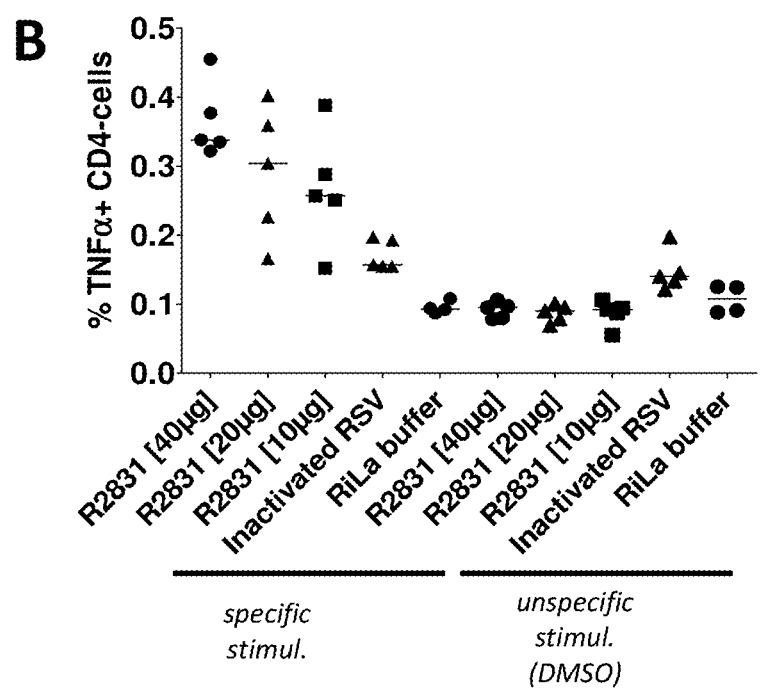
Figs. 10A-B

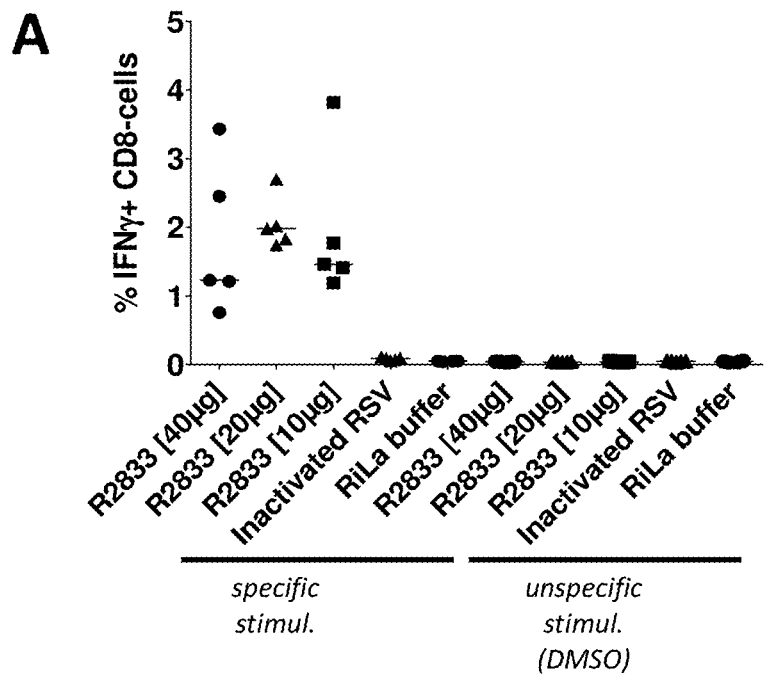
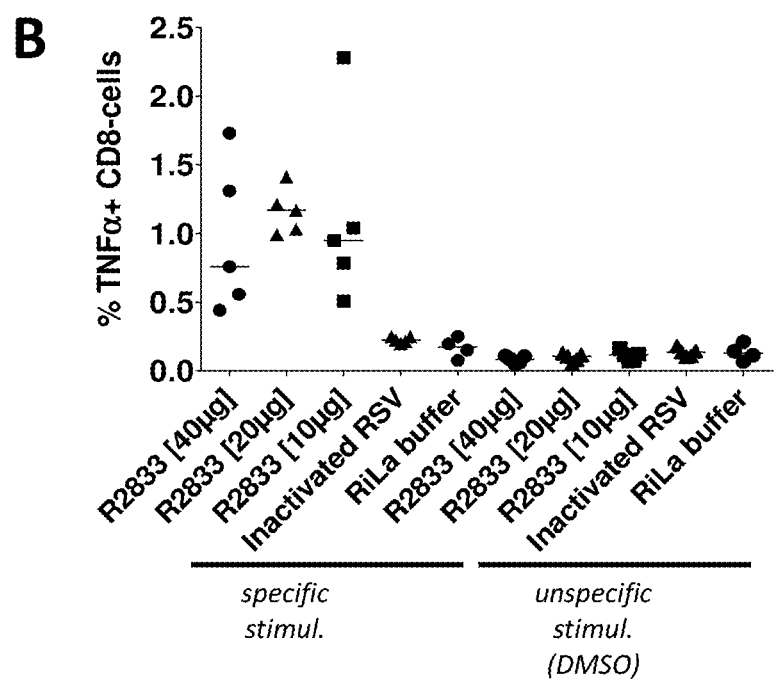
Figs. 11A-B

Figs. 14A-B

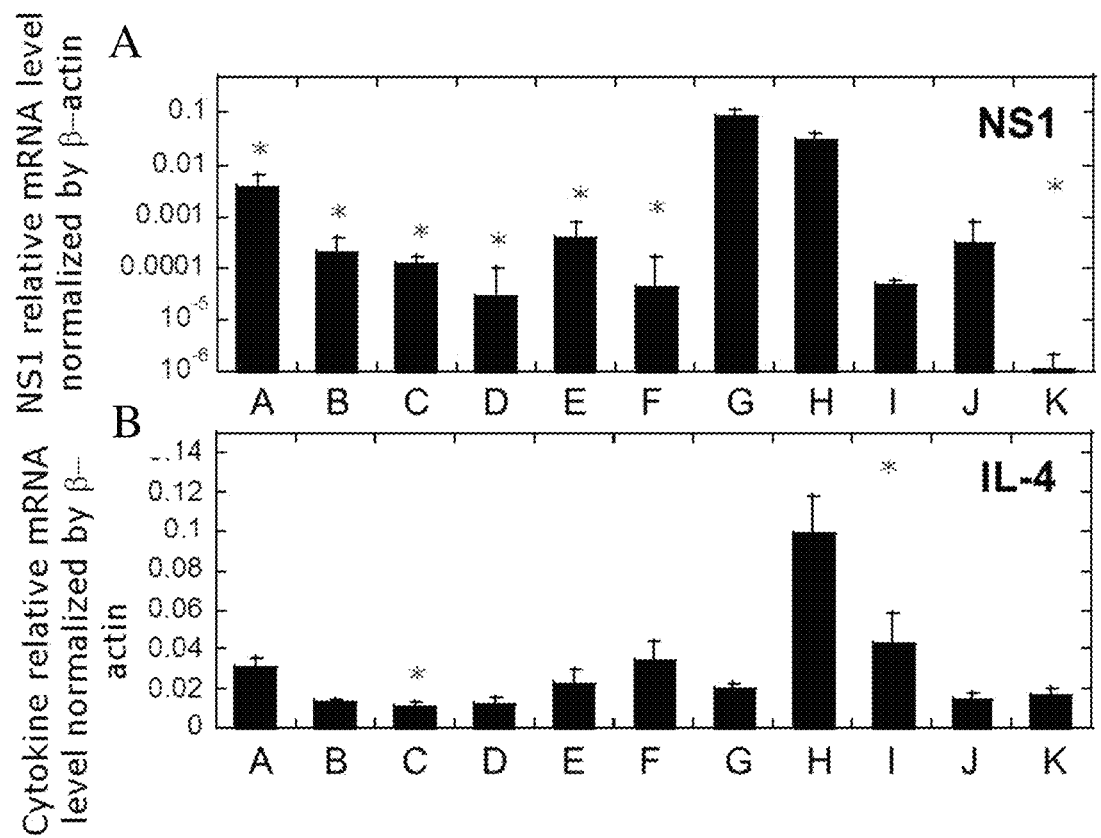
Figs. 16A-B

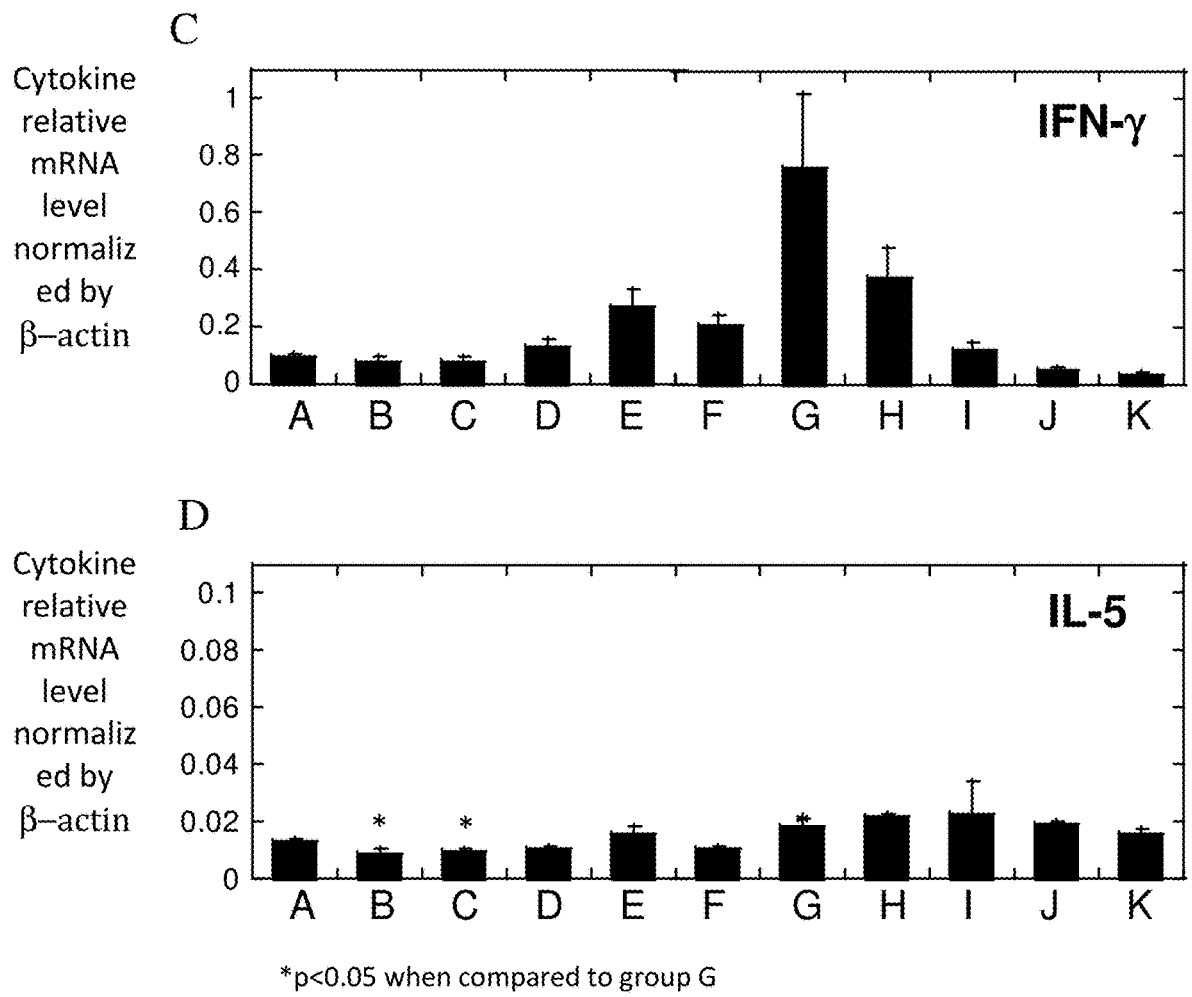
Figs. 16C-D

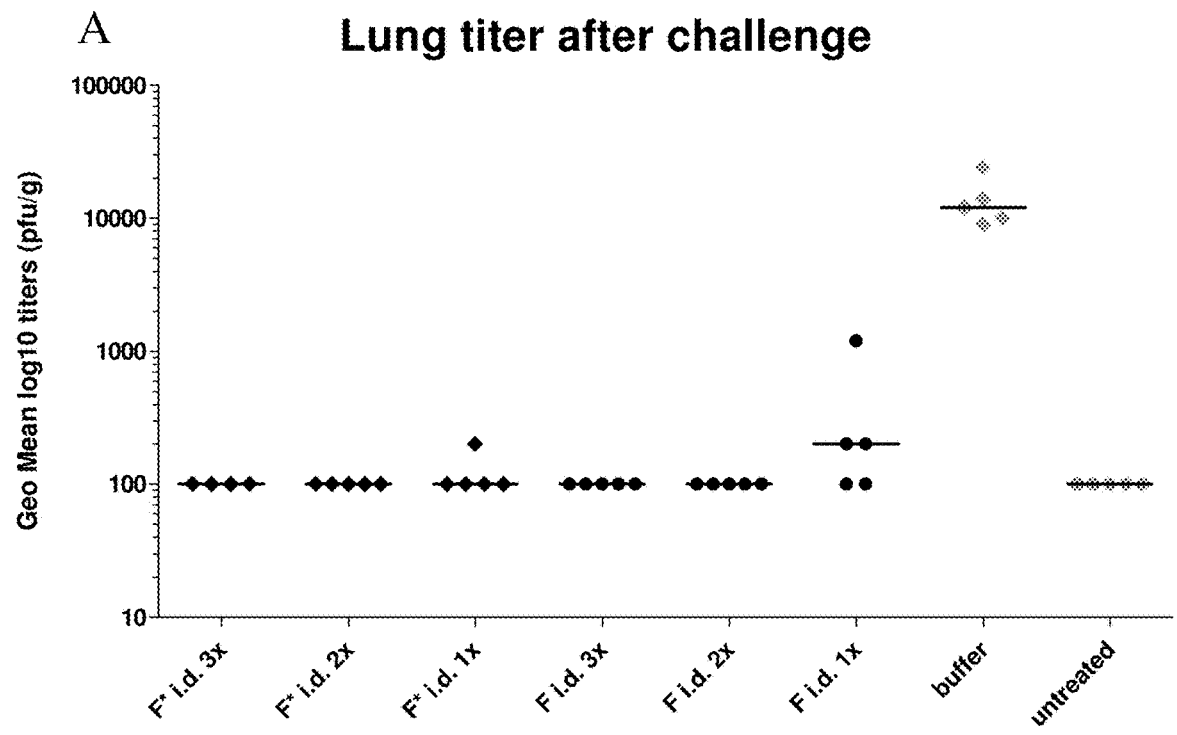
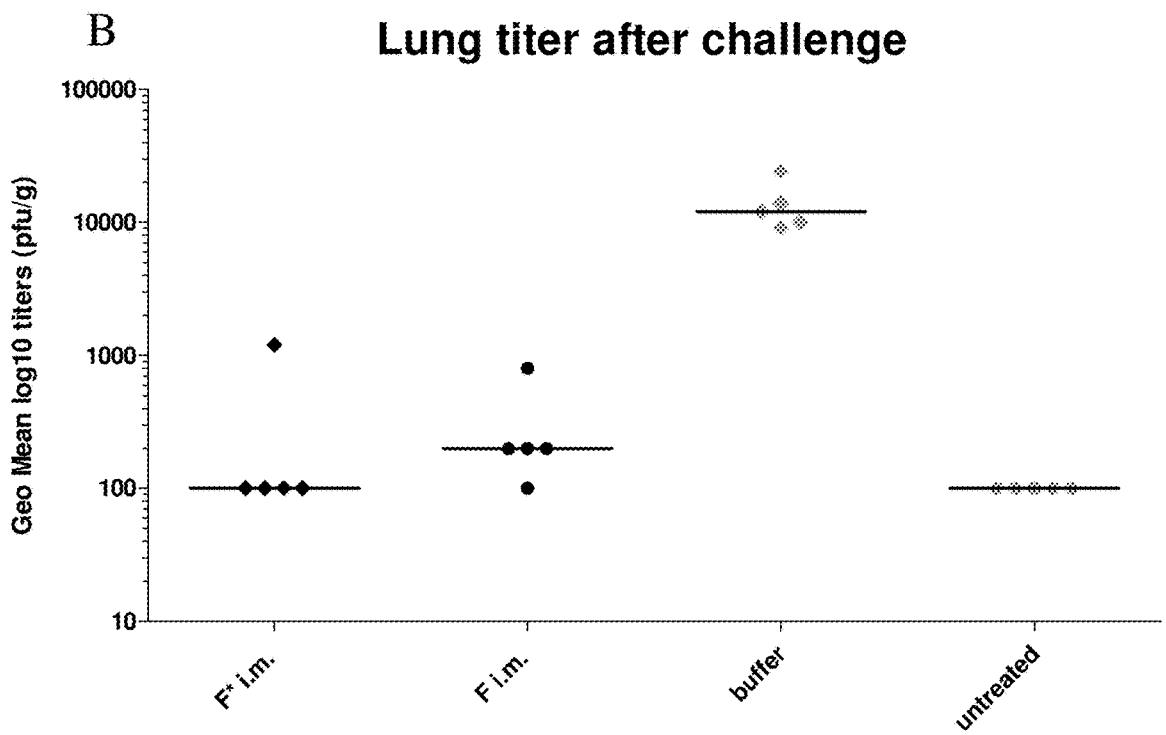
Figs. 17A-B

RESPIRATORY SYNCYTIAL VIRUS (RSV) VACCINE

BACKGROUND OF THE INVENTION

The present application is a continuation of U.S. application Ser. No. 18/348,042, filed Jul. 6, 2023, which is a continuation of U.S. application Ser. No. 17/316,834, filed May 11, 2021, now U.S. Pat. No. 11,739,125, which is a continuation of U.S. application Ser. No. 16/168,747, filed Oct. 23, 2018, now U.S. Pat. No. 11,034,729, which is a continuation of U.S. application Ser. No. 15/488,815, filed Apr. 17, 2017, now U.S. Pat. No. 10,150,797, which is a continuation of U.S. application Ser. No. 15/048,439, filed Feb. 19, 2016, now U.S. Pat. No. 9,688,729, which is a continuation of International Application No. PCT/EP2014/002301, filed Aug. 21, 2014, the entire text of each of the above referenced disclosures being specifically incorporated herein by reference. International Application No. PCT/EP2014/002301 claims priority benefit of European Application No. PCT/EP2013/002518, filed Aug. 21, 2013.

This application contains a Sequence Listing XML, which has been submitted electronically and is hereby incorporated by reference in its entirety. Said Sequence Listing XML, created on Sep. 6, 2023, is named CRVCP0151USC4.xml and is 63,816 bytes in size.

The present invention relates to an mRNA sequence, comprising a coding region, encoding at least one antigenic peptide or protein of Respiratory syncytial virus (RSV) or a fragment, variant or derivative thereof. Additionally the present invention relates to a composition comprising a plurality of mRNA sequences comprising a coding region, encoding at least one antigenic peptide or protein of Respiratory syncytial virus (RSV) or a fragment, variant or derivative thereof.

Furthermore it also discloses the use of the mRNA sequence or the composition comprising a plurality of mRNA sequences for the preparation of a pharmaceutical composition, especially a vaccine, e.g. for use in the prophylaxis or treatment of RSV infections. The present invention further describes a method of treatment or prophylaxis of RSV infections using the mRNA sequence.

The global medical need and economic impact of RSV is very high. It is the most important cause of acute lower respiratory tract infections (ALRIs) that result in hospital visits during infancy and early childhood. For example, in the United States, more than 60% of infants are infected by RSV during their first RSV season, and nearly all have been infected by 2-3 years of age. Approximately 2.1 million US children less than 5 years of age are treated for RSV disease each year: 3% as inpatients, 25% in emergency departments, and 73% in pediatric practices. Globally, among children less than five years of age, RSV causes an estimated 33.8 million ALRIs each year (more than 22% of all ALRIs), resulting in 66 000-199 000 deaths, 99% of which occur in developing countries. RSV is also a common cause of respiratory disease among the elderly, resulting in as many hospitalizations as influenza in a heavily influenza-immunized population. RSV spreads by respiratory droplets and close contact with infected persons or contaminated objects. In temperate climates, there is an annual winter epidemic. Infants are at highest risk for severe RSV disease in their first 6 months, and hospitalization peaks at 2-3 months of age. Preterm birth and cardiopulmonary disease are risk factors for severe RSV disease. RSV infection of infants elicits partially protective immunity, which appears to wane more rapidly than immunity against most other respiratory viruses. Most children infected with RSV during their first year are re-infected the next year, generally with less severe disease. Re-infections continue throughout life, often with upper respiratory tract symptoms, and sometimes with lower respiratory tract or sinus involvement. Recommended treatment of RSV bronchiolitis consists primarily of respiratory support and hydration. No specific anti-viral therapy is recommended. The neutralizing monoclonal antibody Palivizumab is used for prophylaxis of infants at highest risk for severe infection but is too expensive and impractical for universal use. Currently, there is no licensed RSV vaccine, and developing a safe and effective RSV vaccine is a global public health priority.

In a vaccine trial in the 1960s, infants and young children were immunized with a formalin-inactivated whole virion RSV preparation (FIRSV) or an equivalent paramyxovirus preparation (FIPIV). Five percent of the subjects who were immunized with FI-PIV and then naturally infected by RSV during the next RSV season were hospitalized; 80% of those who were immunized with FI-RSV and then infected by RSV were hospitalized, and two children died. This enhancement of an RSV infection due to vaccination is a specific problem for the development of vaccines against RSV infections (reviewed in Shaw et al. Curr Opin Virol. 2013 June; 3(3):332-42. doi: 10.1016/j.coviro.2013.05.003. Epub 2013 May 30.).

Therefore, Respiratory syncytial virus (RSV) infections are the greatest remaining unmet infant vaccine need in developed countries and an important unmet infant vaccine need worldwide. More than 40 years of effort have not yet resulted in a licensed RSV vaccine for humans.

In summary, RSV which belongs to the virus family of Paramyxoviridae, is one of the most contagious pathogens and makes a substantial contribution to severe respiratory tract infections in infants, the elderly and immunocompromised patients.

As mentioned above, currently a humanised monoclonal antibody against the viral surface F protein is the only prophylactic product on the market which is recommended for infants considered at high risk including pre-term infants and infants with chronic lung disease (The IMpact-RSV Study Group. 1998. Palivizumab, a Humanized Respiratory Syncytial Virus Monoclonal Antibody, Reduces Hospitalization From Respiratory Syncytial Virus Infection in High-risk Infants. Pediatrics, 102(3), S.531-537., Tablan et al. 2003. Guidelines for preventing health-care-associated pneumonia, 2003: recommendations of CDC and the Healthcare Infection Control Practices Advisory Committee. MMWR. Recommendations and Reports: Morbidity and Mortality Weekly Report. Recommendations and Reports/Centers for Disease Control, 53(RR-3), S.1-36.).

Recent studies with animal models demonstrated that sufficient amounts of neutralising antibodies targeting RSV F protein limit viral replication leading to a less severe course of disease (Singh, S. R. et al., 2007. Immunogenicity and efficacy of recombinant RSV-F vaccine in a mouse model. Vaccine, 25(33), S.6211-6223., Zhan, X. et al., 2007. Respiratory syncytial virus (RSV) F protein expressed by recombinant Sendai virus elicits B-cell and T-cell responses in cotton rats and confers protection against RSV subtypes A and B. Vaccine, 25(52), S.8782-8793., Vaughan, K., et al., 2005. DNA immunization against respiratory syncytial virus (RSV) in infant rhesus monkeys. Vaccine, 23(22), S.2928-2942).

Moreover, it could be shown that a balanced regulatory and effector T cell function is required for viral clearance and reduction of severity of illness (Liu, J. et al., 2010.

Epitope-specific regulatory CD4 T cells reduce virus-induced illness while preserving CD8 T-cell effector function at the site of infection. Journal of Virology, 84(20), S.10501-10509).

Despite the above mentioned humanised monoclonal antibody, live-attenuated vaccine viruses were developed which elicit a strong immune response, but which are not recommended for use in the specific target groups (infants, children, the elderly and immunocompromised patients). Also, DNA vectors expressing RSV F protein which bears B-cell epitopes were used to induce the production of neutralizing antibodies. In this context, WO 2008/077527 and WO 96/040945 disclose vectors comprising DNA sequences encoding RSV F protein for the use as vaccines. However, the use of DNA as a vaccine may be dangerous due to unwanted insertion into the genome, possibly leading to interruption of functional genes and cancer or the formation of anti-DNA antibodies.

Therefore it is the object of the underlying invention to provide an mRNA sequence coding for antigenic peptides or proteins of Respiratory syncytial virus (RSV) for the use as vaccine for prophylaxis or treatment of RSV infections, particularly in infants, the elderly and immunocompromised patients.

These objects are solved by the subject matter of the attached claims. Particularly, the objects underlying the present invention are solved according to a first aspect by an inventive mRNA sequence comprising a coding region, encoding at least one antigenic peptide or protein of Respiratory syncytial virus (RSV) or a fragment, variant or derivative thereof.

For the sake of clarity and readability the following scientific background information and definitions are provided. Any technical features disclosed thereby can be part of each and every embodiment of the invention. Additional definitions and explanations can be provided in the context of this disclosure.

Immune system: The immune system may protect organisms from infection. If a pathogen breaks through a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts contains so called humoral and cellular components.

Immune response: An immune response may typically either be a specific reaction of the adaptive immune system to a particular antigen (so called specific or adaptive immune response) or an unspecific reaction of the innate immune system (so called unspecific or innate immune response). The invention relates to the core to specific reactions (adaptive immune responses) of the adaptive immune system. Particularly, it relates to adaptive immune responses to infections by viruses like e.g. RSV infections. However, this specific response can be supported by an additional unspecific reaction (innate immune response). Therefore, the invention also relates to a compound for simultaneous stimulation of the innate and the adaptive immune system to evoke an efficient adaptive immune response.

Adaptive immune system: The adaptive immune system is composed of highly specialized, systemic cells and processes that eliminate or prevent pathogenic growth. The adaptive immune response provides the vertebrate immune system with the ability to recognize and remember specific pathogens (to generate immunity), and to mount stronger attacks each time the pathogen is encountered. The system is highly adaptable because of somatic hypermutation (a process of increased frequency of somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of that cell will then inherit genes encoding the same receptor specificity, including the Memory B cells and Memory T cells that are the keys to long-lived specific immunity. Immune network theory is a theory of how the adaptive immune system works, that is based on interactions between the variable regions of the receptors of T cells, B cells and of molecules made by T cells and B cells that have variable regions.

Adaptive immune response: The adaptive immune response is typically understood to be antigen-specific. Antigen specificity allows for the generation of responses that are tailored to specific antigens, pathogens or pathogen-infected cells. The ability to mount these tailored responses is maintained in the body by "memory cells". Should a pathogen infect the body more than once, these specific memory cells are used to quickly eliminate it. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. Cell types that can serve as antigen-presenting cells are inter alia dendritic cells, macrophages, and B cells. Each of these cells has a distinct function in eliciting immune responses. Dendritic cells take up antigens by phagocytosis and macropinocytosis and are stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. Presenting the antigen on MHC molecules leads to activation of T cells which induces their proliferation and differentiation into armed effector T cells. The most important function of effector T cells is the killing of infected cells by $CD8^+$ cytotoxic T cells and the activation of macrophages by Th1 cells which together make up cell-mediated immunity, and the activation of B cells by both Th2 and Th1 cells to produce different classes of antibody, thus driving the humoral immune response. T cells recognize an antigen by their T cell receptors which do not recognize and bind antigen directly, but instead recognize short peptide fragments e.g. of pathogen-derived protein antigens, which are bound to MHC molecules on the surfaces of other cells.

Cellular immunity/cellular immune response: Cellular immunity relates typically to the activation of macrophages, natural killer cells (NK), antigen-specific cytotoxic T-lymphocytes, and the release of various cytokines in response to an antigen. In a more general way, cellular immunity is not related to antibodies but to the activation of cells of the immune system. A cellular immune response is characterized e.g. by activating antigen-specific cytotoxic T-lymphocytes that are able to induce apoptosis in body cells displaying epitopes of an antigen on their surface, such as virus-infected cells, cells with intracellular bacteria, and cancer cells displaying tumor antigens; activating macrophages and natural killer cells, enabling them to destroy pathogens; and stimulating cells to secrete a variety of cytokines that influence the function of other cells involved in adaptive immune responses and innate immune responses.

Humoral immunity/humoral immune response: Humoral immunity refers typically to antibody production and the accessory processes that may accompany it. A humoral immune response may be typically characterized, e.g., by Th2 activation and cytokine production, germinal center formation and isotype switching, affinity maturation and memory cell generation. Humoral immunity also typically may refer to the effector functions of antibodies, which include pathogen and toxin neutralization, classical complement activation, and opsonin promotion of phagocytosis and pathogen elimination.

Innate immune system: The innate immune system, also known as non-specific immune system, comprises the cells and mechanisms that defend the host from infection by other organisms in a non-specific manner. This means that the cells of the innate system recognize and respond to pathogens in a generic way, but unlike the adaptive immune system, it does not confer long-lasting or protective immunity to the host. The innate immune system may be e.g. activated by ligands of pathogen-associated molecular patterns (PAMP) receptors, e.g. Toll-like receptors (TLRs) or other auxiliary substances such as lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent. Typically a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system through a process known as antigen presentation; and/or acting as a physical and chemical barrier to infectious agents.

Adjuvant/adjuvant component: An adjuvant or an adjuvant component in the broadest sense is typically a (e.g. pharmacological or immunological) agent or composition that may modify, e.g. enhance, the efficacy of other agents, such as a drug or vaccine. Conventionally the term refers in the context of the invention to a compound or composition that serves as a carrier or auxiliary substance for immunogens and/or other pharmaceutically active compounds. It is to be interpreted in a broad sense and refers to a broad spectrum of substances that are able to increase the immunogenicity of antigens incorporated into or co-administered with an adjuvant in question. In the context of the present invention an adjuvant will preferably enhance the specific immunogenic effect of the active agents of the present invention. Typically, "adjuvant" or "adjuvant component" has the same meaning and can be used mutually. Adjuvants may be divided, e.g., into immuno potentiators, antigenic delivery systems or even combinations thereof.

The term "adjuvant" is typically understood not to comprise agents which confer immunity by themselves. An adjuvant assists the immune system unspecifically to enhance the antigen-specific immune response by e.g. promoting presentation of an antigen to the immune system or induction of an unspecific innate immune response. Furthermore, an adjuvant may preferably e.g. modulate the antigen-specific immune response by e.g. shifting the dominating Th2-based antigen specific response to a more Th1-based antigen specific response or vice versa. Accordingly, an adjuvant may favourably modulate cytokine expression/secretion, antigen presentation, type of immune response etc.

Immunostimulatory RNA: An immunostimulatory RNA (isRNA) in the context of the invention may typically be a RNA that is able to induce an innate immune response itself. It usually does not have an open reading frame and thus does not provide a peptide-antigen or immunogen but elicits an innate immune response e.g. by binding to a specific kind of Toll-like-receptor (TLR) or other suitable receptors. However, of course also mRNAs having an open reading frame and coding for a peptide/protein (e.g. an antigenic function) may induce an innate immune response.

Antigen: According to the present invention, the term "antigen" refers typically to a substance which may be recognized by the immune system and may be capable of triggering an antigen-specific immune response, e.g. by formation of antibodies or antigen-specific T-cells as part of an adaptive immune response. An antigen may be a protein or peptide. In this context, the first step of an adaptive immune response is the activation of naïve antigen-specific T cells by antigen-presenting cells. This occurs in the lymphoid tissues and organs through which naïve T cells are constantly passing. The three cell types that can serve as antigen-presenting cells are dendritic cells, macrophages, and B cells. Each of these cells has a distinct function in eliciting immune responses. Tissue dendritic cells take up antigens by phagocytosis and macropinocytosis and are stimulated by infection to migrate to the local lymphoid tissue, where they differentiate into mature dendritic cells. Macrophages ingest particulate antigens such as bacteria and are induced by infectious agents to express MHC class II molecules. The unique ability of B cells to bind and internalize soluble protein antigens via their receptors may be important to induce T cells. By presenting the antigen on MHC molecules leads to activation of T cells which induces their proliferation and differentiation into armed effector T cells. The most important function of effector T cells is the killing of infected cells by $CD8^+$ cytotoxic T cells and the activation of macrophages by TH1 cells which together make up cell-mediated immunity, and the activation of B cells by both TH2 and TH1 cells to produce different classes of antibody, thus driving the humoral immune response. T cells recognize an antigen by their T cell receptors which does not recognize and bind antigen directly, but instead recognize short peptide fragments e.g. of pathogens' protein antigens, which are bound to MHC molecules on the surfaces of other cells. T cells fall into two major classes that have different effector functions. The two classes are distinguished by the expression of the cell-surface proteins CD4 and CD8. These two types of T cells differ in the class of MHC molecule that they recognize. There are two classes of MHC molecules—MHC class I and MHC class II molecules—which differ in their structure and expression pattern on tissues of the body. CD4$^+$ T cells bind to a MHC class II molecule and CD8$^+$ T cells to a MHC class I molecule. MHC class I and MHC class II molecules have distinct distributions among cells that reflect the different effector functions of the T cells that recognize them. MHC class I molecules present peptides of cytosolic and nuclear origin e.g. from pathogens, commonly viruses, to CD8$^+$ T cells, which differentiate into cytotoxic T cells that are specialized to kill any cell that they specifically recognize. Almost all cells express MHC class I molecules, although the level of constitutive expression varies from one cell type to the next. But not only pathogenic peptides from viruses are presented by MHC class I molecules, also self-antigens like tumour antigens are presented by them. MHC class I molecules bind peptides from proteins degraded in the cytosol and transported in the endoplasmic reticulum. The CD8$^+$ T cells that recognize MHC class I:peptide complexes at the surface of infected cells are specialized to kill any cells displaying foreign peptides and so rid the body of cells infected with viruses and other cytosolic pathogens. The main function of CD4$^+$ T cells (CD4$^+$ helper T cells) that recognize MHC class II molecules is to activate other effector cells of the immune system. Thus MHC class II molecules are normally found on B lymphocytes, dendritic cells, and macrophages, cells that participate in immune responses, but not on other tissue cells. Macrophages, for example, are activated to kill the intravesicular pathogens they harbour, and B cells to secrete immunoglobulins against foreign molecules. MHC class II molecules are prevented from binding to peptides in the endoplasmic reticulum and thus MHC class II molecules bind peptides from proteins which are degraded in endosomes. They can capture peptides from pathogens that have entered the vesicular system of macrophages, or from antigens internalized by immature dendritic cells or the immunoglobulin receptors of B cells. Pathogens that accumulate in large numbers inside macrophage and dendritic cell vesicles tend to stimulate the differentiation of TH1 cells, whereas extracellular antigens tend to stimulate the production of TH2 cells. TH1 cells activate the microbicidal properties of macrophages and induce B cells to make IgG antibodies that are very effective of opsonising extracellular pathogens for ingestion by phagocytic cells, whereas TH2 cells initiate the humoral response by activating naïve B cells to secrete IgM, and induce the production of weakly opsonising antibodies such as IgG1 and IgG3 (mouse) and IgG2 and IgG4 (human) as well as IgA and IgE (mouse and human).

Epitope (also called "antigen determinant"): T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule.

B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

Vaccine: A vaccine is typically understood to be a prophylactic or therapeutic material providing at least one antigen or antigenic function. The antigen or antigenic function may stimulate the body's adaptive immune system to provide an adaptive immune response.

Antigen-providing mRNA: An antigen-providing mRNA in the context of the invention may typically be an mRNA, having at least one open reading frame that can be translated by a cell or an organism provided with that mRNA. The product of this translation is a peptide or protein that may act as an antigen, preferably as an immunogen. The product may also be a fusion protein composed of more than one immunogen, e.g. a fusion protein that consist of two or more epitopes, peptides or proteins derived from the same or different virus-proteins, wherein the epitopes, peptides or proteins may be linked by linker sequences.

Bi-/multicistronic mRNA: mRNA, that typically may have two (bicistronic) or more (multicistronic) open reading frames (ORF). An open reading frame in this context is a sequence of several nucleotide triplets (codons) that can be translated into a peptide or protein. Translation of such a mRNA yields two (bicistronic) or more (multicistronic) distinct translation products (provided the ORFs are not identical). For expression in eukaryotes such mRNAs may for example comprise an internal ribosomal entry site (IRES) sequence.

5'-CAP-Structure: A 5'-CAP is typically a modified nucleotide, particularly a guanine nucleotide, added to the 5' end of an mRNA-molecule. Preferably, the 5'-CAP is added using a 5'-5'-triphosphate linkage (also named m7GpppN). Further examples of 5'-CAP structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety. These modified 5'-CAP structures may be used in the context of the present invention to modify the inventive mRNA sequence. Further modified 5'-CAP structures which may be used in the context of the present invention are CAP1 (methylation of the ribose of the adjacent nucleotide of m7GpppN), CAP2 (methylation of the ribose of the $2^{nd}$ nucleotide downstream of the m7GpppN), CAP3 (methylation of the ribose of the $3^{rd}$ nucleotide downstream of the m7GpppN), CAP4 (methylation of the ribose of the 4$^{th}$ nucleotide downstream of the m7GpppN), ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

Fragments of proteins: "Fragments" of proteins or peptides in the context of the present invention may, typically, comprise a sequence of a protein or peptide as defined herein, which is, with regard to its amino acid sequence (or its encoded nucleic acid molecule), N-terminally and/or C-terminally truncated compared to the amino acid sequence of the original (native) protein (or its encoded nucleic acid molecule). Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide.

Fragments of proteins or peptides in the context of the present invention may furthermore comprise a sequence of a protein or peptide as defined herein, which has a length of for example at least 5 amino acids, preferably a length of at least 6 amino acids, preferably at least 7 amino acids, more preferably at least 8 amino acids, even more preferably at least 9 amino acids; even more preferably at least 10 amino acids; even more preferably at least 11 amino acids; even more preferably at least 12 amino acids; even more preferably at least 13 amino acids; even more preferably at least 14 amino acids; even more preferably at least 15 amino acids; even more preferably at least 16 amino acids; even more preferably at least 17 amino acids; even more preferably at least 18 amino acids; even more preferably at least 19 amino acids; even more preferably at least 20 amino acids; even more preferably at least 25 amino acids; even more preferably at least 30 amino acids; even more preferably at least 35 amino acids; even more preferably at least 50 amino acids; or most preferably at least 100 amino acids. For example such fragment may have a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form. Fragments of proteins or peptides may comprise at least one epitope of those proteins or peptides. Furthermore also domains of a protein, like the extracellular domain, the intracellular domain or the transmembrane domain and shortened or truncated versions of a protein may be understood to comprise a fragment of a protein.

Variants of proteins: "Variants" of proteins or peptides as defined in the context of the present invention may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native protein, e.g. its specific antigenic property. "Variants" of proteins or peptides as defined in the context of the present invention may comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

A "variant" of a protein or peptide may have at least 70%, 75%, 80%, 85%, 90%, 95%, 98% or 99% amino acid identity over a stretch of 10, 20, 30, 50, 75 or 100 amino acids of such protein or peptide.

Furthermore, variants of proteins or peptides as defined herein, which may be encoded by a nucleic acid molecule, may also comprise those sequences, wherein nucleotides of the encoding nucleic acid sequence are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

Identity of a sequence: In order to determine the percentage to which two sequences are identical, e.g. nucleic acid sequences or amino acid sequences as defined herein, preferably the amino acid sequences encoded by a nucleic acid sequence of the polymeric carrier as defined herein or the amino acid sequences themselves, the sequences can be aligned in order to be subsequently compared to one another. Therefore, e.g. a position of a first sequence may be compared with the corresponding position of the second sequence. If a position in the first sequence is occupied by the same component (residue) as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program.

Derivative of a protein or peptide: A derivative of a peptide or protein is typically understood to be a molecule that is derived from another molecule, such as said peptide or protein. A "derivative" of a peptide or protein also encompasses fusions comprising a peptide or protein used in the present invention. For example, the fusion comprises a label, such as, for example, an epitope, e.g., a FLAG epitope or a V5 epitope. For example, the epitope is a FLAG epitope. Such a tag is useful for, for example, purifying the fusion protein.

Monocistronic mRNA: A monocistronic mRNA may typically be an mRNA, that encodes only one open reading frame. An open reading frame in this context is a sequence of several nucleotide triplets (codons) that can be translated into a peptide or protein.

Nucleic acid: The term nucleic acid means any DNA- or RNA-molecule and is used synonymous with polynucleotide. Wherever herein reference is made to a nucleic acid or nucleic acid sequence encoding a particular protein and/or peptide, said nucleic acid or nucleic acid sequence, respectively, preferably also comprises regulatory sequences allowing in a suitable host, e.g. a human being, its expression, i.e. transcription and/or translation of the nucleic acid sequence encoding the particular protein or peptide.

Peptide: A peptide is a polymer of amino acid monomers. Usually the monomers are linked by peptide bonds. The term "peptide" does not limit the length of the polymer chain of amino acids. In some embodiments of the present invention a peptide may for example contain less than 50 monomer units. Longer peptides are also called polypeptides, typically having 50 to 600 monomeric units, more specifically 50 to 300 monomeric units.

Pharmaceutically effective amount: A pharmaceutically effective amount in the context of the invention is typically understood to be an amount that is sufficient to induce an immune response.

Protein: A protein typically consists of one or more peptides and/or polypeptides folded into 3-dimensional form, facilitating a biological function.

Poly (C) sequence: A poly-(C)-sequence is typically a long sequence of cytosine nucleotides, typically about 10 to about 200 cytosine nucleotides, preferably about 10 to about 100 cytosine nucleotides, more preferably about 10 to about 70 cytosine nucleotides or even more preferably about 20 to about 50 or even about 20 to about 30 cytosine nucleotides. A poly(C) sequence may preferably be located 3' of the coding region comprised by a nucleic acid.

Poly-A-tail: A poly-A-tail also called "3'-poly(A) tail" is typically a long sequence of adenosine nucleotides of up to about 400 adenosine nucleotides, e.g. from about 25 to about 400, preferably from about 50 to about 400, more preferably from about 50 to about 300, even more preferably from about 50 to about 250, most preferably from about 60 to about 250 adenosine nucleotides, added to the 3' end of a RNA.

Stabilized nucleic acid: A stabilized nucleic acid, typically, exhibits a modification increasing resistance to in vivo degradation (e.g. degradation by an exo- or endo-nuclease) and/or ex vivo degradation (e.g. by the manufacturing process prior to vaccine administration, e.g. in the course of the preparation of the vaccine solution to be administered). Stabilization of RNA can, e.g., be achieved by providing a 5'-CAP-Structure, a Poly-A-Tail, or any other UTR-modification. It can also be achieved by backbone-modification or modification of the G/C-content of the nucleic acid. Various other methods are known in the art and conceivable in the context of the invention.

Carrier/polymeric carrier: A carrier in the context of the invention may typically be a compound that facilitates transport and/or complexation of another compound. Said carrier may form a complex with said other compound. A polymeric carrier is a carrier that is formed of a polymer.

Cationic component: The term "cationic component" typically refers to a charged molecule, which is positively charged (cation) at a pH value of typically about 1 to 9, preferably of a pH value of or below 9 (e.g. 5 to 9), of or below 8 (e.g. 5 to 8), of or below 7 (e.g. 5 to 7), most preferably at physiological pH values, e.g. about 7.3 to 7.4. Accordingly, a cationic peptide, protein or polymer according to the present invention is positively charged under physiological conditions, particularly under physiological salt conditions of the cell in vivo. A cationic peptide or protein preferably contains a larger number of cationic amino acids, e.g. a larger number of Arg, His, Lys or Orn than other amino acid residues (in particular more cationic amino acids than anionic amino acid residues like Asp or Glu) or contains blocks predominantly formed by cationic amino acid residues. The definition "cationic" may also refer to "polycationic" components.

Vehicle: An agent, e.g. a carrier, that may typically be used within a pharmaceutical composition or vaccine for facilitating administering of the components of the pharmaceutical composition or vaccine to an individual.

3'-untranslated region (3'UTR): A 3'UTR is typically the part of an mRNA which is located between the protein coding region (i.e. the open reading frame) and the poly(A) sequence of the mRNA. A 3'UTR of the mRNA is not translated into an amino acid sequence. The 3'UTR sequence is generally encoded by the gene which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5'-Capping, splicing the pre-mature mRNA to excise optional introns and modifications of the 3'-end, such as polyadenylation of the 3'-end of the pre-mature mRNA and optional endo- or exonuclease cleavages etc. In the context of the present invention, a 3'UTR corresponds to the sequence of a mature mRNA which is located 3' to the stop codon of the protein coding region, preferably immediately 3' to the stop codon of the protein coding region, and which extends to the 5'-side of the poly(A) sequence, preferably to the nucleotide immediately 5' to the poly(A) sequence. The term "corresponds to" means that the 3'UTR sequence may be an RNA sequence, such as in the mRNA sequence used for defining the 3'UTR sequence, or a DNA sequence which corresponds to such RNA sequence. In the context of the present invention, the term "a 3'UTR of a gene", such as "a 3'UTR of an albumin gene", is the sequence which corresponds to the 3'UTR of the mature mRNA derived from this gene, i.e. the mRNA obtained by transcription of the gene and maturation of the pre-mature mRNA. The term "3'UTR of a gene" encompasses the DNA sequence and the RNA sequence of the 3'UTR.

5'-untranslated region (5'UTR): A 5'-UTR is typically understood to be a particular section of messenger RNA (mRNA). It is located 5' of the open reading frame of the mRNA. Typically, the 5'UTR starts with the transcriptional start site and ends one nucleotide before the start codon of the open reading frame. The 5'-UTR may comprise elements for controlling gene expression, also called regulatory elements. Such regulatory elements may be, for example, ribosomal binding sites or a 5'-Terminal Oligopyrimidine Tract. The 5'UTR may be posttranscriptionally modified, for example by addition of a 5'-CAP. In the context of the present invention, a 5'UTR corresponds to the sequence of a mature mRNA which is located between the 5'-CAP and the start codon. Preferably, the 5'UTR corresponds to the sequence which extends from a nucleotide located 3' to the 5'-CAP, preferably from the nucleotide located immediately 3' to the 5'-CAP, to a nucleotide located 5' to the start codon of the protein coding region, preferably to the nucleotide located immediately 5' to the start codon of the protein coding region. The nucleotide located immediately 3' to the 5'-CAP of a mature mRNA typically corresponds to the transcriptional start site. The term "corresponds to" means that the 5'UTR sequence may be an RNA sequence, such as in the mRNA sequence used for defining the 5'UTR sequence, or a DNA sequence which corresponds to such RNA sequence. In the context of the present invention, the term "a 5'UTR of a gene", such as "a 5'UTR of a TOP gene", is the sequence which corresponds to the 5'UTR of the mature mRNA derived from this gene, i.e. the mRNA obtained by transcription of the gene and maturation of the pre-mature mRNA. The term "5'UTR of a gene" encompasses the DNA sequence and the RNA sequence of the 5'UTR.

5' Terminal Oligopyrimidine Tract (TOP): The 5' terminal oligopyrimidine tract (TOP) is typically a stretch of pyrimidine nucleotides located at the 5' terminal region of a nucleic acid molecule, such as the 5' terminal region of certain mRNA molecules or the 5' terminal region of a functional entity, e.g. the transcribed region, of certain genes. The sequence starts with a cytidine, which usually corresponds to the transcriptional start site, and is followed by a stretch of usually about 3 to 30 pyrimidine nucleotides. For example, the TOP may comprise 3, 4, 5, 6, 7, 8, 9, 10, 11, 12, 13, 14, 15, 16, 17, 18, 19, 20, 21, 22, 23, 24, 25, 26, 27, 28, 29, 30 or even more nucleotides. The pyrimidine stretch and thus the 5' TOP ends one nucleotide 5' to the first purine nucleotide located downstream of the TOP. Messenger RNA that contains a 5' terminal oligopyrimidine tract is often referred to as TOP mRNA. Accordingly, genes that provide such messenger RNAs are referred to as TOP genes. TOP sequences have, for example, been found in genes and mRNAs encoding peptide elongation factors and ribosomal proteins.

TOP motif: In the context of the present invention, a TOP motif is a nucleic acid sequence which corresponds to a 5'TOP as defined above. Thus, a TOP motif in the context of the present invention is preferably a stretch of pyrimidine nucleotides having a length of 3-30 nucleotides. Preferably, the TOP-motif consists of at least 3 pyrimidine nucleotides, preferably at least 4 pyrimidine nucleotides, preferably at least 5 pyrimidine nucleotides, more preferably at least 6 nucleotides, more preferably at least 7 nucleotides, most preferably at least 8 pyrimidine nucleotides, wherein the stretch of pyrimidine nucleotides preferably starts at its 5' end with a cytosine nucleotide. In TOP genes and TOP mRNAs, the TOP-motif preferably starts at its 5' end with the transcriptional start site and ends one nucleotide 5' to the first purin residue in said gene or mRNA. A TOP motif in the sense of the present invention is preferably located at the 5' end of a sequence which represents a 5'UTR or at the 5' end of a sequence which codes for a 5'UTR. Thus, preferably, a stretch of 3 or more pyrimidine nucleotides is called "TOP motif" in the sense of the present invention if this stretch is located at the 5'end of a respective sequence, such as the inventive mRNA, the 5'UTR element of the inventive mRNA, or the nucleic acid sequence which is derived from the 5'UTR of a TOP gene as described herein. In other words, a stretch of 3 or more pyrimidine nucleotides which is not located at the 5'-end of a 5'UTR or a 5'UTR element but anywhere within a 5'UTR or a 5'UTR element is preferably not referred to as "TOP motif".

TOP gene: TOP genes are typically characterised by the presence of a 5' terminal oligopyrimidine tract. Furthermore, most TOP genes are characterized by a growth-associated translational regulation. However, also TOP genes with a tissue specific translational regulation are known. As defined above, the 5'UTR of a TOP gene corresponds to the sequence of a 5'UTR of a mature mRNA derived from a TOP gene, which preferably extends from the nucleotide located 3' to the 5'-CAP to the nucleotide located 5' to the start codon. A 5'UTR of a TOP gene typically does not comprise any start codons, preferably no upstream AUGs (uAUGs) or upstream open reading frames (uORFs). Therein, upstream AUGs and upstream open reading frames are typically understood to be AUGs and open reading frames that occur 5' of the start codon (AUG) of the open reading frame that should be translated. The 5'UTRs of TOP genes are generally rather short. The lengths of 5'UTRs of TOP genes may vary between 20 nucleotides up to 500 nucleotides, and are typically less than about 200 nucleotides, preferably less than about 150 nucleotides, more preferably less than about 100 nucleotides. Exemplary 5'UTRs of TOP genes in the sense of the present invention are the nucleic acid sequences extending from the nucleotide at position 5 to the nucleotide located immediately 5' to the start codon (e.g. the ATG) in the sequences according to SEQ ID Nos. 1-1363, SEQ ID NO. 1395, SEQ ID NO. 1421 and SEQ ID NO. 14221-1363 of the patent application PCT/EP2012/002448WO2013/143700 or homologs or variants thereof, whose disclosure is incorporated herewith by reference. In this context a particularly preferred fragment of a 5'UTR of a TOP gene is a 5'UTR of a TOP gene lacking the 5'TOP motif. The term '5'UTR of a TOP gene' preferably refers to the 5'UTR of a naturally occurring TOP gene.

Fragment of a nucleic acid sequence, particularly an mRNA: A fragment of a nucleic acid sequence consists of a continuous stretch of nucleotides corresponding to a continuous stretch of nucleotides in the full-length nucleic acid sequence which is the basis for the nucleic acid sequence of the fragment, which represents at least 20%, preferably at least 30%, more preferably at least 40%, more preferably at least 50%, even more preferably at least 60%, even more preferably at least 70%, even more preferably at least 80%, and most preferably at least 90% of the full-length nucleic acid sequence. Such a fragment, in the sense of the present invention, is preferably a functional fragment of the full-length nucleic acid sequence.

Variant of a nucleic acid sequence, particularly an mRNA: A variant of a nucleic acid sequence refers to a variant of nucleic acid sequences which forms the basis of a nucleic acid sequence. For example, a variant nucleic acid sequence may exhibit one or more nucleotide deletions, insertions, additions and/or substitutions compared to the nucleic acid sequence from which the variant is derived. Preferably, a variant of a nucleic acid sequence is at least 40%, preferably at least 50%, more preferably at least 60%, more preferably at least 70%, even more preferably at least 80%, even more preferably at least 90%, most preferably at least 95% identical to the nucleic acid sequence the variant is derived from.

Preferably, the variant is a functional variant. A "variant" of a nucleic acid sequence may have at least 70%, 75%, 80%, 85%, 90%, 95%, 98% or 99% nucleotide identity over a stretch of 10, 20, 30, 50, 75 or 100 nucleotide of such nucleic acid sequence.

Homolog of a nucleic acid sequence: The term "homolog" of a nucleic acid sequence refers to sequences of other species than the particular sequence. It is particular preferred that the nucleic acid sequence is of human origin and therefore it is preferred that the homolog is a homolog of a human nucleic acid sequence.

Jet injection: The term "jet injection", as used herein, refers to a needle-free injection method, wherein a fluid containing at least one inventive mRNA sequence and, optionally, further suitable excipients is forced through an orifice, thus generating an ultra-fine liquid stream of high pressure that is capable of penetrating mammalian skin and, depending on the injection settings, subcutaneous tissue or muscle tissue. In principle, the liquid stream forms a hole in the skin, through which the liquid stream is pushed into the target tissue. Preferably, jet injection is used for intradermal, subcutaneous or intramuscular injection of the mRNA sequence according to the invention. In a preferred embodiment, jet injection is used for intramuscular injection of the inventive mRNA. In a further preferred embodiment, jet injection is used for intradermal injection of the inventive mRNa.

The present invention is based on the surprising finding of the present inventors that an mRNA sequence comprising a coding region, encoding at least one antigenic peptide or protein of Respiratory syncytial virus (RSV) induces antigen-specific immune responses and therefore prevent or at least minimize Respiratory syncytial virus (RSV) infections. It was very surprising for the inventors that the inventive mRNA sequence induces at least the same immune responses than vaccines based on inactivated RSV which consists of the whole virus. Even more surprisingly the inventive mRNA sequence coding for an antigenic protein of RSV induced antigen-specific CD8+-T cells in contrast to a vaccine based on an inactivated RSV. Additionally, in a cotton rat RSV challenge model, the virus titers in the nose and in the lung of mRNA vaccinated animals were much lower compared to animals vaccinated with vaccines based on an inactivated RSV virus. With regard to safety the inventors could show that the mRNA-based RSV vaccine showed no hints for vaccine-mediated disease enhancement, in terms of lung pathology, compared to a vaccine based on formalin-inactivated virus. Furthermore, it has surprisingly been found by the inventors that already one single vaccination with the inventive mRNA sequence was sufficient for eliciting an immune response against the administered antigen(s). Specifically, it has been found that one single administration, preferably by intradermal or intramuscular injection, of the inventive mRNA is highly efficient in reducing viral titers in the lung after challenge with RSV virus.

In summary, the inventive mRNA sequence comprising a coding region encoding at least one antigenic peptide or protein of Respiratory syncytial virus (RSV) could provide an effective and safe vaccine, particularly for infants, the elderly and immunocompromised patients.

In this context it is particularly preferred that the inventive mRNA sequence comprises a coding region, encoding at least one antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) or a fragment, variant or derivative thereof.

The coding region of the inventive mRNA sequence according to the first aspect of the present invention may occur as a mono-, bi-, or even multicistronic mRNA, i.e. an mRNA sequence which carries the coding sequences of one, two or more proteins or peptides. Such coding sequences in bi-, or even multicistronic mRNAs may be separated by at least one internal ribosome entry site (IRES) sequence, e.g. as described herein or by signal peptides which induce the cleavage of the resulting polypeptide which comprises several proteins or peptides.

According to the first aspect of the present invention, the inventive mRNA sequence comprises a coding region, encoding at least one antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) or a fragment, variant or derivative thereof. In a particularly preferred embodiment of the first aspect of the invention, the inventive mRNA sequence comprises a coding region, encoding at least one antigenic peptide or protein derived from the fusion protein F, the nucleoprotein N, or the M2-1 protein of Respiratory syncytial virus (RSV) or a fragment, variant or derivative thereof.

In this context, the amino acid sequence of the at least one antigenic peptide or protein may be selected from any peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of any RSV isolate or from any synthetically engineered RSV peptide or protein or from a fragment, variant or derivative thereof.

In a particularly preferred embodiment, the full-length protein of the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) is encoded by the coding region comprised in the inventive mRNA.

In this context, the full-length protein from the fusion protein F and the nucleoprotein N are particularly preferred. Furthermore a mutant of the F protein with a deletion of the cytoplasmic tail is particularly preferred. An example of such a deletion mutant is the RSV-Fdel 554-574 long protein according to (Oomens et al. 2006. J. Virol. 80(21):10465-77).

In a further particularly preferred embodiment, a fragment comprising at least one epitope of the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) is encoded by the coding region comprised in the inventive mRNA.

Particularly preferred are the amino acid sequences of the RSV strain long (ATCC VR-26) according to the NCBI accession No. AY911262:

Fusion protein F of the RSV strain ATCC VR-26 long:
Amino acid sequence according to SEQ ID No. 1:
MELPILKANA ITTILAAVTF CFASSQNITE EFYQSTCSAV SKGYLSALRT GWYTSVITIE

LSNIKENKCN GTDAKVKLIN QELDKYKNAV TELQLLMQST TAANNRARRE

LPRFMNYTLN NTKKTNVTLS KKRKRRFLGF LLGVGSAIAS GIAVSKVLHL

EGEVNKIKSA LLSTNKAVVS LSNGVSVLTS KVLDLKNYID KQLLPIVNKQ

SCRISNIETV IEFQQKNNRL LEITREFSVN AGVTTPVSTY MLTNSELLSL INDMPITNDQ

KKLMSNNVQI VRQQSYSIMS IIKEEVLAYV VQLPLYGVID TPCWKLHTSP

LCTTNTKEGS NICLTRTDRG WYCDNAGSVS FFPQAETCKV QSNRVFCDTM

NSLTLPSEVN LCNVDIFNPK YDCKIMTSKT DVSSSVITSL GAIVSCYGKT

KCTASNKNRG IIKTFSNGCD YVSNKGVDTV SVGNTLYYVN KQEGKSLYVK

GEPIINFYDP LVFPSDEFDA SISQVNEKIN QSLAFIRKSD ELLHHVNAGK STTNIMITTI

IIVIIVILLS LIAVGLLLYC KARSTPVTLS KDQLSGINNI AFSN

Glycoprotein G of the RSV strain ATCC VR-26 long:
Amino acid sequence according to SEQ ID No. 2:
MSKNKDQRTA KTLEKTWDTL NHLLFISSGL YKLNLKSIAQ ITLSILAMII STSLIITAII

FIASANHKVT LTTAIIQDAT SQIKNTTPTY LTQDPQLGIS FSNLSEITSQ TTTILASTTP

GVKSNLQPTT VKTKNTTTTQ TQPSKPTTKQ RQNKPPNKPN NDFHFEVFNF

VPCSICSNNP TCWAICKRIP NKKPGKKTTT KPTKKPTFKT TKKDLKPQTT

KPKEVPTTKP TEEPTINTTK TNITTTLLTN NTTGNPKLTS QMETFHSTSS EGNLSPSQVS

TTSEHPSQPS SPPNTTRQ

Short hydrophobic protein SH of the RSV strain ATCC VR-26 long:
Amino acid sequence according to SEQ ID No. 3:
MENTSITIEF SSKFWPYFTL IHMITTIISL LIIISIMTAI LNKLCEYNVF HNKTFELPRA

RVNT

Matrix protein M of the RSV strain ATCC VR-26 long:
Amino acid sequence according to SEQ ID No. 4:
METYVNKLHE GSTYTAAVQY NVLEKDDDPA SLTIWVPMFQ SSMPADLLIK

ELANVNILVK QISTPKGPSL RVMINSRSAL LAQMPSKFTI CANVSLDERS

KLAYDVTTPC EIKACSLTCL KSKNMLTTVK DLTMKTLNPT HDIIALCEFE

NIVTSKKVII PTYLRSISVR NKDLNTLENI TTTEFKNAIT NAKIIPYSGL LLVITVTDNK

GAFKYIKPQS QFIVDLGAYL EKESIYYVTT NWKHTATRFA IKPMED

Nucleoprotein N of the RSV strain ATCC VR-26 long:
Amino acid sequence according to SEQ ID No. 5:
MALSKVKLND TLNKDQLLSS SKYTIQRSTG DSIDTPNYDV QKHINKLCGM

LLITEDANHK

FTGLIGMLYA MSRLGREDTI KILRDAGYHV KANGVDVTTH RQDINGKEMK

FEVLTLASLT

TEIQINIEIE SRKSYKKMLK EMGEVAPEYR HDSPDCGMII LCIAALVITK

LAAGDRSGLT

AVIRRANNVL KNEMKRYKGL LPKDIANSFY EVFEKHPHFI DVFVHFGIAQ

SSTRGGSRVE

GIFAGLFMNA YGAGQVMLRW GVLAKSVKNI MLGHASVQAE MEQVVEVYEY

AQKLGGEAGF

-continued

```
YHILNNPKAS LLSLTQFPHF SSVVLGNAAG LGIMGEYRGT PRNQDLYDAA

KAYAEQLKEN

GVINYSVLDL TAEELEAIKH QLNPKDNDVE L

Large polymerase L of the RSV strain ATCC VR-26 long:
Amino acid sequence according to SEQ ID No. 6:
MDPIINGNSA NVYLTDSYLK GVISFSECNA LGSYIFNGPY LKNDYTNLIS

RQNPLIEHMN

LKKLNITQSL ISKYHKGEIK LEEPTYFQSL LMTYKSMTSL EQIATTNLLK KIIRRAIEIS

DVKVYAILNK LGLKEKDKIK SNNGQDEDNS VITTIIKDDI LSAVKDNQSH

LKADKNHSTK

QKDTIKTTLL KKLMCSMQHP PSWLIHWFNL YTKLNNILTQ YRSNEVKNHG

FILIDNQTLS

GFQFILNQYG CIVYHKELKR ITVTTYNQFL TWKDISLSRL NVCLITWISN

CLNTLNKSLG

LRCGFNNVIL TQLFLYGDCI LKLFHNEGFY IIKEVEGFIM SLILNITEED QFRKRFYNSM

LNNITDAANK AQKNLLSRVC HTLLDKTVSD NIINGRWIIL LSKFLKLIKL

AGDNNLNNLS

ELYFLFRIFG HPMVDERQAM DAVKVNCNET KFYLLSSLSM LRGAFIYRII

KGFVNNYNRW

PTLRNAIVLP LRWLTYYKLN TYPSLLELTE RDLIVLSGLR FYREFRLPKK

VDLEMIINDK

AISPPKNLIW TSFPRNYMPS HIQNYIEHEK LKFSESDKSR RVLEYYLRDN

KFNECDLYNC

VVNQSYLNNP NHVVSLTGKE RELSVGRMFA MQPGMFRQVQ ILAEKMIAEN

ILQFFPESLT

RYGDLELQKI LELKAGISNK SNRYNDNYNN YISKCSIITD LSKFNQAFRY

ETSCICSDVL

DELHGVQSLF SWLHLTIPHV TIICTYRHAP PYIRDHIVDL NNVDEQSGLY

RYHMGGIEGW

CQKLWTIEAI SLLDLISLKG KFSITALING DNQSIDISKP VRLMEGQTHA

QADYLLALNS

LKLLYKEYAG IGHKLKGTET YISRDMQFMS KTIQHNGVYY PASIKKVLRV

GPWINTILDD

FKVSLESIGS LTQELEYRGE SLLCSLIFRN VWLYNQIALQ LKNHALCNNK

LYLDILKVLK

HLKTFFNLDN IDTALTLYMN LPMLFGGGDP NLLYRSFYRR TPDFLTEAIV

HSVFILSYYT

NHDLKDKLQD LSDDRLNKFL TCIITFDKNP NAEFVTLMRD PQALGSERQA

KITSEINRLA

VTEVLSTAPN KIFSKSAQHY TTTEIDLNDI MQNIEPTYPH GLRVVYESLP

FYKAEKIVNL
```

ISGTKSITNI LEKTSAIDLT DIDRATEMMR KNITLLIRIL PLDCNRDKRE ILSMENLSIT

ELSKYVRERS WSLSNIVGVT SPSIMYTMDI KYTTSTIASG IIIEKYNVNS LTRGERGPTK

PWVGSSTQEK KTMPVYNRQV LTKKQRDQID LLAKLDWVYA SIDNKDEFME

ELSIGTLGLT

YEKAKKLFPQ YLSVNYLHRL TVSSRPCEFP ASIPAYRTTN YHFDTSPINR

ILTEKYGDED

IDIVFQNCIS FGLSLMSVVE QFTNVCPNRI ILIPKLNEIH LMKPPIFTGD VDIHKLKQVI

QKQHMFLPDK ISLTQYVELF LSNKTLKSGS HVNSNLILAH KISDYFHNTY

ILSTNLAGHW

ILIIQLMKDS KGIFEKDWGE GYITDHMFIN LKVFFNAYKT YLLCFHKGYG

KAKLECDMNT

SDLLCVLELI DSSYWKSMSK VFLEQKVIKY ILSQDASLHR VKGCHSFKLW

FLKRLNVAEF

TVCPWVVNID YHPTHMKAIL TYIDLVRMGL INIDRIHIKN KHKENDEFYT

SNLFYINYNF

SDNTHLLTKH IRIANSELEN NYNKLYHPTP ETLENILANP IKSNDKKTLN

DYCIGKNVDS

IMLPLLSNKK LVKSSAMIRT NYSKQDLYNL FPTVVIDRII DHSGNTAKSN

QLYTTTSHQI

SLVHNSTSLY CMLPWHHINR FNFVFSSTGC KISIEYILKD LKIKDPNCIA FIGEGAGNLL

LRTVVELHPD IRYIYRSLKD CNDHSLPIEF LRLYNGHINI DYGENLTIPA

TDATNNIHWS

YLHIKFAEPI SLFVCDAELP VTVNWSKIII EWSKHVRKCK YCSSVNKCTL

IVKYHAQDDI

DFKLDNITIL KTYVCLGSKL KGSEVYLVLT IGPANIFPVF NVVQNAKLIL

SRTKNFIMPK

KADKESIDAN IKSLIPFLCY PITKKGINTA LSKLKSVVSG DILSYSIAGR NEVESNKLIN

HKHMNILKWF NHVLNFRSTE LNYNHLYMVE STYPYLSELL NSLTTNELKK

LIKITGSLLY

NFHNE

M2-1 protein of the RSV strain ATCC VR-26 long:
Amino acid sequence according to SEQ ID No. 7:
MSRRNPCKFE IRGHCLNGKR CHESHNYFEW PPHALLVRQN FMLNRILKSM

DKSIDTLSEI

SGAAELDRTE EYALGVVGVL ESYIGSINNI TKQSACVAMS KLLTELNSDD

IKKLRDNEEL

NSPKIRVYNT VISYIESNRK NNKQTIHLLK RLPADVLKKT IKNTLDIHKS ITINNPKELT

VSDTNDHAKN NDTT

M2-2 protein of the RSV strain ATCC VR-26 long:
Amino acid sequence according to SEQ ID No. 8:
MTMPKIMILP DKYPCSITSI LITSRCRVTM YNRKNTLYFN QNNPNNHMYS

PNQTFNEIHW

TSQDLIDTIQ NFLQHLGVIE DIYTIYILVS

Phosphoprotein P of the RSV strain ATCC VR-26 long:
Amino acid sequence according to SEQ ID No. 9:
MEKFAPEFHG EDANNRATKF LESIKGKFTS PKDPKKKDSI ISVNSIDIEV TKESPITSNS

TIINPTNETD DNAGNKPNYQ RKPLVSFKED PIPSDNPFSK LYKETIETFD NNEEESSYSY

EEINDQTNDN ITARLDRIDE KLSEILGMLH TLVVASAGPT SARDGIRDAM

VGLREEMIEK

IRTEALMTND RLEAMARLRN EESEKMAKDT SDEVSLNPTS EKLNNLLEGN

DSDNDLSLED

F

Non-structural protein NS1 of the RSV strain ATCC VR-26 long:
Amino acid sequence according to SEQ ID No. 10:
MGSNSLSMIK VRLQNLFDND EVALLKITCY TDKLIHLTNA LAKAVIHTIK

LNGIVFVHVI

TSSDICPNNN IVVKSNFTTM PVLQNGGYIW EMMELTHCSQ PNGLIDDNCE

IKFSKKLSDS

TMTNYMNQLS ELLGFDLNP

Non-structural protein NS2 of the RSV strain ATCC VR-26 long:
Amino acid sequence according to SEQ ID No. 11:
MDTTHNDTTP QRLMITDMRP LSLETTITSL TRDIITHRFI YLINHECIVR KLDERQATFT

FLVNYEMKLL HKVGSTKYKK YTEYNTKYGT FPMPIFINHD GFLECIGIKP

TKHTPIIYKY

DLNP

In the context of the invention, additionally to the here disclosed amino acid sequences according to SEQ ID Nos. 1-11, also amino acid sequences of different Respiratory syncytial virus (RSV) isolates can be used according to the invention and are incorporated herewith. These Respiratory syncytial virus (RSV) isolates show preferably an identity of at least 70%, more preferably of at least 80% and most preferably of at least 90% with the amino acid sequences according to SEQ ID Nos. 1-11.

Furthermore, in this context the coding region encoding at least one antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) or a fragment, variant or derivative thereof, may be selected from any nucleic acid sequence comprising a coding region derived from any Respiratory syncytial virus (RSV) isolate or a fragment or variant thereof.

Particularly preferred are the wild type mRNA sequences of the coding regions of the RSV strain long (ATCC VR-26) according to the NCBI accession No. AY911262:

mRNA coding for the fusion protein F of the RSV strain ATCC VR-26 long:
mRNA sequence according to SEQ ID No. 12:
auggaguugccaauccucaaagcaaaugcaauuaccacaauccucgcugcagucacauuuugcuuugcuucuagucaaaacau cacugaagaauuuuaucaaucaacaugcagugcaguuagcaaaggcuaucuuagugcucuaagaacugguugguauacuagu guuauaacuauagaauuaaguaauaucaaggaaaauaaguguaauggaacagaugcuaaqguaaaauugauaaaccaagaauu agauaaauauaaaaaugcuguaacagaauugcaguugcucaugcaaagcacaacagcagcaaacaaucgagccagaagagaacu accaagguuuaugaauuauacacucaacaauaccaaaaaaaccaauguaacauuaagcaagaaaaggaaaagaagauuucuugg uuuuugguuaggguguuggaucugcaaucgccaguggcauugcuguaucuaagguccugcacuuagaaggagaagugaacaa gaucaaaagugcucuacuauccacaaacaaggccguagucagcuuaucaaauggaguuagugucuuaaccagcaaaguguuag accucaaaaacuauauagauaaacaauuguuaccuauugugaauaagcaaagcugcagaauaucaaauauagaaacugugaua gaguuccaacaaaagaacaacagacuacuagagauuaccagggaauuuaguguuaaugcagguguaacuacaccuguaagcac uuacauguuaacuaauagugaauuauugucauuaaucaaugauaugccuauaacaaaugaucagaaaaaguuaaugccaaca auguucaaauaguuagacagcaaaguuacucuaucauguccauaauaaaagaggaagucuuagcauauguaguacaauuacca -continued cuauauggugugauagauacaccuuguuggaaauuacacacaucccccucuauguacaaccaacacaaaagaagggucaaacau cuguuuaacaagaacugacagaggauggacgugacaaugcaggaucaguaucuuucuucccacaagcugaaacauguaaa guucaaucgaaucgaguauuuugugacacaaugaacaguuuaacauuaccaagugaaguaaaucucugcaauguugacauau ucaaucccaaauaugauuguaaaauuaugacuucaaaaacgaugoaagcagcuccguuaucacaucucuaggagccauugug ucaugcuauggcaaaacuaaaugacagcauccauaaaaaucguggaaucauaaagacauuuucuaacggguguggauuaug uaucaaauaaagggguggacacugugucuguagguaacacauuauauuaugoaaauaagcaagaaggcaaaagucucuaugu aaaaggugaaccaauaauaaauuucuaugacccauuaguauucccoucugaugaauuugaugcaucaauaucucaagucaaug agaagauuaaccagaguuuagcauuuauucguaaauccgaugaauuauuacaucaaugaaaugcugguaaaucaaccacaaau aucaugauaacuacuauaauuauagugauuauaguaauauuguuaucauuaauugcuguuggacugcuccuauacuguaagg ccagaagcacaccagucacacuaagcaaggaucaacugaggguauaaauaauauugcauuuaguaacuga mRNA coding for the glycoprotein G of the RSV strain ATCC VR-26 long:
mRNA sequence according to SEQ ID No. 13:
augucccaaaaacaaggaccaacgcaccgcuaagcacuagaaaagaccugggacacucucaaucauuuauuauucauaucaucg ggcuuauauaaguuaaaucuuaaaucuauagcacaaaucacauuauccauucuggcaaugauaaucucaacuucacuuauaau uacagccaucauauucauagccucggcaaaccacaaagucacacuaacaacugcaaucauacaagaugcaacaagccagaucaa gaacacaaccccaacauaccucacucaggauccucagcuuggaaucagcuucuccaaucugucgaaauuacaucacaaaccac caccauacuagcuucaacaacaccaggagucaagucaaaccugcaacccacaacagucaagacuaaaaacacaacaacaacccaa acacaacccagcaagcccacuacaaaacaacgccaaaacaaaccaccaaacaaacccaauaaugauuuucacuucgaaguguuua acuuuguacccugcagcauaugcagcaacaauccaaccugcugggcuaucugcaaaagaauaccaaacaaaaaaccaggaaaga aaaccaccaccaagccuacaaaaaaaccaaccuucaagacaaccaaaaaagaucucaaaccucaaaccacuaaaccaaaggaagua cccaccaccaagcccacagaagagccaaccaucaacaccaccaaaacaaacaucacaacuacacugcucaccaacaacaccacagg aaauccaaaacucacaagucaaauggaaaccuuccacucaaccuccuccgaaggcaaucuaagcccuucucaagucuccacaac auccgagcacccaucacaaccocucaucuccacccaacacaacacgccaguag mRNA coding for the Short hydrophobic protein SH of the RSV strain ATCC VR-26 long:
mRNA sequence according to SEQ ID No. 14:
auggaaaaauacauccauaacaauagaauucucaagcaaauucuggccuuacuuuacacuaauacacaugaucacaacaauaauc ucuuugcuaaucauaaucucccaucaugacugcaauacuaaacaaacuuugugaauauaacguauuccauaacaaaaccuuuga guuaccaagagcucgagucaacacauag mRNA coding for the matrixprotein M of the RSV strain ATCC VR-26 long:
mRNA sequence according to SEQ ID No. 15:
auggaaacauacgugaacaagcuucacgaaggcuccacauacacagcugcuguucaauacaaugoccuagaaaaagacgauga cccugcaucacuuacaauaugggugcccauguucuaaucaucuaugccagcagauuuacuuauaaaagaacuagcuaaugoca acauacuagugaaacaaauauccacacccaagggaccuucacuaagagucaugauaaacucaagaagugcauugcuagcacaaa ugcccagcaaauuuaccauaugugcuaaugugouccuuggaugaaagaagcaaacuggcauaugauguaaccacaccougugaa aucaaggcauguagucuaacaugccuaaaaucaaaaaauauguuaacuacaguuaaagaucucacuaugaagacacucaaccoc acacaugauauuauugcuuuaugugaauuugaaaacauaguaacaucaaaaaagucauaauaccaacauaccuagauccau cagugucagaaauaaagaucugaacacacuugaaaauauaacaaccacugaauuuaaaaaugccaucacaaaugoaaaaaucau cccuuacucaggauuacuauuagucaucacagugacugoaacaaaggagcauucaaauacauaaagccgcaaagucaauuca uaguagaucuuggagcuuaccuagaaaaagaaaguauauauuauguuaccacaaauuggaagcacacagcuacacgauuugca aucaaacccauggaagauuaa mRNA coding for the nucleoprotein N of the RSV strain ATCC VR-26 long:
mRNA sequence according to SEQ ID No. 16:
auggcucuuagcaaagucaaguugaaugauacacucaacaaagaucaacuucugucaucuagcaaauacaccauccaacggag cacaggagauaguauugauacuccuaauuaugaugugcagaaacacaucaauaaguuauguggcauguauuaaucacagaa gaugcuaaucauaaauucacugggguuaauagguauguuauaugcuaugucuagguuaggaagagaagacaccauaaaaauac -continued ucagagaugcgggauaucaugaaaagcaaauggaguagauguaacaacacaucgucaagacaucaaugggaaagaaaugaaa uuugaaguguuaacauuggcaagcuuaacaacugaaauucaaaucaacauuggagauagaaucuagaaaauccuacaaaaaaau gcuaaaagaaaugggagaggaagcuccagaauacaggcaugauucuccugauugugggaugauaauauuauguauagcagca uuaguaauaaccaaauuggcagcagggaugaugaucuggucuuacagccgugauuaggagagcuaauaauguccuaaaaaaug aaaugaaacguuacaaaggcuuacuacccaaggauauagccaacagcuucuaugaaguguuugaaaaacaucccacuuuaua gauguuuugugucauuuuggauagcacaaucuuccaccagagguggcagaagauugaagggauuuugcaggauuguuu augaaugccuauggugcagggcaaguaaugcuacgguggggagucuuagcaaaaucaguuaaaaauauuauguuaggacaug cuagugugcaagcagaaauggaacaaguuguugagguuuaugaauaugcccaaaaauugggguggagaagcaggauucuacca uauauugaacaacccaaaagcaucauuauuaucuuugacucaauuuccucacuuuuccagguaguauuaggcaaugcugcu ggccuaggcauaaaugggagaguacagaggucaccgaggaaucaagaucuauaugaugcagcaaaggcauaugcugaacaacu caaagaaaauggugugauuaacuacaguguauuagacuugacagcagaagaacuagaggcuaucaaacaucagcuuaauccaa aagauaaugaugauagagcuuuga mRNA coding for the Large polymerase L of the RSV strain ATCC VR-26 long:
mRNA sequence according to SEQ ID No. 17:
auggaucccauuauuaauggaaauucugcuaauguuuaucuaaccgauaguauuuaaaagguguuaucucuuucucagagu guaaugcuuuaggaaguuacauauucaauggccuuaucucaaaaaugauuauaccaacuuaauuaguagacaaaauccauua auagaacacaugaaucaaagaaacuaaauauaacacaguccuuaauaucuaaguaucauaaaggugaaauaaaaauuagaaga gccuacuuauuucaguauuacuuaugacauacaagagaugaccucguuggaacagauugcuaccacuaauuuacuuaaa aagauaauaagaagagcuauagaaauaaguagaugauugcaaagucuaugcuauauugaauaaacuagggcuuaaagaaaaggacaa gauuaaauccaacaauggacaggaugaagacaacucaguuauuacgaccauaaucaaagaugauauacuuucagcuguuaagg auaaucaaucucaucuuaaagcagacaaaaaucacucuacaaaacaaaagacacaaucaaaacaacacucuugaagaaauuaau guguucaaugcagcauccuccaucaugguuaauacauugguuuaauuuauacacaaaauuaaacaacauauuaacacaguauc gaucaaaugagguuaaaaaccauggguuuauauugauagauaaucaaacucuuaguggauuucaauuuauuuugaaucaaua ugguuguauaguuuaucauaaggaacucaaaagaauuacugugacaaccuauaaucaauucuugacauggaaagauauuagc cuuaguagauuaaaugcuuguguuaauuacauggauuaguaacugcuugaacacauuaaauaaaagcuuaggcuuaagaugcg gauucaauaauguuaucuugacacaacuauuccuuuauggugauuguauacuaaagcuauuucacaaugaggggguucuacau aauaaaagagguagagggauuauuaugucucuaauuuuaaaauauaacagaagaagaucaauucagaaacgauuuuauaau aguaugcucaacaacaucacagaugcugcuaauaaagcucagaaaaaucugcuaucaagaguaugucauacauuauuagauaa gacaguauccgauaauauaauaaauggcagauggauaauucuauuaaguaaguuccuaaauuaauuaagcuugcaggugac aauaaccuuaacaaucugaugugaacuauauuuuuuguucagaauauuuggacacccaauggagaugaaagacaagccaugg augcuguuaaaguuaauugcaaugagaccaaauuuuacuuguuaagcaguuugaguauguuaagaggugccuuuauauaua gaauuauaaaagggauuuguaaauaauuacaacagauggccuacuuuaagaaaugcuauuguuuuacccuuaagauggauuaac uuacuauaaacuaaacacuuauccuucuuuguuggaacuuacagaaagagauuugauugguguuaucaggacuacguuucuau cgugaguuucguugccuaaaaaaagguggaucuugaaaugauuauaaaugauaaagcuauaucacccccuaaaaauuugauau ggacuaguuucccuagaaauuauaugccgucacacauacaaaacuauauagaacaugaaaaauuaaaauuuuccgagagugau aaaucaagaagaguauuagaguauuauuuaagagauaacaaauucaaugaaugugauuuauacaacugcguaguuaaucaaa guuaucucaacaacccuaaucaugugguaucauugacaggcaaagaaagagaacucaguguagguagaauguuugcaaugca accgggaauguucagacagguucaaauauuggcagagaaaaugauagcugaaaacauuuuacaauucuuuccugaaagucuu acaagauauggugaucuagaacuacaaaaaauauuagaauugaaagcaggaauaaguaacaaaucaaaucgcuacaaugauaa uuacaacaauuacauuaguaagugcucuaucaucacagaucucagcaaauucaaucaagcauuucgauaugaaacgucaugua uuuguagugaugugcuggaugaacugcauggguacaaucucuauuuuccugguuacauuuaacuauuccucaugucacaa -continued uaauaugcacauauaggcaugcacccccuauauaagagaucauauuguagaucuuaacaauguagaugaacaaaguggauua uauagauaucacaugguggauuugaagggguggugucaaaaacuaggaccauagaagcuauaucacuauuggaucuaauau cucucaaagggaaauucucaauuacugcuuuaauuaauggugacaaucaauaaugauauaagcaaaccagucagacucaug gaaggucaaacucaugcucaagcagauuauuugcuagcauuaaauagccuuaaauuacuguauaaagaguaugcaggcauag gucacaaauuaaaaggaacugagacuuauauaucacgagauaugcaauuuaugaguaaaacaauucaacauaacggguguauau uacccugcuaguauaaagaaaguccuaagaguggaccguggauaaacacuauacuugaugauuucaagugagucuagaau cuauaaaguaguuugacacaagaauuagaauauagaggugaaagucuauuaugcaguuuaauauuuagaaauguauggeuuaua uaaucaaauugcucuacaauuaaaaaaucaugcguuaugaacaauaaauuauauuuggacauauuaaagguucugaaacacu uaaaaaccuuuuuaaucuugauaauauugauacagcauuaacauuguauaugaauuuacccauguuauuuggugguggug aucccaacuuguuauaucgaaguuucauagaagaacuccugauuuccucacagaggcuauaguucacucuguguucauacu uaguuauuauacaaaccaugacuuaaaagauaaacuucaagauuugucagaugauagauugaauaaguucuuaacaugcauaa ucacguuugacaaaaacccuaaugcugaauucguaacauugaugagagauccucaagcuuuagggucugagagacaagcuaaa auuacuagugaaaucaauagacuggcaguacagagguuugaguacagcuccaaacaaaauauuccaaaagugcacaaca uuauaccacuacagagauagaucaaaugauauuaugcaaaauauagaaccuacauauccucacgggcuaagaguuguuaug aaaguuuacccuuuuauaaagcagagaaaauaguaaaucuuauaucagguacaaaaucuauaacuaacauacuggaaaagacu ucugccauagacuuaacagauauugauagagccacugagaugaugaggaaaaacauaacuuugcuuauaaggauacuuccau uggauuguaacagagauaaaagagaaauauugaguauggaaaaccuaaguauuacugaauuaagcaaauaugauuagggaaag aucuuggucuuuauccaauauaguuguguuacaucacccaguaucauguauacaauggacaucaaauauacaacaagcacua uagcuaguggcauaauuauagagaaauauaauguaacaguuuaacacgguggugagagaggaccaacuaaaccaugggguugg uucaucuacacaagagaaaaaaacaaugccaguuuauaauagacaaguuuuaaccaaaaaacaaagagaucaaauagaucuauu agcaaaauuggauuggguguaugcaucauauagauaacaaggaugaauucauggaagaacucagcauaggaacccuuggguua acauaugaaaaggccaaaaaauuauuuccacaauauuuaagugucaacuauuugcaucgccuuacagucaguaguagaccaug ugaauucccugcaucaauaccagcuuuauagaacaacaaauuaucacuuugacacuagcccuauuaaucgcauauuaacagaaa aguauggugaugaagauauugacauaguauuccaaaacuguauaagcuuuggccuuagcuuaaugucaguaguagaacaauu uacuaaugauguccuaacagaauuauucucauaccuaagcuuaaugagauacauuugaugaaaccuccccauauucacaggug auguugauauucacaaguuaaaacaagugauacaaaaacagcauauguuuuuaccagacaaaauaaguuugacucaauaugug gaauuauucuuaaguaacaaaacacucaaaucuggaucucauguuaauucaauuuaauauuggcacauaaaauaucugacua uuuucauaauacuuacauuuuaaguacuaauuuagcuggacauuggauucuaauuauacaacuuaugaaagauucuaaaggu auuuugaaaagauugggagagggauauauaacugaucauauguuuauuaauuugaaaguuuucuucaaugcuuauaag accuaucucuuguguuucauaaagguuauggcaaagcaaaacuggagugugauaugaacacuucagaucuucuaugugauau uggaauuaauagacaguaguuauuggaagucuaugucuaagguauuuuagaacaaaaaguuaucaaauacauucuuagcca agaugcaaguuuacauagaguaaaaggaugucauagcuucaaauuaugguuucuuaaacgucuuaaugagcagaauuuaca guuugcccuugggeuguuaacauagauuaucauccaacacauaugaaagcaauauuaacuuauauagaucuuguuagaaugg gauugauaaauauagauagaauacacauuaaaaaaaacacaaauucaaugaugaauuuuauacuucuaaucucuuuuacauu aauuauaacuucucagauauaucaucuauuaacuaaacauauaaggauugcuaauucagaauuagaaaaaauucaacaa auuauaucauccuacaccagaaacccuagagaauauacuagccaaucgauuaaaaguaaugacaaaaagacacugaacgacua uuguauaagguaaaaauguugacucaauaauguuaccauuguuaucuaauaagaagcuuguuaaaucgucugcaaugauuaga accaauuacagcaaacaagaccuguacaaucuauucccuacgguuugaucgauagaauuauagaucauucagguaauacagc caaauccaaccaacuuuacacuacuacuucccaucaaauaucuuuagugcacaauagcacaucacuuuauugcaugcuuccuu ggcaucauauuaauagauucaauuuuguauuuaguucuacagguuguaaaauuaguauagaguauauuuuaaaagaccuaa aauuaaagauccuaauuguauagcauucauaggugaaggagcagggaauuuauuauugcguacaguggguggaacuucauccu gacauaagauauauuuacagaagucugaaagauugcaaugaucauaguuuaccuauugaguuuuuaaggcuauacaauggac auaucaacauugauuauggugaaaauuugaccauuccugcuacagaugcaaccaacaacauucauuggucuuauuuacauaua aaguuugcugaaccuaucagucuuuuuguaugugaugccgaauugccuguaacagucaacggaguaaaauuauaauagaau ggagcaagcauguaagaaaaugcaaguacuguuccucaguuaauaaaugu acguuaauaguaaaauaucaugcucaagauga uauugauuucaaauuagacaauauaacuauauuaaaaacuuauguaugcuuaggcaguaaguuaaagggaucggagguuuac uuaguccuuacaauagguccugcaaauauauuccaguauuuaaugu aguacaaaaugcuaaauugaucuaucaagaaccaa aaauuucaucaugccuaagaaagcugauaaagagucuauugaugcaaauauuaaaaguuugauacccuuuuuguuaccu auaacaaaaaaggaauuaauacugcauugucaaaacuaaagagguguugu uaguggagauauacuaucauauucuauagcug gacggaaugaaguuuucagcaauaaacuuauaaaucauaagcauaugaacaucuuaaagugguucaaucauguuuuaaauuu cagaucaacagaacuaaacuauaaccauuuauauauggu agaaucuacauauccuuaccuaagugaauuguuaaacagcuuga caacuaaugaacuuaaaaaacugauuaaaaucacagguagucuguuauacaacuuucauaaugaauaa mRNA coding for the protein M2-1 of the RSV strain ATCC VR-26 long:
mRNA sequence according to SEQ ID No. 18:
Augucacgaaggaauccuugcaaauuugaaauucgaggucauugcuugaauggu aagagaugucauuuagucauaauuau uuugaauggccaccccaugcacugcucguaagacaaaacuuuauguuaaacagaauacuuaagucuauggauaaaaguauaga uaccuuaucagaaauaagu ggagcugcagaguuggacagaacagaagaguaugcucuuggu guaguuggagugcuagagag uuauauaggaucaauaauaauauaacuaaacaaucagcauguguugccaugagcaaacuccucacugaacucaauagugaug auaucaaaaacugagagacaaugaagagcuaaauucacccaagauaagagu guacaauacugucauaucauauauugaaagc aacaggaaaaacaauaaacaaacuauccaucuguuaaaaagauugccagcagacguauugaagaaaaccaucaaaaacacauug gauauccacaagagcauaaccaucaacaacccaaaagaauuaacuguuagugauacaaaugaccaugccaaaaauaaugauacu accuga mRNA coding for the protein M2-2 of the RSV strain ATCC VR-26 long:
mRNA sequence according to SEQ ID No. 19:
augaccaugccaaaaauaaugauacuaccugacaaauauccuuguaguauaauccauacuaauaacaaguagauguagagu cacuauguauaaucgaaagaacacacuauauuucaaucaaaacaacccaaauaaccauauguacucaccgaaucaaacauucaa ugaaauccauuggaccucacaagacuugauugacacaauucaaaauuuucuacagcaucuaggu guuauugaggauauauau acaauauauauauuagugucauaa mRNA coding for the phosphoprotein P of the RSV strain ATCC VR-26 long:
mRNA sequence according to SEQ ID No. 20:
auggaaaaguuugcuccugaauuccauggagaagaugcaaacaacagggcuacuaaauuccuagaaucaauaaagggcaaauu cacaucaccuaaagaucccaagaaaaaagauaguaucauaucugucaacucaauagauauagaaguaaccaaagaaagcccuau aacaucaaauucaaccauuauuaacccaacaaaugagacagaugauaaugcagggaacaagcccaauuaucaaagaaaaccucu aguaaguuucaaagaagacccuauaccaagugauaaucccuuuucaaaacuauacaaagaaaccauagagacauuugauaacaa ugaagaagaaucuagcuauucauaugaagaaauaaaugaucagacgaacgauaauauaacugcaagauuagauaggauugaug aaaaauuaagugaaauacuaggaaugcuucacacauuaguaguagcaagugcaggaccuacaucugcuagggaugguauaag agaugccaugguugguuuaagagaagaaaaugauagaaaaaaucagaacugaagcauuaaugaccaaugacagauuagaagcua uggcaagacucaggaaugaggaaaguga aaagauggcaaaagacacaucagaugaaguguc ucu caauccaacaucagagaaa uugaacaaccguuggaagggaaugauagugacaaugaucuaucacuugaagauuucuga mRNA coding for the non-structural protein NS1 of the RSV strain ATCC VR-26 long:
mRNA sequence according to SEQ ID No. 21:
augggcagcaauucguugaguaugauaaaaguuagauuacaaaauuuguuugacaaugaugaaguagcauuguuaaaaauaa caugcuauacugacaaauuaauacauuuaacuaaugcuuuggcuaaggcagugauacauacaaucaaauugaauggcauugu guuugugcauguuauuacaagu agu gau auuugcccuaauaauaauauuguaguaaaauccaauuucacaacaaugccagug cuacaaaauggagguuauauauggg aaaugaugg aauuaacacauugcucucaaccuaauggucuaau agaugacaauugug -continued
```
aaauuaaauucuccaaaaaacuaagugauucaacaaugaccaauuauaugaaucaauuaucugaauuacuuggauuugaucuu aauccauaa
``` mRNA coding for the non-structural protein NS2 of the RSV strain ATCC VR-26 long:
mRNA sequence according to SEQ ID No. 22:
```
auggacacaacccacaaugauaccacaccacaaagacugaugaucagacaugagaccguugucacuugagacuacaauaaca ucacuaaccagagacaucauaacacacagauuuauauacuuaauaaaucaugaaugcauagugagaaaacuugaugaaagaca ggccacauuuacauuccuggucaacuaugaaaugaaacuauugcacaaaguaggaagcacuaaauauaaaaaauauacugaau acaacacaaaauauggcacuuucccuaugccgauauucaucaaucaugaugggucuagaaugcauuggcauuaagccuaca aagcauacucccauaauauacaaguaugaucucaauccauag
```

In the context of the invention, additionally to the here disclosed nucleic acid sequences, also nucleic acid sequences of different Respiratory syncytial virus (RSV) isolates are incorporated herewith. These different Respiratory syncytial virus (RSV) isolates show preferably an identity of at least 50%, 60%, 70%, more preferably of at least 80% and most preferably of at least 90% with the nucleic acid sequences according to SEQ ID Nos. 12-22 or of fragments thereof.

In a preferred embodiment, the mRNA sequence according to the invention does not comprise a reporter gene or a marker gene. Preferably, the mRNA sequence according to the invention does not encode, for instance, luciferase; green fluorescent protein (GFP) and its variants (such as eGFP, RFP or BFP); α-globin; hypoxanthine-guanine phosphoribosyltransferase (HGPRT); β-galactosidase; galactokinase; alkaline phosphatase; secreted embryonic alkaline phosphatase (SEAP)) or a resistance gene (such as a resistance gene against neomycin, puromycin, hygromycin and zeocin). In a preferred embodiment, the mRNA sequence according to the invention does not encode luciferase. In another embodiment, the mRNA sequence according to the invention does not encode GFP or a variant thereof.

In a further preferred embodiment, the mRNA sequence according to the invention does not encode a protein (or a fragment of a protein) derived from a virus belonging to the family of Orthomyxoviridae. Preferably the mRNA sequence does not encode a protein that is derived from an influenza virus, more preferably an influenza A virus. Preferably, the mRNA sequence according to the invention does not encode an influenza A protein selected from the group consisting of hemagglutinin (HA), neuraminidase (NA), nucleoprotein (NP), M1, M2, NS1, NS2 (NEP: nuclear export protein), PA, PB1 (polymerase basic 1), PB1-F2 and PB2. In another preferred embodiment, the mRNA according to the invention does not encode ovalbumin (OVA) or a fragment thereof. Preferably, the mRNA sequence according to the invention does not encode an influenza A protein or ovalbumin.

By a further embodiment, the inventive mRNA preferably comprises at least one of the following structural elements: a 5'- and/or 3'-untranslated region element (UTR element), particularly a 5'-UTR element which comprises or consists of a nucleic acid sequence which is derived from the 5'-UTR of a TOP gene or from a fragment, homolog or a variant thereof, or a 5'- and/or 3'-UTR element which may be derivable from a gene that provides a stable mRNA or from a homolog, fragment or variant thereof; a histone-stem-loop structure, preferably a histone-stem-loop in its 3' untranslated region; a 5'-CAP structure; a poly-A tail; or a poly(C) sequence.

In a preferred embodiment of the first aspect of the present invention, the inventive mRNA comprises at least one 5'- or 3'-UTR element. In this context, an UTR element comprises or consists of a nucleic acid sequence which is derived from the 5'- or 3'-UTR of any naturally occurring gene or which is derived from a fragment, a homolog or a variant of the 5'- or 3'-UTR of a gene. Preferably, the 5'- or 3'-UTR element used according to the present invention is heterologous to the coding region of the inventive mRNA sequence. Even if 5'- or 3'-UTR elements derived from naturally occurring genes are preferred, also synthetically engineered UTR elements may be used in the context of the present invention.

In a particularly preferred embodiment of the first aspect of the present invention, the inventive mRNA sequence comprises at least one 5'-untranslated region element (5'UTR element) which comprises or consists of a nucleic acid sequence which is derived from the 5'UTR of a TOP gene or which is derived from a fragment, homolog or variant of the 5'UTR of a TOP gene.

It is particularly preferred that the 5'UTR element does not comprise a TOP-motif or a 5'TOP, as defined above.

In some embodiments, the nucleic acid sequence of the 5'UTR element which is derived from a 5'UTR of a TOP gene terminates at its 3'-end with a nucleotide located at position 1, 2, 3, 4, 5, 6, 7, 8, 9 or 10 upstream of the start codon (e.g. A(U/T)G) of the gene or mRNA it is derived from. Thus, the 5'UTR element does not comprise any part of the protein coding region. Thus, preferably, the only protein coding part of the inventive mRNA is provided by the coding region.

The nucleic acid sequence, which is derived from the 5'UTR of a TOP gene, is derived from a eukaryotic TOP gene, preferably a plant or animal TOP gene, more preferably a chordate TOP gene, even more preferably a vertebrate TOP gene, most preferably a mammalian TOP gene, such as a human TOP gene.

For example, the 5'UTR element is prefereably selected from 5'-UTR elements comprising or consisting of a nucleic acid sequence, which is derived from a nucleic acid sequence selected from the group consisting of SEQ ID Nos. 1-1363, SEQ ID NO. 1395, SEQ ID NO. 1421 and SEQ ID NO. 1422 of the patent application WO2013/143700, whose disclosure is incorporated herein by reference, from the homologs of SEQ ID Nos. 1-1363, SEQ ID NO. 1395, SEQ ID NO. 1421 and SEQ ID NO. 1422 of the patent application WO2013/143700, from a variant thereof, or preferably from a corresponding RNA sequence. The term "homologs of SEQ ID Nos. 1-1363, SEQ ID NO. 1395, SEQ ID NO. 1421 and SEQ ID NO. 1422 of the patent application WO2013/143700" refers to sequences of other species than *Homo sapiens*, which are homologous to the sequences according to SEQ ID Nos. 1-1363, SEQ ID NO. 1395, SEQ ID NO. 1421 and SEQ ID NO. 1422 of the patent application WO2013/143700.

In a preferred embodiment, the 5'UTR element comprises or consists of a nucleic acid sequence which is derived from a nucleic acid sequence extending from nucleotide position 5 (i.e. the nucleotide that is located at position 5 in the sequence) to the nucleotide position immediately 5' to the start codon (located at the 3' end of the sequences), e.g. the nucleotide position immediately 5' to the ATG sequence, of a nucleic acid sequence selected from SEQ ID Nos. 1-1363, SEQ ID NO. 1395, SEQ ID NO. 1421 and SEQ ID NO. 1422 of the patent application WO2013/143700, from the homologs of SEQ ID Nos. 1-1363, SEQ ID NO. 1395, SEQ ID NO. 1421 and SEQ ID NO. 1422 of the patent application WO2013/143700, from a variant thereof, or a corresponding RNA sequence. It is particularly preferred that the 5' UTR element is derived from a nucleic acid sequence extending from the nucleotide position immediately 3' to the 5'TOP to the nucleotide position immediately 5' to the start codon (located at the 3' end of the sequences), e.g. the nucleotide position immediately 5' to the ATG sequence, of a nucleic acid sequence selected from SEQ ID Nos. 1-1363, SEQ ID NO. 1395, SEQ ID NO. 1421 and SEQ ID NO. 1422 of the patent application WO2013/143700, from the homologs of SEQ ID Nos. 1-1363, SEQ ID NO. 1395, SEQ ID NO. 1421 and SEQ ID NO. 1422 of the patent application WO2013/143700, from a variant thereof, or a corresponding RNA sequence.

In a particularly preferred embodiment, the 5'UTR element comprises or consists of a nucleic acid sequence, which is derived from a 5'UTR of a TOP gene encoding a ribosomal protein or from a variant of a 5'UTR of a TOP gene encoding a ribosomal protein. For example, the 5'UTR element comprises or consists of a nucleic acid sequence which is derived from a 5'UTR of a nucleic acid sequence according to any of SEQ ID NOs: 67, 170, 193, 244, 259, 554, 650, 675, 700, 721, 913, 1016, 1063, 1120, 1138, and 1284-1360 of the patent application WO2013/143700, a corresponding RNA sequence, a homolog thereof, or a variant thereof as described herein, preferably lacking the 5'TOP motif. As described above, the sequence extending from position 5 to the nucleotide immediately 5' to the ATG (which is located at the 3' end of the sequences) corresponds to the 5'UTR of said sequences.

Preferably, the 5'UTR element comprises or consists of a nucleic acid sequence which is derived from a 5'UTR of a TOP gene encoding a ribosomal Large protein (RPL) or from a homolog or variant of a 5'UTR of a TOP gene encoding a ribosomal Large protein (RPL). For example, the 5'UTR element comprises or consists of a nucleic acid sequence which is derived from a 5'UTR of a nucleic acid sequence according to any of SEQ ID NOs: 67, 259, 1284-1318, 1344, 1346, 1348-1354, 1357, 1358, 1421 and 1422 of the patent application WO2013/143700, a corresponding RNA sequence, a homolog thereof, or a variant thereof as described herein, preferably lacking the 5'TOP motif.

In a particularly preferred embodiment, the 5'UTR element comprises or consists of a nucleic acid sequence which is derived from the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, or from a variant of the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, wherein preferably the 5'UTR element does not comprise the 5'TOP of said gene.

Accordingly, in a particularly preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 23 (5'-UTR of human ribosomal protein Large 32 lacking the 5' terminal oligopyrimidine tract: GGCGCTGCCTACGGAGGTGGCAGC-CATCTCCTTCTCGGCATC; corresponding to SEQ ID No. 1368 of the patent application WO2013/143700) or preferably to a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 23 or more preferably to a corresponding RNA sequence, wherein, preferably, the fragment is as described above, i.e. being a continuous stretch of nucleotides representing at least 20%, preferably at least 30%, more preferably at least 40%, more preferably at least 50%, even more preferably at least 60%, even more preferably at least 70%, even more preferably at least 80%, and most preferably at least 90%. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In some embodiments, the inventive mRNA comprises a 5'UTR element which comprises or consists of a nucleic acid sequence which is derived from the 5'UTR of a vertebrate TOP gene, such as a mammalian, e.g. a human TOP gene, selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB, or from a homolog or variant thereof, wherein preferably the 5'UTR element does not comprise a TOP-motif or the 5'TOP of said genes, and wherein optionally the 5'UTR element starts at its 5'-end with a nucleotide located at position 1, 2, 3, 4, 5, 6, 7, 8, 9 or 10 downstream of the 5' terminal oligopyrimidine tract (TOP) and wherein further optionally the 5'UTR element which is derived from a 5'UTR of a TOP gene terminates at its 3'-end with a nucleotide located at position 1, 2, 3, 4, 5, 6, 7, 8, 9 or 10 upstream of the start codon (A(U/T)G) of the gene it is derived from.

In further particularly preferred embodiments, the 5'UTR element comprises or consists of a nucleic acid sequence which is derived from the 5'UTR of a ribosomal protein Large 32 gene (RPL32), a ribosomal protein Large 35 gene (RPL35), a ribosomal protein Large 21 gene (RPL21), an ATP synthase, H+ transporting, mitochondrial F1 complex, alpha subunit 1, cardiac muscle (ATP5A1) gene, an hydroxysteroid (17-beta) dehydrogenase 4 gene (HSD17B4), an androgen-induced 1 gene (AIG1), cytochrome c oxidase subunit VIc gene (COX6C), or a N-acylsphingosine amidohydrolase (acid ceramidase) 1 gene (ASAH1) or from a variant thereof, preferably from a vertebrate ribosomal protein Large 32 gene (RPL32), a vertebrate ribosomal protein Large 35 gene (RPL35), a vertebrate ribosomal protein Large 21 gene (RPL21), a vertebrate ATP synthase, H+ transporting, mitochondrial F1 complex, alpha subunit 1, cardiac muscle (ATP5A1) gene, a vertebrate hydroxysteroid (17-beta) dehydrogenase 4 gene (HSD17B4), a vertebrate androgen-induced 1 gene (AIG1), a vertebrate cytochrome c oxidase subunit VIc gene (COX6C), or a vertebrate N-acylsphingosine amidohydrolase (acid ceramidase) 1 gene (ASAH1) or from a variant thereof, more preferably from a mammalian ribosomal protein Large 32 gene (RPL32), a ribosomal protein Large 35 gene (RPL35), a ribosomal protein Large 21 gene (RPL21), a mammalian ATP synthase, H+ transporting, mitochondrial F1 complex, alpha subunit 1, cardiac muscle (ATP5A1) gene, a mammalian hydroxysteroid (17-beta) dehydrogenase 4 gene (HSD17B4), a mammalian androgen-induced 1 gene (AIG1), a mammalian cyto-chrome c oxidase subunit VIc gene (COX6C), or a mammalian N-acylsphingosine ami-dohydrolase (acid ceramidase) 1 gene (ASAH1) or from a variant thereof, most preferably from a human ribosomal protein Large 32 gene (RPL32), a human ribosomal protein Large 35 gene (RPL35), a human ribosomal protein Large 21 gene (RPL21), a human ATP syn-thase, H+ transporting, mitochondrial F1 complex, alpha subunit 1, cardiac muscle (ATP5A1) gene, a human hydroxysteroid (17-beta) dehydrogenase 4 gene (HSD17B4), a human androgen-induced 1 gene (AIG1), a human cytochrome c oxidase subunit VIc gene (COX6C), or a human N-acylsphingosine amidohydrolase (acid ceramidase) 1 gene (ASAH1) or from a variant thereof, wherein preferably the 5'UTR element does not comprise the 5'TOP of said gene.

Accordingly, in a particularly preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 1368, or SEQ ID NOs 1412-1420 of the patent application WO2013/143700, or a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 1368, or SEQ ID NOs 1412-1420 of the patent application WO2013/143700, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Accordingly, in a particularly preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 36 (5'-UTR of ATP5A1 lacking the 5' terminal oligopyrimidine tract: GCGGCTCGGCCAT-TTTGTCCCAGTCAGTCCG-GAGGCTGCGGCTGCAGAAGTACCGCC TGCG-GAGTAACTGCAAAG; corresponding to SEQ ID No. 1414 of the patent application WO2013/143700) or preferably to a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 26 or more preferably to a corresponding RNA sequence, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In a further preferred embodiment, the inventive mRNA further comprises at least one 3'UTR element, which comprises or consists of a nucleic acid sequence derived from the 3'UTR of a chordate gene, preferably a vertebrate gene, more preferably a mammalian gene, most preferably a human gene, or from a variant of the 3'UTR of a chordate gene, preferably a vertebrate gene, more preferably a mammalian gene, most preferably a human gene.

The term '3'UTR element' refers to a nucleic acid sequence which comprises or consists of a nucleic acid sequence that is derived from a 3'UTR or from a variant of a 3'UTR. A 3'UTR element in the sense of the present invention may represent the 3'UTR of an mRNA. Thus, in the sense of the present invention, preferably, a 3'UTR element may be the 3'UTR of an mRNA, preferably of an artificial mRNA, or it may be the transcription template for a 3'UTR of an mRNA. Thus, a 3'UTR element preferably is a nucleic acid sequence which corresponds to the 3'UTR of an mRNA, preferably to the 3'UTR of an artificial mRNA, such as an mRNA obtained by transcription of a genetically engineered vector construct. Preferably, the 3'UTR element fulfils the function of a 3'UTR or encodes a sequence which fulfils the function of a 3'UTR.

Preferably, the inventive mRNA comprises a 3'UTR element which may be derivable from a gene that relates to an mRNA with an enhanced half-life (that provides a stable mRNA), for example a 3'UTR element as defined and described below.

In a particularly preferred embodiment, the 3'UTR element comprises or consists of a nucleic acid sequence which is derived from a 3'UTR of a gene selected from the group consisting of an albumin gene, an ca-globin gene, a β-globin gene, a tyrosine hydroxylase gene, a lipoxygenase gene, and a collagen alpha gene, such as a collagen alpha 1(I) gene, or from a variant of a 3'UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene according to SEQ ID No. 1369-1390 of the patent application WO2013/143700 whose disclosure is incorporated herein by reference. In a particularly preferred embodiment, the 3'UTR element comprises or consists of a nucleic acid sequence which is derived from a 3'UTR of an albumin gene, preferably a vertebrate albumin gene, more preferably a mammalian albumin gene, most preferably a human albumin gene according to SEQ ID No. 24.

```
Human albumin 3'UTR SEQ ID No. 24:
CATCACATTT AAAAGCATCT CAGCCTACCA TGAGAATAAG

AGAAAGAAAA TGAAGATCAA AAGCTTATTC ATCTGTTTTT

CTTTTTCGTT GGTGTAAAGC CAACACCCTG TCTAAAAAAC

ATAAATTTCT TTAATCATTT TGCCTCTTTT CTCTGTGCTT

CAATTAATAA AAAATGGAAA GAATCT
(corresponding to SEQ ID No: 1369 of the patent
application WO2013/143700).
```

In this context, it is particularly preferred that the inventive mRNA comprises a 3'-UTR element comprising a corresponding RNA sequence derived from the nucleic acids according to SEQ ID No. 1369-1390 of the patent application WO2013/143700 or a fragment, homolog or variant thereof.

Most preferably the 3'-UTR element comprises the nucleic acid sequence derived from a fragment of the human albumin gene according to SEQ ID No. 25:
albumin7 3'UTR
CATCACATTTAAAAGCATCTCAGCCTACCAT-
GAGAATAAGAGAAAGAAAATGAAGA TCAATAGCT-
TATTCATCTCTTTTTCTTTTTCGTTGGTGTAAAGC-
CAACACCCTGTCTA
AAAAACATAAATTTCTTTAATCAT-
TTTGCCTCTTTTCTCTGTGCTTCAATTAATAAAA
AATGGAAAGAACCT (SEQ ID No. 25 corresponding to SEQ ID No: 1376 of the patent application WO2013/143700)

In this context, it is particularly preferred that the 3'-UTR element of the inventive mRNA comprises or consists of a corresponding RNA sequence of the nucleic acid sequence according to SEQ ID No. 25.

In another particularly preferred embodiment, the 3'UTR element comprises or consists of a nucleic acid sequence which is derived from a 3'UTR of an α-globin gene, preferably a vertebrate α- or β-globin gene, more preferably a mammalian α- or β-globin gene, most preferably a human α- or β-globin gene according to SEQ ID No. 26-28:

```
3'-UTR of Homo sapiens hemoglobin, alpha 1 (HBA1)
GCTGGAGCCTCGGTGGCCATGCTTCTTGCCCCTTGGGCCTCCCCCCAGCC

CCTCCTCCCCTTCCTGCACCCGTACCCCCGTGGTCTTTGAATAAAGTCTG

AGTGGGCGGC
(SEQ ID No: 26 corresponding to SEQ ID No. 1370 of
the patent application WO2013/143700)

3'-UTR of Homo sapiens hemoglobin, alpha 2 (HBA2)
GCTGGAGCCTCGGTAGCCGTTCCTCCTGCCCGCTGGGCCTCCCAACGGGC

CCTCCTCCCCTCCTTGCACCGGCCCTTCCTGGTCTTTGAATAAAGTCTGA

GTGGGCAG
(SEQ ID No: 27 corresponding to SEQ ID No. 1371 of
the patent application WO2013/143700)

3'-UTR of Homo sapiens hemoglobin, beta (HBB)
GCTCGCTTTCTTGCTGTCCAATTTCTATTAAAGGTTCCTTTGTTCCCTAA

GTCCAACTACTAAACTGGGGGATATTATGAAGGGCCTTGAGCATCTGGAT

TCTGCCTAATAAAAAACATTTATTTTCATTGC
(SEQ ID No: 28 corresponding to SEQ ID No. 1372 of
the patent application WO2013/143700)
```

For example, the 3'UTR element may comprise or consist of the center, α-complex-binding portion of the 3'UTR of an α-globin gene, such as of a human α-globin gene, preferably according to SEQ ID No. 29:

Center, α-complex-binding portion of the 3'UTR of an α-globin gene (also named herein as "muag")
GCCCGATGGGCCTCC-
CAACGGGCCCTCCTCCCCTCCTTGCACCG (SEQ ID NO. 29 corresponding to SEQ ID No. 1393 of the patent application WO2013/143700).

In this context, it is particularly preferred that the 3'-UTR element of the inventive mRNA comprises or consists of a corresponding RNA sequence of the nucleic acid sequence according to SEQ ID No. 29 or a homolog, a fragment or variant thereof.

The term 'a nucleic acid sequence which is derived from the 3'UTR of a [ . . . ] gene' preferably refers to a nucleic acid sequence which is based on the 3'UTR sequence of a [ . . . ] gene or on a part thereof, such as on the 3'UTR of an albumin gene, an α-globin gene, a β-globin gene, a tyrosine hydroxylase gene, a lipoxygenase gene, or a collagen alpha gene, such as a collagen alpha 1(I) gene, preferably of an albumin gene or on a part thereof. This term includes sequences corresponding to the entire 3'UTR sequence, i.e. the full length 3'UTR sequence of a gene, and sequences corresponding to a fragment of the 3'UTR sequence of a gene, such as an albumin gene, α-globin gene, β-globin gene, tyrosine hydroxylase gene, lipoxygenase gene, or collagen alpha gene, such as a collagen alpha 1(I) gene, preferably of an albumin gene.

The term 'a nucleic acid sequence which is derived from a variant of the 3'UTR of a [ . . . ] gene' preferably refers to a nucleic acid sequence which is based on a variant of the 3'UTR sequence of a gene, such as on a variant of the 3'UTR of an albumin gene, an α-globin gene, a β-globin gene, a tyrosine hydroxylase gene, a lipoxygenase gene, or a collagen alpha gene, such as a collagen alpha 1(I) gene, or on a part thereof as described above. This term includes sequences corresponding to the entire sequence of the variant of the 3'UTR of a gene, i.e. the full length variant 3'UTR sequence of a gene, and sequences corresponding to a fragment of the variant 3'UTR sequence of a gene. A fragment in this context preferably consists of a continuous stretch of nucleotides corresponding to a continuous stretch of nucleotides in the full-length variant 3'UTR, which represents at least 20%, preferably at least 30%, more preferably at least 40%, more preferably at least 50%, even more preferably at least 60%, even more preferably at least 70%, even more preferably at least 80%, and most preferably at least 90% of the full-length variant 3'UTR. Such a fragment of a variant, in the sense of the present invention, is preferably a functional fragment of a variant as described herein.

Preferably, the at least one 5'UTR element and the at least one 3'UTR element act synergistically to increase protein production from the inventive mRNA as described above.

In a particularly preferred embodiment, the inventive mRNA comprising a coding region, encoding at least one antigenic peptide or protein of Respiratory syncytial virus (RSV) or a fragment, variant or derivative thereof, comprises a histone stem-loop sequence/structure. Such histone stem-loop sequences are preferably selected from histone stem-loop sequences as disclosed in WO 2012/019780, whose disclosure is incorporated herewith by reference.

A histone stem-loop sequence, suitable to be used within the present invention, is preferably selected from at least one of the following formulae (I) or (II):

Formula (I) (Stem-Loop Sequence without Stem Bordering Elements):

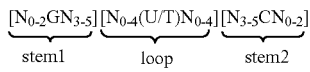

Formula (II) (Stem-Loop Sequence with Stem Bordering Elements):

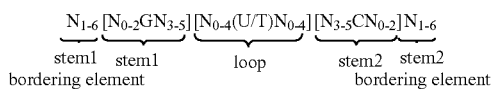

wherein:

stem1 or stem2 bordering elements $N_1$-6 is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof;

stem1 $[N_{0-2}GN_{3-5}]$ is reverse complementary or partially reverse complementary with element stem2, and is a consecutive sequence between of 5 to 7 nucleotides;
  wherein $N_{0-2}$ is a consecutive sequence of 0 to 2, preferably of 0 to 1, more preferably of 1 N, wherein each N is independently from another selected from a nucleotide selected from A, U, T, G and C or a nucleotide analogue thereof;
  wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof, and
  wherein G is guanosine or an analogue thereof, and may be optionally replaced by a cytidine or an analogue thereof, provided that its complementary nucleotide cytidine in stem2 is replaced by guanosine;

loop sequence $[N_{0-4}(U/T)N_{0-4}]$ is located between elements stem1 and stem2, and is a consecutive sequence of 3 to 5 nucleotides, more preferably of 4 nucleotides;
  wherein each $N_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and
  wherein U/T represents uridine, or optionally thymidine;

stem2 $[N_{3-5}CN_{0-2}]$ is reverse complementary or partially reverse complementary with element stem1, and is a consecutive sequence between of 5 to 7 nucleotides;
  wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof;
  wherein $N_{0-2}$ is a consecutive sequence of 0 to 2, preferably of 0 to 1, more preferably of 1 N, wherein each N is independently from another selected from a nucleotide selected from A, U, T, G or C or a nucleotide analogue thereof; and
  wherein C is cytidine or an analogue thereof, and may be optionally replaced by a guanosine or an analogue thereof provided that its complementary nucleoside guanosine in stem1 is replaced by cytidine;

wherein stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one ore more bases in one stem do not have a complementary base in the reverse complementary sequence of the other stem.

According to a further preferred embodiment of the first inventive aspect, the inventive mRNA sequence may comprise at least one histone stem-loop sequence according to at least one of the following specific formulae (Ia) or (IIa):

Formula (Ia) (Stem-Loop Sequence without Stem Bordering Elements):

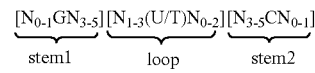

Formula (IIa) (Stem-Loop Sequence with Stem Bordering Elements):

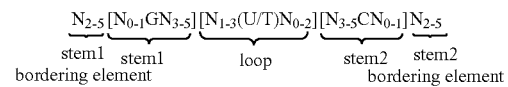

wherein:
N, C, G, T and U are as defined above.

According to a further more particularly preferred embodiment of the first aspect, the inventive mRNA sequence may comprise at least one histone stem-loop sequence according to at least one of the following specific formulae (Ib) or (IIb):

Formula (Ib) (Stem-Loop Sequence without Stem Bordering Elements):

$$\underbrace{[N_1GN_4]}_{stem1}\underbrace{[N_2(U/T)N_1]}_{loop}\underbrace{[N_4CN_1]}_{stem2}$$

Formula (IIb) (Stem-Loop Sequence with Stem Bordering Elements):

$$\underbrace{N_{4-5}}_{\substack{stem1\\bordering\ element}}\underbrace{[N_1GN_4]}_{stem1}\underbrace{[N_2(U/T)N_1]}_{loop}\underbrace{[N_4CN_1]}_{stem2}\underbrace{N_{4-5}}_{\substack{stem2\\bordering\ element}}$$

wherein:

N, C, G, T and U are as defined above.

A particular preferred histone stem-loop sequence is the sequence according to SEQ ID NO: 30 CAAAGGCTCTTTTCAGAGCCACCA or more preferably the corresponding RNA sequence of the nucleic acid sequence according to SEQ ID NO: 30 (CAAAGGCUCUUUUCAGAGCCACCA SEQ ID NO: 37).

In a particular preferred embodiment of the first aspect of the present invention the inventive mRNA comprises additionally to the coding region encoding at least one antigenic peptide or protein of Respiratory syncytial virus (RSV) or a fragment, variant or derivative thereof, a poly(A) sequence, also called poly-A-tail, preferably at the 3'-terminus of the inventive mRNA. When present, such a poly(A) sequence comprises a sequence of about 25 to about 400 adenosine nucleotides, preferably a sequence of about 50 to about 400 adenosine nucleotides, more preferably a sequence of about 50 to about 300 adenosine nucleotides, even more preferably a sequence of about 50 to about 250 adenosine nucleotides, most preferably a sequence of about 60 to about 250 adenosine nucleotides. In this context, the term "about" refers to a deviation of ±10% of the value(s) it is attached to. This poly(A) sequence is preferably located 3' of the coding region comprised in the inventive mRNA according to the first aspect of the present invention.

According to a further preferred embodiment, the inventive mRNA can be modified by a sequence of at least 10 cytosines, preferably at least 20 cytosines, more preferably at least 30 cytosines (so-called "poly(C) sequence"). Particularly, the mRNA may contain a poly(C) sequence of typically about 10 to 200 cytosine nucleotides, preferably about 10 to 100 cytosine nucleotides, more preferably about 10 to 70 cytosine nucleotides or even more preferably about 20 to 50 or even 20 to 30 cytosine nucleotides. This poly(C) sequence is preferably located 3' of the coding region, more preferably 3' of an optional poly(A) sequence comprised in the inventive mRNA according to the first aspect of the present invention.

In this context, the inventive mRNA sequence may comprise in a specific embodiment:

a.) a 5'-CAP structure, preferably m7GpppN;
b.) a coding region encoding at least one antigenic peptide or protein of Respiratory syncytial virus (RSV), preferably derived from the fusion protein F of Respiratory syncytial virus (RSV);
c.) a poly(A) sequence preferably comprising 64 adenosines; and
d.) optionally, a poly(C) sequence, preferably comprising 30 cytosines.

In a particularly preferred embodiment of the first aspect of the present invention the inventive mRNA comprising a coding region encoding at least one antigenic peptide or protein of Respiratory syncytial virus (RSV) or a fragment, variant or derivative thereof, comprises preferably in 5'- to 3'-direction:

a.) a 5'-CAP structure, preferably m7GpppN;
b.) a coding region encoding at least one antigenic peptide or protein of Rabies virus, preferably derived from the glycoprotein G (RAV-G) of Rabies virus;
c.) a poly(A) sequence preferably comprising 64 adenosines;
d.) optionally, a poly(C) sequence, preferably comprising 30 cytosines; and
e.) a histone-stem-loop, preferably comprising the corresponding RNA sequence of the nucleic acid sequence according to SEQ ID NO: 30.

In a further particularly preferred embodiment of the first aspect of the present invention, the inventive mRNA comprising a coding region encoding at least one antigenic peptide or protein of Respiratory syncytial virus (RSV) or a fragment, variant or derivative thereof, comprises preferably in 5'- to 3'-direction:

a.) a 5'-CAP structure, preferably m7GpppN;
b.) a coding region encoding at least one antigenic peptide or protein of Respiratory syncytial virus (RSV), preferably derived from the fusion protein F of Respiratory syncytial virus (RSV);
c.) optionally, a 3'-UTR element derived from an alpha globin gene, preferably comprising the corresponding RNA sequence of the nucleic acid sequence according to SEQ ID NO. 29, a homolog, a fragment, or a variant thereof;
d.) a poly(A) sequence preferably comprising 64 adenosines;
e.) optionally, a poly(C) sequence, preferably comprising 30 cytosines; and
f.) a histone-stem-loop, preferably comprising the corresponding RNA sequence of the nucleic acid sequence according to SEQ ID NO: 30.

In another particular preferred embodiment, the inventive mRNA encoding at least one antigenic peptide or protein of Respiratory syncytial virus (RSV) or a fragment, variant or derivative thereof, comprises preferably in 5'- to 3'-direction:

a.) a 5'-CAP structure, preferably m7GpppN;
b.) optionally, a 5'-UTR element derived from a TOP gene, preferably derived from the corresponding RNA sequence of the nucleic acid sequence according to SEQ ID NO. 23, a homolog, a fragment, or a variant thereof;
c.) a coding region encoding at least one antigenic peptide or protein of Respiratory syncytial virus (RSV), preferably derived from the fusion protein F of Respiratory syncytial virus (RSV);
d.) optionally, a 3'UTR element derived of a gene providing a stable mRNA, preferably derived from the corresponding RNA sequence of a nucleic acid sequence according to SEQ ID NO. 25, a homolog, a fragment, or a variant thereof;
e.) a poly(A) sequence preferably comprising 64 adenosines;
f.) optionally, a poly(C) sequence, preferably comprising 30 cytosines; and
g.) a histone-stem-loop, preferably comprising the corresponding RNA sequence of the nucleic acid sequence according to SEQ ID NO: 30.

The coding region might encode at least partially one of the amino acid sequences according to SEQ ID Nos. 1-11 or fragments, variants or derivatives thereof. Furthermore, the coding region of the inventive mRNA may encode a combination of at least two of these amino acid sequences or a combination of fragments, variants or derivatives thereof. Particularly preferred in this context is a combination of fusion protein F with nucleoprotein N and a combination of fusion protein F and M2-1 protein.

Additionally the coding region might be or might comprise at least partially one of the sequences according to SEQ ID No. 12 to SEQ ID No. 22, or fragments, homologs or variants thereof. Furthermore, the mRNA might comprise a combination of at least two of these sequences or a combination of fragments, homologs or variants thereof.

For further improvement of the resistance to e.g. in vivo degradation (e.g. by an exo- or endo-nuclease), the inventive mRNA may be provided as a stabilized nucleic acid, e.g. in the form of a modified nucleic acid. According to a further embodiment of the invention it is therefore preferred that the inventive mRNA is stabilized, preferably by backbone modifications, sugar modifications and/or base modifications, more preferred stabilized by modification of the G/C-content. All of these modifications may be introduced into the inventive mRNA without impairing the mRNA's function to be translated into the antigenic function derived from the Respiratory syncytial virus (RSV) peptide or protein.

A backbone modification in the context of the present invention is preferably a modification in which phosphates of the backbone of the nucleotides contained in the inventive mRNA are chemically modified, e.g. anionic internucleoside linkage, N3'→P5' modifications, replacement of non-bridging oxygen atoms by boranes, neutral internucleoside linkage, amide linkage of the nucleosides, methylene(methylimino) linkages, formacetal and thioformacetal linkages, introduction of sulfonyl groups, or the like.

A sugar modification in the context of the present invention is preferably a chemical modification of the sugar of the nucleotides of the inventive mRNA, e.g. methylation of the ribose residue or the like.

According to another embodiment, the inventive mRNA may be modified and thus stabilized by modifying the G (guanosine)/C (cytosine) content of the mRNA, preferably of the coding region thereof.

Therein, the G/C content of the inventive mRNA, preferably of the coding region, is particularly increased compared to the G/C content of the coding region of its particular wild type coding sequence, i.e. the unmodified mRNA. However, the encoded amino acid sequence of the inventive mRNA is preferably not modified compared to the coded amino acid sequence of the particular wild type/unmodified mRNA.

The modification of the G/C-content of the inventive mRNA is based on the fact that RNA sequences having an increased G (guanosine)/C (cytosine) content are more stable than RNA sequences having an increased A (adenosine)/U (uracil) content. The codons of a coding sequence or a whole RNA might therefore be varied compared to the wild type coding sequence or mRNA, such that they include an increased amount of G/C nucleotides while the translated amino acid sequence is retained. In respect to the fact that several codons code for one and the same amino acid (so-called degeneration of the genetic code), the most favourable codons for the stability can be determined (so-called alternative codon usage). Preferably, the G/C content of the coding region of the inventive mRNA according to the invention is increased by at least 7%, more preferably by at least 15%, particularly preferably by at least 20%, compared to the G/C content of the coded region of the wild type RNA. According to a specific embodiment at least 5%, 10%, 20%, 30%, 40%, 50%, 60%, more preferably at least 70%, even more preferably at least 80% and most preferably at least 90%, 95% or even 100% of the substitutable codons in the region coding for a protein or peptide as defined herein or its fragment or variant thereof or the whole sequence of the wild type mRNA sequence or coding sequence are substituted, thereby increasing the G/C content of said sequence. In this context, it is particularly preferable to increase the G/C content of the inventive mRNA to the maximum (i.e. 100% of the substitutable codons), in particular in the coding region, compared to the wild type sequence.

According to a further preferred embodiment of the invention, the inventive mRNA is optimized for translation, preferably optimized for translation by replacing codons for less frequent tRNAs of a given amino acid by codons for more frequently occurring tRNAs of the respective amino acid. This is based on the finding that the translation efficiency is also determined by a different frequency in the occurrence of tRNAs in cells. Thus, if so-called "less frequent codons" are present in the inventive mRNA to an increased extent, the corresponding modified RNA is translated to a significantly poorer degree than in the case where codons coding for more frequent tRNAs are present. Preferably, the coding region of the inventive mRNA is modified compared to the corresponding region of the wild type RNA or coding sequence such that at least one codon of the wild type sequence which codes for a tRNA which is relatively rare or less frequent in the cell is exchanged for a codon which codes for a tRNA which is more or most frequent in the cell and carries the same amino acid as the relatively rare or less frequent tRNA. By this modification, the sequences of the inventive mRNA can be modified such that codons for which more frequently occurring tRNAs are available are inserted. In other words, according to the invention, by this modification all codons of the wild type sequence which code for a tRNA which is relatively rare in the cell can in each case be exchanged for a codon which codes for a respective tRNA which is relatively frequent in the cell and which, in each case, carries the same amino acid as the relatively rare tRNA. Furthermore, it is particularly preferable to link the sequential G/C content which is increased, in particular maximized, in the inventive mRNA with the "frequent" codons without modifying the amino acid sequence of the protein encoded by the coding region of the inventive mRNA or of the coding region. This preferred embodiment allows provision of a particularly efficiently translated and stabilized (modified) inventive mRNA.

Substitutions, additions or eliminations of bases are preferably carried out using a DNA matrix for preparation of the nucleic acid molecule by techniques of the well known site directed mutagenesis or with an oligonucleotide ligation. In such a process, for preparation of the at least one RNA of the inventive combination vaccine as defined herein a corresponding DNA molecule may be transcribed in vitro. This DNA matrix preferably comprises a suitable promoter, e.g. a T7 or SP6 promoter, for in vitro transcription, which is followed by the desired nucleotide sequence for the at least one RNA to be prepared and a termination signal for in vitro transcription. The DNA molecule, which forms the matrix of the at least one RNA of interest, may be prepared by fermentative proliferation and subsequent isolation as part of a plasmid which can be replicated in bacteria. Plasmids which may be mentioned as suitable for the present invention are e.g. the plasmids pT7 Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, FL, 2001.

In a particularly preferred embodiment, the inventive mRNA sequence according to the first aspect of the present invention comprises, preferably in 5'- to 3'-direction:
a) a 5'-CAP structure, as defined herein, preferably m7GpppN;
b) a coding region, preferably with an increased or even maximized G/C content compared with the G/C content of the coding region of the wild type mRNA, encoding at least one antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV), or a fragment, variant or derivative thereof;
c) a 3'-UTR element as defined herein, preferably derived of a gene providing a stable mRNA, most preferably the corresponding RNA sequence of the nucleic acid sequence according to SEQ ID No. 29, or a homolog, a fragment or variant thereof;
d) a poly(A) sequence, preferably consisting of 64 adenosines
e) optionally a poly(C) sequence, preferably consisting of 30 cytosines.
f) at least one histone stem-loop sequence, preferably the corresponding RNA sequence of the nucleic acid sequence according to SEQ ID NO. 30.

Most preferably, the inventive mRNA sequence of that specific embodiment comprises the sequence modifications as shown in FIG. 1 (SEQ ID NO. 31) using the example of an inventive mRNA coding for the fusion protein F of RSV long.

In a further particularly preferred embodiment, the inventive mRNA sequence according to the first aspect of the present invention comprises preferably in 5' to 3' direction:
a) a 5'-CAP structure, as defined herein, preferably m7GpppN;
b) a 5'-UTR element as defined herein, preferably a 5'-UTR element which comprises or consists of a nucleic acid sequence which is derived from the 5'-UTR of a TOP gene, preferably the 5'-UTR of human ribosomal protein Large 32 lacking the 5' terminal oligopyrimidine tract according to SEQ ID No. 23 or the corresponding RNA sequence; or a fragment, homolog or variant thereof;
c) a coding region, preferably with an increased or even maximized G/C content compared with the G/C content of the coding region of the wild type mRNA, encoding at least one antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) or a fragment, variant or derivative thereof;
d) a 3'-UTR element, preferably the 3'-UTR element of human albumin according to SEQ ID No. 24 or the corresponding RNA, or a homolog, a fragment or a variant thereof;
e) a poly(A) sequence, preferably consisting of 64 adenosines
f) optionally a poly(C) sequence, preferably consisting of 30 cytosines.
g) at least one histone stem-loop sequence, preferably the corresponding RNA sequence of the nucleic acid sequence according to SEQ ID NO. 30.

Most preferably, the inventive mRNA of that specific embodiment comprises the sequence modifications as shown in FIG. 2 (SEQ ID NO. 32) using the example of an inventive mRNA coding for the fusion protein F of RSV long.

In an even more particularly preferred embodiment the inventive mRNA sequence comprises or consists of the sequences shown in FIGS. 1-5 according to SEQ ID Nos. 31 and 35.

In further specific embodiments, the mRNA according to the invention may further comprise an internal ribosome entry site (IRES) sequence or IRES-motif, which may separate several open reading frames, for example if the inventive mRNA encodes for two or more antigenic peptides or proteins. An IRES-sequence may be particularly helpful if the mRNA is a bi- or multicistronic mRNA.

Additionally, the inventive mRNA may be prepared using any method known in the art, including synthetic methods such as e.g. solid phase synthesis, as well as in vitro methods, such as in vitro transcription reactions.

According to one embodiment of the present invention the mRNA comprising a coding region, encoding at least one antigenic peptide or protein of Respiratory syncytial virus (RSV) or a fragment, variant or derivative thereof may be administered naked without being associated with any further vehicle, transfection or complexation agent for increasing the transfection efficiency and/or the immunostimulatory properties of the inventive mRNA or of further comprised nucleic acid.

In a preferred embodiment, the inventive mRNA may be formulated together with a cationic or polycationic compound and/or with a polymeric carrier. Accordingly, in a further embodiment of the invention it is preferred that the inventive mRNA or any other nucleic acid comprised in the inventive pharmaceutical composition or vaccine is associated with or complexed with a cationic or polycationic compound or a polymeric carrier, optionally in a weight ratio selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w) of mRNA or nucleic acid to cationic or polycationic compound and/or with a polymeric carrier; or optionally in a nitrogen/phosphate ratio of mRNA or nucleic acid to cationic or polycationic compound and/or polymeric carrier in the range of about 0.1-10, preferably in a range of about 0.3-4 or 0.3-1, and most preferably in a range of about 0.5-1 or 0.7-1, and even most preferably in a range of about 0.3-0.9 or 0.5-0.9.

Thereby, the inventive mRNA or any other nucleic acid comprised in the inventive pharmaceutical composition or vaccine can also be associated with a vehicle, transfection or complexation agent for increasing the transfection efficiency and/or the immunostimulatory properties of the inventive mRNA or of optionally comprised further included nucleic acids.

Cationic or polycationic compounds, being particularly preferred agents in this context include protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, pIsl, FGF, Lactoferrin, Transportan, Buforin-2, Bac715-24, SynB, SynB(1), pVEC, hCT-derived peptides, SAP, or histones.

In this context, protamine is particularly preferred.

Additionally, preferred cationic or polycationic proteins or peptides may be selected from the following proteins or peptides having the following total formula (III):

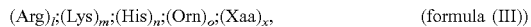

$(Arg)_l;(Lys)_m;(His)_n;(Orn)_o;(Xaa)_x,$ (formula (III))

wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc. In this context the disclosure of WO 2009/030481 is incorporated herewith by reference.

Further preferred cationic or polycationic compounds, which can be used as transfection or complexation agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-((α-trimethylammonioacetyl) diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl] trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

A polymeric carrier used according to the invention might be a polymeric carrier formed by disulfide-crosslinked cationic components. The disulfide-crosslinked cationic components may be the same or different from each other. The polymeric carrier can also contain further components. It is also particularly preferred that the polymeric carrier used according to the present invention comprises mixtures of cationic peptides, proteins or polymers and optionally further components as defined herein, which are crosslinked by disulfide bonds as described herein. In this context, the disclosure of WO 2012/013326 is incorporated herewith by reference.

In this context, the cationic components, which form basis for the polymeric carrier by disulfide-crosslinkage, are typically selected from any suitable cationic or polycationic peptide, protein or polymer suitable for this purpose, particular any cationic or polycationic peptide, protein or polymer capable to complex an mRNA or a nucleic acid as defined according to the present invention, and thereby preferably condensing the mRNA or the nucleic acid. The cationic or polycationic peptide, protein or polymer, is preferably a linear molecule, however, branched cationic or polycationic peptides, proteins or polymers may also be used.

Every disulfide-crosslinking cationic or polycationic protein, peptide or polymer of the polymeric carrier, which may be used to complex the inventive mRNA or any further nucleic acid comprised in the inventive pharmaceutical composition or vaccine contains at least one —SH moiety, most preferably at least one cysteine residue or any further chemical group exhibiting an —SH moiety, capable to form a disulfide linkage upon condensation with at least one further cationic or polycationic protein, peptide or polymer as cationic component of the polymeric carrier as mentioned herein.

As defined above, the polymeric carrier, which may be used to complex the inventive mRNA or any further nucleic acid comprised in the inventive pharmaceutical composition or vaccine may be formed by disulfide-crosslinked cationic (or polycationic) components.

Preferably, such cationic or polycationic peptides or proteins or polymers of the polymeric carrier, which comprise or are additionally modified to comprise at least one —SH moiety, are selected from, proteins, peptides and polymers as defined above for complexation agent.

In a further particular embodiment, the polymeric carrier which may be used to complex the inventive mRNA or any further nucleic acid comprised in the inventive pharmaceutical composition or vaccine may be selected from a polymeric carrier molecule according to generic formula (IV):

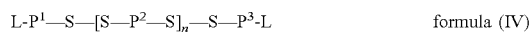

$L-P^1—S—[S—P^2—S]_n—S—P^3-L$ (formula (IV))

wherein, $P^1$ and $P^3$ are different or identical to each other and represent a linear or branched hydrophilic polymer chain, each $P^1$ and $P^3$ exhibiting at least one —SH-moiety, capable to form a disulfide linkage upon condensation with component $P^2$, or alternatively with (AA), $(AA)_x$, or $[(AA)_x]_z$ if such components are used as a linker between $P^1$ and $P^2$ or $P^3$ and $P^2$) and/or with further components (e.g. (AA), (AA)$_x$, [(AA)$_x$]$_z$ or L), the linear or branched hydrophilic polymer chain selected independent from each other from polyethylene glycol (PEG), poly-N-(2-hydroxypropyl)methacrylamide, poly-2-(methacryloyloxy)ethyl phosphorylcholines, poly(hydroxyalkyl L-asparagine), poly(2-(methacryloyloxy)ethyl phosphorylcholine), hydroxyethylstarch or poly(hydroxyalkyl L-glutamine), wherein the hydrophilic polymer chain exhibits a molecular weight of about 1 kDa to about 100 kDa, preferably of about 2 kDa to about 25 kDa; or more preferably of about 2 kDa to about 10 kDa, e.g. about 5 kDa to about 25 kDa or 5 kDa to about 10 kDa;

P$^2$ is a cationic or polycationic peptide or protein, e.g. as defined above for the polymeric carrier formed by disulfide-crosslinked cationic components, and preferably having a length of about 3 to about 100 amino acids, more preferably having a length of about 3 to about 50 amino acids, even more preferably having a length of about 3 to about 25 amino acids, e.g. a length of about 3 to 10, 5 to 15, 10 to 20 or 15 to 25 amino acids, more preferably a length of about 5 to about 20 and even more preferably a length of about 10 to about 20; or is a cationic or polycationic polymer, e.g. as defined above for the polymeric carrier formed by disulfide-crosslinked cationic components, typically having a molecular weight of about 0.5 kDa to about 30 kDa, including a molecular weight of about 1 kDa to about 20 kDa, even more preferably of about 1.5 kDa to about 10 kDa, or having a molecular weight of about 0.5 kDa to about 100 kDa, including a molecular weight of about 10 kDa to about 50 kDa, even more preferably of about 10 kDa to about 30 kDa;

each P$^2$ exhibiting at least two —SH-moieties, capable to form a disulfide linkage upon condensation with further components P$^2$ or component(s) P$^1$ and/or P$^3$ or alternatively with further components (e.g. (AA), (AA)$_x$, or [(AA)$_x$]$_z$);

—S—S— is a (reversible) disulfide bond (the brackets are omitted for better readability), wherein S preferably represents sulphur or a —SH carrying moiety, which has formed a (reversible) disulfide bond. The (reversible) disulfide bond is preferably formed by condensation of —SH-moieties of either components P$^1$ and P$^2$, P$^2$ and P$^2$, or P$^2$ and P$^3$, or optionally of further components as defined herein (e.g. L, (AA), (AA)$_x$, [(AA)$_x$]$_z$, etc); The —SH-moiety may be part of the structure of these components or added by a modification as defined below;

L is an optional ligand, which may be present or not, and may be selected independent from the other from RGD, Transferrin, Folate, a signal peptide or signal sequence, a localization signal or sequence, a nuclear localization signal or sequence (NLS), an antibody, a cell penetrating peptide, (e.g. TAT or KALA), a ligand of a receptor (e.g. cytokines, hormones, growth factors etc), small molecules (e.g. carbohydrates like mannose or galactose or synthetic ligands), small molecule agonists, inhibitors or antagonists of receptors (e.g. RGD peptidomimetic analogues), or any further protein as defined herein, etc.;

n is an integer, typically selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 4 to 9, 4 to 10, 3 to 20, 4 to 20, 5 to 20, or 10 to 20, or a range of about 3 to 15, 4 to 15, 5 to 15, or 10 to 15, or a range of about 6 to 11 or 7 to 10. Most preferably, n is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

In this context the disclosure of WO 2011/026641 is incorporated herewith by reference. Each of hydrophilic polymers P$^1$ and P$^3$ typically exhibits at least one —SH-moiety, wherein the at least one —SH-moiety is capable to form a disulfide linkage upon reaction with component P$^2$ or with component (AA) or (AA)$_x$, if used as linker between P$^1$ and P$^2$ or P$^3$ and P$^2$ as defined below and optionally with a further component, e.g. L and/or (AA) or (AA)$_x$, e.g. if two or more —SH-moieties are contained. The following subformulae "P$^1$—S—S—P$^2$" and "P$^2$—S—S—P$^3$" within generic formula (V) above (the brackets are omitted for better readability), wherein any of S, P$^1$ and P$^3$ are as defined herein, typically represent a situation, wherein one-SH-moiety of hydrophilic polymers P$^1$ and P$^3$ was condensed with one —SH-moiety of component P$^2$ of generic formula (V) above, wherein both sulphurs of these —SH-moieties form a disulfide bond —S—S— as defined herein in formula (V). These —SH-moieties are typically provided by each of the hydrophilic polymers P$^1$ and P$^3$, e.g. via an internal cysteine or any further (modified) amino acid or compound which carries a —SH moiety. Accordingly, the subformulae "P$^1$—S—S—P$^2$" and "P$^2$—S—S—P$^3$" may also be written as "P$^1$-Cys-Cys-P$^2$" and "P$^2$-Cys-Cys-P$^3$", if the —SH— moiety is provided by a cysteine, wherein the term Cys-Cys represents two cysteines coupled via a disulfide bond, not via a peptide bond. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their —SH-moieties to form a disulfide bond. Accordingly, the term "-Cys-Cys-" also may be understood generally as "-(Cys-S)—(S-Cys)-", wherein in this specific case S indicates the sulphur of the —SH-moiety of cysteine. Likewise, the terms "—S-Cys" and "—Cys-S" indicate a disulfide bond between a —SH containing moiety and a cysteine, which may also be written as "—S—(S-Cys)" and "-(Cys-S)—S". Alternatively, the hydrophilic polymers P$^1$ and P$^3$ may be modified with a —SH moiety, preferably via a chemical reaction with a compound carrying a —SH moiety, such that each of the hydrophilic polymers P$^1$ and P$^3$ carries at least one such —SH moiety. Such a compound carrying a —SH moiety may be e.g. an (additional) cysteine or any further (modified) amino acid, which carries a —SH moiety. Such a compound may also be any non-amino compound or moiety, which contains or allows to introduce a —SH moiety into hydrophilic polymers P$^1$ and P$^3$ as defined herein. Such non-amino compounds may be attached to the hydrophilic polymers P$^1$ and P$^3$ of formula (VI) of the polymeric carrier according to the present invention via chemical reactions or binding of compounds, e.g. by binding of a 3-thio propionic acid or thioimolane, by amide formation (e.g. carboxylic acids, sulphonic acids, amines, etc), by Michael addition (e.g maleinimide moieties, α,β unsatured carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow Sn-type substitution reactions (e.g halogenalkans, thiols, alcohols, amines, hydrazines, hydrazides, sulphonic acid esters, oxyphosphonium salts) or other chemical moieties which can be utilized in the attachment of further components. A particularly preferred PEG derivate in this context is alpha-Methoxy-omega-mercapto poly(ethylene glycol). In each case, the SH-moiety, e.g. of a cysteine or of any further (modified) amino acid or compound, may be present at the terminal ends or internally at any position of hydrophilic polymers $P^1$ and $P^3$. As defined herein, each of hydrophilic polymers $P^1$ and $P^3$ typically exhibits at least one —SH— moiety preferably at one terminal end, but may also contain two or even more —SH-moieties, which may be used to additionally attach further components as defined herein, preferably further functional peptides or proteins e.g. a ligand, an amino acid component (AA) or (AA)$_x$, antibodies, cell penetrating peptides or enhancer peptides (e.g. TAT, KALA), etc.

In this context, it is particularly preferred that the inventive mRNA is complexed at least partially with a cationic or polycationic compound and/or a polymeric carrier, preferably cationic proteins or peptides. In this context the disclosure of WO 2010/037539 and WO 2012/113513 is incorporated herewith by reference. Partially means that only a part of the inventive mRNA is complexed with a cationic compound and that the rest of the inventive mRNA is (comprised in the inventive pharmaceutical compostion or vaccine) in uncomplexed form ("free"). Preferably the ratio of complexed mRNA to:free mRNA (in the inventive pharmaceutical composition or vaccine) is selected from a range of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed mRNA to free mRNA in the inventive pharmaceutical composition or vaccine is selected from a ratio of about 1:1 (w/w).

The complexed mRNA in the inventive pharmaceutical composition or vaccine, is preferably prepared according to a first step by complexing the inventive mRNA with a cationic or polycationic compound and/or with a polymeric carrier, preferably as defined herein, in a specific ratio to form a stable complex. In this context, it is highly preferable, that no free cationic or polycationic compound or polymeric carrier or only a negligibly small amount thereof remains in the component of the complexed mRNA after complexing the mRNA. Accordingly, the ratio of the mRNA and the cationic or polycationic compound and/or the polymeric carrier in the component of the complexed mRNA is typically selected in a range that the mRNA is entirely complexed and no free cationic or polycationic compound or polymeric carrier or only a negligibly small amount thereof remains in the composition.

Preferably the ratio of the mRNA to the cationic or polycationic compound and/or the polymeric carrier, preferably as defined herein, is selected from a range of about 6:1 (w/w) to about 0,25:1 (w/w), more preferably from about 5:1 (w/w) to about 0,5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w). Alternatively, the ratio of the mRNA to the cationic or polycationic compound and/or the polymeric carrier, preferably as defined herein, in the component of the complexed mRNA, may also be calculated on the basis of the nitrogen/phosphate ratio (N/P-ratio) of the entire complex. In the context of the present invention, an N/P-ratio is preferably in the range of about 0.1-10, preferably in a range of about 0.3-4 and most preferably in a range of about 0.5-2 or 0.7-2 regarding the ratio of mRNA:cationic or polycationic compound and/or polymeric carrier, preferably as defined herein, in the complex, and most preferably in a range of about 0.7-1,5, 0.5-1 or 0.7-1, and even most preferably in a range of about 0.3-0.9 or 0.5-0.9., preferably provided that the cationic or polycationic compound in the complex is a cationic or polycationic cationic or polycationic protein or peptide and/or the polymeric carrier as defined above. In this specific embodiment the complexed mRNA is also emcompassed in the term "adjuvant component".

In a further aspect, the invention provides for a composition comprising a plurality or more than one, preferably 2 to 10, more preferably 2 to 5, most preferably 2 to 4 of the inventive mRNA sequences as defined herein. These inventive compositions comprise more than one inventive mRNA sequences, preferably encoding different peptides or proteins which comprise preferably different pathogenic antigens or fragments, variants or derivatives thereof. Particularly preferred in this context is that at least one mRNA sequence encodes at least one antigenic peptide or protein derived from the fusion protein F of Respiratory syncytial virus (RSV) and that at least one mRNA sequence encodes at least one antigenic peptide or protein derived from another antigen of Respiratory syncytial virus (RSV), particularly of nucleoprotein N or M2-1 protein. Further particularly preferred combinations of antigens are in this context:

F+G (serotype A)+G (serotype B)
F+G (serotype A)+G (serotype B)+M2-1
F+G (serotype A)+G (serotype B)+N
F+G (serotype A)+G (serotype B)+N+M2-1
F+M2–1+N
SF+M2–1
F+N
F+G (serotype A)+G (serotype B)+N+M2–1+P+M2–2+M+L
F+G (serotype A)+G (serotype B)+N+M2–1+ P+M2–2+M
F+G (serotype A)+G (serotype B)+N+M2–1+ P+M2-2+L
F+G (serotype A)+G (serotype B)+N+M2–1+ P+M+L
F+G (serotype A)+G (serotype B)+N+M2–1+ M2–2+M+L
F+G (serotype A)+G (serotype B)+N+P+M2–2+M+L
F+G (serotype A)+G (serotype B)+M2–1+ P+M2–2+M+L Accordingly, in a further particular preferred aspect, the present invention also provides a pharmaceutical composition, comprising at least one inventive mRNA sequence as defined herein or an inventive composition comprising a plurality of inventive mRNA sequences as defined herein and optionally a pharmaceutically acceptable carrier and/or vehicle.

As a first ingredient, the inventive pharmaceutical composition comprises at least one inventive mRNA sequence as defined herein.

As a second ingredient, the inventive pharmaceutical composition may optionally comprise at least one additional pharmaceutically active component. A pharmaceutically active component in this connection is a compound that has a therapeutic effect to heal, ameliorate or prevent a particular indication or disease as mentioned herein, preferably RSV infections. Such compounds include, without implying any limitation, peptides or proteins, preferably as defined herein, nucleic acids, preferably as defined herein, (therapeutically active) low molecular weight organic or inorganic compounds (molecular weight less than 5000, preferably less than 1000), sugars, antigens or antibodies, preferably as defined herein, therapeutic agents already known in the prior art, antigenic cells, antigenic cellular fragments, cellular fractions; cell wall components (e.g. polysaccharides), modified, attenuated or de-activated (e.g. chemically or by irradiation) pathogens (virus, bacteria etc.), adjuvants, preferably as defined herein, etc. Particularly preferred in this context are RSV vaccines, or RSV immune globulines, e.g. Palivizumab (Synagis®).

The inventive pharmaceutical composition may be administered orally, parenterally, by inhalation spray, topically, rectally, nasally, buccally, vaginally or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Particularly preferred is intradermal and intramuscular injection. Sterile injectable forms of the inventive pharmaceutical compositions may be aqueous or oleaginous suspension. These suspensions may be formulated according to techniques known in the art using suitable dispersing or wetting agents and suspending agents.

In a preferred embodiment, the inventive pharmaceutical composition is administered via intradermal or intramuscular injection, preferably by using conventional needle-based injection technique or by using a needle-free system, e.g. jet injection. In a further preferred embodiment, the inventive pharmaceutical composition may be administered by jet injection as defined herein. Preferably, the inventive pharmaceutical composition may be adminstered intramuscularly by jet injection. According to another embodiment, the pharmaceutical composition is administered intradermally via jet injection.

In a preferred embodiment, the pharmaceutical composition may be administered once, twice or three times, preferably by intradermal or intramuscular injection, preferably by jet injection. According to a certain embodiment, a single administration of the inventive pharmaceutical composition, preferably via intradermal or intramuscular injection, preferably by using jet injection, is sufficient for eliciting an immune response against the at least one antigen encoded by the mRNA sequence according to the invention. In a preferred embodiment, the single administration of the pharmaceutical composition elicits an immune response resulting in virus neutralisation. In this context, one single intradermal or intramuscular injection of the pharmaceutical composition is particularly preferred. Preferably, further administrations of the pharmaceutical composition may optionally be carried out in order to enhance and/or prolong the immune response.

According to a specific embodiment, the inventive pharmaceutical composition may comprise an adjuvant. In this context, an adjuvant may be understood as any compound, which is suitable to initiate or increase an immune response of the innate immune system, i.e. a non-specific immune response. With other words, when administered, the inventive pharmaceutical composition preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following.

Particularly preferred as adjuvants suitable for depot and delivery are cationic or polycationic compounds as defined above for the inventive mRNA sequence as vehicle, transfection or complexation agent.

Furthermore, the inventive pharmaceutical composition may comprise one or more additional adjuvants, which are suitable to initiate or increase an immune response of the innate immune system, i.e. a non-specific immune response, particularly by binding to pathogen-associated molecular patterns (PAMPs). With other words, when administered, the pharmaceutical composition or vaccine preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following. According to one embodiment such an adjuvant may be selected from an adjuvant as defined above.

Also such an adjuvant may be selected from any adjuvant known to a skilled person and suitable for the present case, i.e. supporting the induction of an innate immune response in a mammal and/or suitable for depot and delivery of the components of the inventive pharmaceutical composition or vaccine. Preferred as adjuvants suitable for depot and delivery are cationic or polycationic compounds as defined above. Likewise, the adjuvant may be selected from the group consisting of, e.g., cationic or polycationic compounds as defined above, from chitosan, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylaminob-D-glucopyranosyl)-N-octadecyl-dodecanoyl-amide hydroacetate); CALCITRIOL™ (1-alpha, 25-dihydroxy-vitamin D3); calcium phosphate gel; CAP™ (calcium phosphate nanoparticles); cholera holotoxin, cholera-toxin-Al-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D35 glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L47 alanyl-D-isoglutamine); imiquimod (1-(2-methypropyl)-1H-imidazo[4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferongamma; interleukin-1beta; interleukin-2; interleukin-7; interleukin-12; ISCOMS™; ISCOPREP 7.0.3.™; liposomes; LOXORIBINE™ (7-allyl-8-oxoguanosine); LT 5 oral adjuvant (*E. coli* labile enterotoxin-protoxin); microspheres and microparticles of any composition; MF59™; (squalenewater emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH3); MURAPALMITINE™ and DMURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (☐β-glucan); PLGA, PGA and PLA (homo- and co-polymers of lactic acid and glycolic acid; microspheres/nanospheres); PLURONIC L121™; PMMA (polymethylmethacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, AL); STIMULON™ (QS-21); Quil-A (Quil-A saponin); S-28463 (4-amino-otec-dimethyl-2-ethoxymethyl-1H-imidazo[4,5-c]quinoline-1-ethanol); SAF-1™ ("Syntex adjuvant formulation"); Sendai proteoliposomes and Sendai containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Aladipalmitoxypropylamide); Theronyl-MDP (Termurtide™ or [thr 1]-MDP; N-acetylmuramyl-Lthreonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin, microbe derived adjuvants, including Romurtide, DETOX, MPL, CWS, Mannose, CpG nucleic acid sequences, CpG7909, ligands of human TLR 1-10, ligands of murine TLR 1-13, ISS-1018, 35 IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

Particularly preferred, an adjuvant may be selected from adjuvants, which support induction of a Th1-immune response or maturation of naïve T-cells, such as GM-CSF, IL-12, IFNg, any immunostimulatory nucleic acid as defined above, preferably an immunostimulatory RNA, CpG DNA, etc.

In a further preferred embodiment, it is also possible that the inventive pharmaceutical composition contains besides the antigen-providing mRNA further components, which are selected from the group comprising: further antigens or further antigen-providing nucleic acids; a further immunotherapeutic agent; one or more auxiliary substances; or any further compound, which is known to be immunostimulating due to its binding affinity (as ligands) to human Toll-like receptors; and/or an adjuvant nucleic acid, preferably an immunostimulatory RNA (isRNA).

The inventive pharmaceutical composition can additionally contain one or more auxiliary substances in order to increase its immunogenicity or immunostimulatory capacity, if desired. A synergistic action of the inventive mRNA sequence as defined herein and of an auxiliary substance, which may be optionally contained in the inventive pharmaceutical composition, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta or TNF-alpha, growth factors, such as hGH.

Further additives, which may be included in the inventive pharmaceutical composition, are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive pharmaceutical composition can also additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

In this context, it is particularly preferred that the optionally comprised adjuvant component comprises the same inventive mRNA as comprised in the inventive pharmaceutical composition as antigen-providing mRNA e.g. mRNA coding for an antigenic peptide or protein of RSV infections Respiratory syncytial virus (RSV) or fragments, variants or derivatives thereof.

Despite, the inventive pharmaceutical composition may comprise further components for facilitating administration and uptake of components of the pharmaceutical composition. Such further components may be an appropriate carrier or vehicle, additional adjuvants for supporting any immune response, antibacterial and/or antiviral agents.

Accordingly, in a further embodiment, the inventive pharmaceutical composition furthermore comprises a pharmaceutically acceptable carrier and/or vehicle.

Such a pharmaceutically acceptable carrier typically includes the liquid or non-liquid basis of a composition comprising the components of the inventive pharmaceutical composition. If the composition is provided in liquid form, the carrier will typically be pyrogen-free water; isotonic saline or buffered (aqueous) solutions, e.g. phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds, which are suitable for administration to a patient to be treated, may be used as well for the pharmaceutical composition according to the invention. The term "compatible" as used here means that these constituents of the inventive pharmaceutical composition are capable of being mixed with the components of the inventive pharmaceutical composition in such a manner that no interaction occurs which would substantially reduce the pharmaceutical effectiveness of the pharmaceutical composition under typical use conditions.

A further component of the inventive pharmaceutical composition may be an immunotherapeutic agent that can be selected from immunoglobulins, preferably IgGs, monoclonal or polyclonal antibodies, polyclonal serum or sera, etc, most preferably immunoglobulins directed against Respiratory syncytial virus (RSV), e.g. Palivizumab. Preferably, such a further immunotherapeutic agent may be provided as a peptide/protein or may be encoded by a nucleic acid, preferably by a DNA or an RNA, more preferably an mRNA. Such an immunotherapeutic agent allows providing passive vaccination additional to active vaccination triggered by the inventive antigen-providing mRNA.

Furthermore, in a specific embodiment, additionally to the antigen-providing mRNA further antigens can be included in the inventive pharmaceutical composition and are typically substances such as cells, cell lysates, viruses, attenuated viruses, inactivated viruses, proteins, peptides, nucleic acids or other bio- or macromolecules or fragments thereof. Preferably, antigens may be proteins and peptides or fragments thereof, such as epitopes of those proteins or peptides, preferably having 5 to 15, more preferably 6 to 9, amino acids. Particularly, said proteins, peptides or epitopes may be derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV), or from fragments, variants or derivatives thereof. Further, antigens may also comprise any other biomolecule, e.g., lipids, carbohydrates, etc. Preferably, the antigen is a protein or (poly-) peptide antigen, a nucleic acid, a nucleic acid encoding a protein or (poly-) peptide antigen, a polysaccharide antigen, a polysaccharide conjugate antigen, a lipid antigen, a glycolipid antigen, a carbohydrate antigen, a bacterium, a cell (vaccine), or killed or attenuated viruses.

The inventive pharmaceutical composition or vaccine as defined herein may furthermore comprise further additives or additional compounds. Further additives, which may be included in the pharmaceutical composition, are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives, RNase inhibitors and/or an anti-bacterial agent or an anti-viral agent. Additionally the inventive pharmaceutical composition may comprise small interfering RNA (siRNA) directed against genes of Respiratory syncytial virus (RSV), e.g. siRNA directed against the gene encoding the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV). The inventive pharmaceutical composition typically comprises a "safe and effective amount" of the components of the inventive pharmaceutical composition, particularly of the inventive mRNA sequence(s) as defined herein. As used herein, a "safe and effective amount" means an amount of the inventive mRNA sequence(s) as defined herein as such that is sufficient to significantly induce a positive modification of a disease or disorder or to prevent a disease, preferably RSV infections as defined herein. At the same time, however, a "safe and effective amount" is small enough to avoid serious side-effects and to permit a sensible relationship between advantage and risk. The determination of these limits typically lies within the scope of sensible medical judgment.

The inventive pharmaceutical composition may be used for human and also for veterinary medical purposes, preferably for human medical purposes, as a pharmaceutical composition in general or as a vaccine.

According to another particularly preferred aspect, the inventive pharmaceutical composition (or the inventive mRNA sequence as defined herein or the inventive composition comprising a plurality of inventive mRNA sequences as defined herein) may be provided or used as a vaccine. Typically, such a vaccine is as defined above for pharmaceutical compositions. Additionally, such a vaccine typically contains the inventive mRNA sequence as defined herein or the inventive composition comprising a plurality of inventive mRNA sequences as defined herein.

The inventive vaccine may also comprise a pharmaceutically acceptable carrier, adjuvant, and/or vehicle as defined herein for the inventive pharmaceutical composition. In the specific context of the inventive vaccine, the choice of a pharmaceutically acceptable carrier is determined in principle by the manner in which the inventive vaccine is administered. The inventive vaccine can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, vaccines may be administered by an intradermal, subcutaneous, or intramuscular route. Inventive vaccines are therefore preferably formulated in liquid (or sometimes in solid) form.

In a preferred embodiment, the inventive vaccine is administered via intradermal or intramuscular injection, preferably by using conventional needle-based injection technique or by using a needle-free system, e.g. jet injection. In a further preferred embodiment, the inventive vaccine may be administered by jet injection as defined herein. Preferably, the inventive vaccine is adminstered intramuscularly by jet injection. According to another embodiment, the vaccine is administered intradermally via jet injection.

In a preferred embodiment, the vaccine may be administered once, twice or three times, preferably by intradermal or intramuscular injection, preferably by jet injection. According to a certain embodiment, a single administration of the inventive vaccine, preferably via intradermal or intramuscular injection, preferably by using jet injection, is sufficient for eliciting an immune response against the at least one antigen encoded by the mRNA sequence according to the invention. In a preferred embodiment, the single administration of the vaccine elicits an immune response resulting in virus neutralisation. In this context, one single intradermal or intramuscular injection of the vaccine is particularly preferred. Preferably, further administrations of the vaccine may optionally be carried out in order to enhance and/or prolong the immune response.

The inventive vaccine can additionally contain one or more auxiliary substances in order to increase its immunogenicity or immunostimulatory capacity, if desired. Particularly preferred are adjuvants as auxiliary substances or additives as defined for the pharmaceutical composition.

In a further aspect, the invention is directed to a kit or kit of parts comprising the components of the inventive mRNA sequence, the inventive composition comprising a plurality of inventive mRNA sequences, the inventive pharmaceutical composition or vaccine and optionally technical instructions with information on the administration and dosage of the components.

Beside the components of the inventive mRNA sequence, the inventive composition comprising a plurality of inventive mRNA sequences, the inventive pharmaceutical composition or vaccine the kit may additionally contain a pharmaceutically acceptable vehicle, an adjuvant and at least one further component as defined herein, as well as means for administration and technical instructions. The components of the inventive mRNA sequence, the inventive composition comprising a plurality of inventive mRNA sequences, the inventive pharmaceutical composition or vaccine and e.g. the adjuvant may be provided in lyophilized form. In a preferred embodiment, prior to use of the kit for vaccination, the provided vehicle is than added to the lyophilized components in a predetermined amount as written e.g. in the provided technical instructions. By doing so the inventive mRNA sequence, the inventive composition comprising a plurality of inventive mRNA sequences, the inventive pharmaceutical composition or vaccine, according to the above described aspects of the invention is provided that can afterwards be used in a method as described above, also.

The present invention furthermore provides several applications and uses of the inventive mRNA sequence as defined herein, of the inventive composition comprising a plurality of inventive mRNA sequences as defined herein, of the inventive pharmaceutical composition, of the inventive vaccine, all comprising the inventive mRNA sequence as defined herein or of kits comprising same.

In a further aspect, the invention provides an mRNA sequence encoding at least one antigenic peptide or protein of Respiratory syncytial virus (RSV), or a fragment, variant or derivative thereof, and a composition, a pharmaceutical composition, a vaccine and a kit, all comprising the mRNA sequence for use in a method of prophylactic and/or therapeutic treatment of RSV infections. Consequently, in a further aspect, the present invention is directed to the first medical use of the inventive mRNA sequence, the inventive composition comprising a plurality of inventive mRNA sequences, the inventive pharmaceutical composition, the inventive vaccine, and the inventive kit as defined herein as a medicament. Particularly, the invention provides the use of an mRNA sequence encoding at least one antigenic peptide or protein of Respiratory syncytial virus (RSV), or a fragment, variant or derivative thereof as defined above for the preparation of a medicament.

According to another aspect, the present invention is directed to the second medical use of the mRNA sequence encoding at least one antigenic peptide or protein of Respiratory syncytial virus (RSV), or a fragment, variant or derivative thereof, as defined herein, optionally in form of a composition comprising a plurality of inventive mRNA sequences, a pharmaceutical composition or vaccine, kit or kit of parts, for the treatment of RSV infections as defined herein. Particularly, the mRNA sequence encoding at least one antigenic peptide or protein of Respiratory syncytial virus (RSV), or a fragment, variant or derivative thereof to be used in a method as said above is a mRNA sequence formulated together with a pharmaceutically acceptable vehicle and an optionally additional adjuvant and an optionally additional further component as defined above e.g. a further antigen or a RSV immune globuline. In this context particularly the (prophylactic) treatment of infants, the elderly and immunocompromised patients is preferred. And even more preferred is the (prophylactic) treatment of preterm infants and infants with chronic lung disease.

The inventive mRNA sequence may alternatively be provided such that it is administered for preventing or treating RSV infections by several doses, each dose containing the inventive mRNA sequence encoding at least one antigenic peptide or protein of RSV infections Respiratory syncytial virus (RSV), or a fragment, variant or derivative thereof, e.g. the first dose containing at least one mRNA encoding at least one antigenic peptide or protein derived from the fusion protein F (or fragments, variants or derivatives thereof) and the second dose containing at least one mRNA sequence encoding at least one antigenic peptide or protein derived from a different antigen of Respiratory syncytial virus (RSV), preferably from the nucleoprotein N (or fragments, variants or derivatives thereof), from the M2-1 protein or the glycoprotein G (or fragments, variants or derivatives thereof). By that embodiment, both doses are administered in a staggered way, i.e. subsequently, shortly one after the other, e.g. within less than 10 minutes, preferably less than 2 minutes, and at the same site of the body to achieve the same immunological effect as for administration of one single composition containing both, e.g. the mRNA encoding the fusion protein F and the mRNA encoding the nucleoprotein N.

According to a specific embodiment, the inventive mRNA sequence, or the inventive pharmaceutical composition or vaccine may be administered to the patient as a single dose. In certain embodiments, the inventive mRNA sequence or the inventive pharmaceutical composition or vaccine may be administered to a patient as a single dose followed by a second dose later and optionally even a third, fourth (or more) dose subsequent thereto etc. In accordance with this embodiment, booster inoculations with the inventive mRNA sequence or the inventive pharmaceutical composition or vaccine may be administered to a patient at specific time intervals, preferably as defined below, following the second (or third, fourth, etc.) inoculation. In this context, it is particularly preferred that several doses comprise the same mRNA sequence encoding the same antigenic peptide or protein of Respiratory syncytial virus (RSV), e.g. fusion protein F. In that embodiment the doses are given in a specific time period e.g. 20-30 days. For example for postexposure prophylaxis at least 5 doses of the inventive mRNA sequence or inventive pharmaceutical composition or vaccine can be administered in 20-30 days.

In a preferred embodiment, inventive mRNA sequence, inventive pharmaceutical composition or vaccine is administered via intradermal or intramuscular injection, preferably by using conventional needle-based injection technique or by using a needle-free system, e.g. jet injection. In a further preferred embodiment, the inventive mRNA sequence, inventive pharmaceutical composition or vaccine may be administered by jet injection as defined herein. Preferably, the inventive mRNA sequence, inventive pharmaceutical composition or vaccine is adminstered intramuscularly by jet injection. According to another embodiment, the inventive mRNA sequence, inventive pharmaceutical composition or vaccine is administered intradermally via jet injection.

In a preferred embodiment, the inventive mRNA sequence, inventive pharmaceutical composition or vaccine may be administered once, twice or three times, preferably by intradermal or intramuscular injection, preferably by jet injection. According to a certain embodiment, a single administration of the the inventive mRNA sequence, inventive pharmaceutical composition or vaccine, preferably via intradermal or intramuscular injection, preferably by using jet injection, is sufficient for eliciting an immune response against the at least one antigen encoded by the mRNA sequence according to the invention. In a preferred embodiment, the single administration of the inventive mRNA sequence, inventive pharmaceutical composition or vaccine elicits an immune response resulting in virus neutralisation. In this context, one single intradermal or intramuscular injection of the inventive mRNA sequence, inventive pharmaceutical composition or vaccine is particularly preferred. Preferably, further administrations of the inventive mRNA sequence, inventive pharmaceutical composition or vaccine may optionally be carried out in order to enhance and/or prolong the immune response.

In certain embodiments, such booster inoculations with the inventive mRNA sequence or inventive pharmaceutical composition or vaccine may utilize an additional compound or component as defined for the inventive mRNA sequence or inventive pharmaceutical composition or vaccine as defined herein.

According to a further aspect, the present invention also provides a method for expression of an encoded antigenic peptide or protein derived from the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of Respiratory syncytial virus (RSV) comprising the steps, e.g. a) providing the inventive mRNA sequence as defined herein or the inventive composition comprising a plurality of inventive mRNA sequences as defined herein, b) applying or administering the inventive mRNA sequence as defined herein or the inventive composition comprising a plurality of inventive mRNA sequences as defined herein to an expression system, e.g. to a cell-free expression system, a cell (e.g. an expression host cell or a somatic cell), a tissue or an organism. The method may be applied for laboratory, for research, for diagnostic, for commercial production of peptides or proteins and/or for therapeutic purposes. In this context, typically after preparing the inventive mRNA sequence as defined herein or of the inventive composition comprising a plurality of inventive mRNA sequences as defined herein, it is typically applied or administered to a cell-free expression system, a cell (e.g. an expression host cell or a somatic cell), a tissue or an organism, e.g. in naked or complexed form or as a pharmaceutical composition or vaccine as described herein, preferably via transfection or by using any of the administration modes as described herein. The method may be carried out in vitro, in vivo or ex vivo. The method may furthermore be carried out in the context of the treatment of a specific disease, particularly in the treatment of infectious diseases, preferably RSV infections as defined herein.

In this context, in vitro is defined herein as transfection or transduction of the inventive mRNA as defined herein or of the inventive composition comprising a plurality of inventive mRNA sequences as defined herein into cells in culture outside of an organism; in vivo is defined herein as transfection or transduction of the inventive mRNA or of the inventive composition comprising a plurality of inventive mRNA sequences into cells by application of the inventive mRNA or of the inventive composition to the whole organism or individual and ex vivo is defined herein as transfection or transduction of the inventive mRNA or of the inventive composition comprising a plurality of inventive mRNA sequences into cells outside of an organism or individual and subsequent application of the transfected cells to the organism or individual.

Likewise, according to another aspect, the present invention also provides the use of the inventive mRNA sequence as defined herein or of the inventive composition comprising a plurality of inventive mRNA sequences as defined herein, preferably for diagnostic or therapeutic purposes, for expression of an encoded antigenic peptide or protein, e.g. by applying or administering the inventive mRNA sequence as defined herein or of the inventive composition comprising a plurality of inventive mRNA sequences as defined herein, e.g. to a cell-free expression system, a cell (e.g. an expression host cell or a somatic cell), a tissue or an organism. The use may be applied for laboratory, for research, for diagnostic for commercial production of peptides or proteins and/or for therapeutic purposes. In this context, typically after preparing the inventive mRNA sequence as defined herein or of the inventive composition comprising a plurality of inventive mRNA sequences as defined herein, it is typically applied or administered to a cell-free expression system, a cell (e.g. an expression host cell or a somatic cell), a tissue or an organism, preferably in naked form or complexed form, or as a pharmaceutical composition or vaccine as described herein, preferably via transfection or by using any of the administration modes as described herein. The use may be carried out in vitro, in vivo or ex vivo. The use may furthermore be carried out in the context of the treatment of a specific disease, particularly in the treatment of RSV infections.

In a further aspect, the invention provides a method of treatment or prophlaxis of RSV infections comprising the steps:
a) providing the inventive mRNA sequence, the composition comprising a plurality of inventive mRNA sequences, the pharmaceutical composition or the kit or kit of parts comprising the inventive mRNA sequence as defined above;
b) applying or administering the mRNA sequence, the composition, the pharmaceutical composition or the kit or kit of parts to a tissue or an organism;
c) optionally administering RSV immune globuline.

Taken together, the invention provides in a certain aspect an mRNA sequence comprising a coding region encoding at least one antigenic peptide or protein of Respiratory syncytial virus (RSV). The inventive mRNA sequence is for use in a method of prophylactic and/or therapeutic treatment of infections caused by syncytial virus (RSV). Accordingly, the invention relates to an mRNA sequence as defined herein for use in a method of prophylactic and/or therapeutic treatment of RSV infections.

In the present invention, if not otherwise indicated, different features of alternatives and embodiments may be combined with each other, where suitable. Furthermore, the term "comprising" shall not be narrowly construed as being limited to "consisting of" only, if not specifically mentioned. Rather, in the context of the present invention, "consisting of" is an embodiment specifically contemplated by the inventors to fall under the scope of "comprising", wherever "comprising" is used herein.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

BRIEF DESCRIPTION OF THE FIGURES

The figures shown in the following are merely illustrative and shall describe the present invention in a further way. These figures shall not be construed to limit the present invention thereto.

FIG. 1: G/C optimized mRNA sequence of R1691 coding for RSV-F protein of the RSV long strain (RSV-F long) as comprised in the RSV-F long mRNA vaccine (SEQ ID NO. 31).

FIG. 2: G/C optimized mRNA sequence of R2510 coding for RSV-F protein of the RSV long strain (RSV-F long) as comprised in the RSV-F long mRNA vaccine (SEQ ID NO. 32).

FIG. 3: G/C optimized mRNA sequence of R2821 coding for RSV-F del554-574 mutant protein of the RSV long strain (RSV-F long) (SEQ ID NO. 33).

FIG. 4: G/C optimized mRNA sequence of R2831 coding for RSV-N protein of the RSV long strain (RSV-F long) (SEQ ID NO. 34).

FIG. 5: G/C optimized mRNA sequence of R2833 coding for RSV-$M_{2-1}$ protein of the RSV long strain (RSV-F long) (SEQ ID NO. 35).

FIGS. 6A-C: show that the RSV-F long mRNA vaccine induces antibody titers against the RSV-F protein comparable to those against inactivated RSV.

Female BALB/c mice were intradermally (i.d.) injected with the RSV-F long mRNA vaccine (160 μg of R1691) or Ringer-Lactate (RiLa buffer) as buffer control. One group was intramuscularly (i.m.) injected with 10 μg of the inactivated RSV long vaccine. All animals received boost injections on days 21 and 35, blood samples were collected on day 49 for the determination of antibody titers of pooled sera as described in Example 2.

As can be seen, the RSV-F long mRNA vaccine induces anti-F protein antibodies of the IgG1 and IgG2a subclasses. Antibody titers are displayed in the graph (n=5 mice/group).

Figure 7:
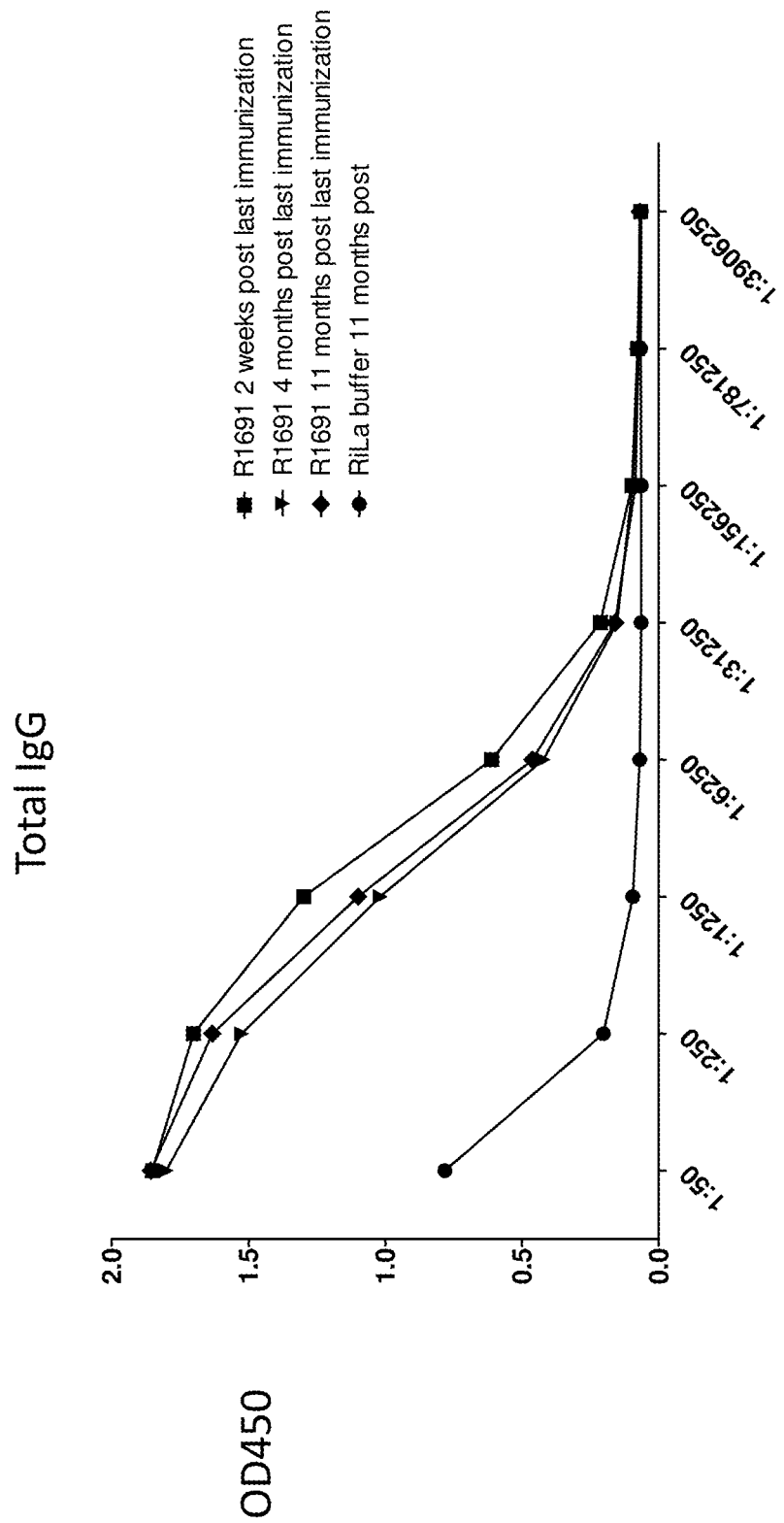

FIG. 7: shows that the RSV-F long mRNA vaccine (R1691) induces a long-lived immune response in mice.

The experiment was performed as described in Example 3 and antibody total IgG titers determined by ELISA.

As can be seen, the antibody titers are stable for at least eleven months after the last boost vaccination.

FIGS. 8A-D: show that the RSV-F long mRNA vaccine (R1691) induces RSV Fusion (F) protein-specific multifunctional CD8$^+$ T cells in mice.

The experiment was performed as described in Example 4 and T cells were analysed by intracellular cytokine staining for the antigen-specific induction of cytokines. Cells were stimulated with a RSV-F peptide (stim. F; KYKNAVTEL) or a control influenza HA peptide (stim. HA; IYSTVASSL). The line in the graph represents the median value (n=5 mice/group).

As can be seen, the RSV-F long mRNA vaccine induces RSV Fusion (F) protein-specific multifunctional CD8$^+$ T cells in contrast to the vaccine based on inactivated RSV which is not able to induce F protein-specific CD8$^+$ T cells.

Figure 9C:
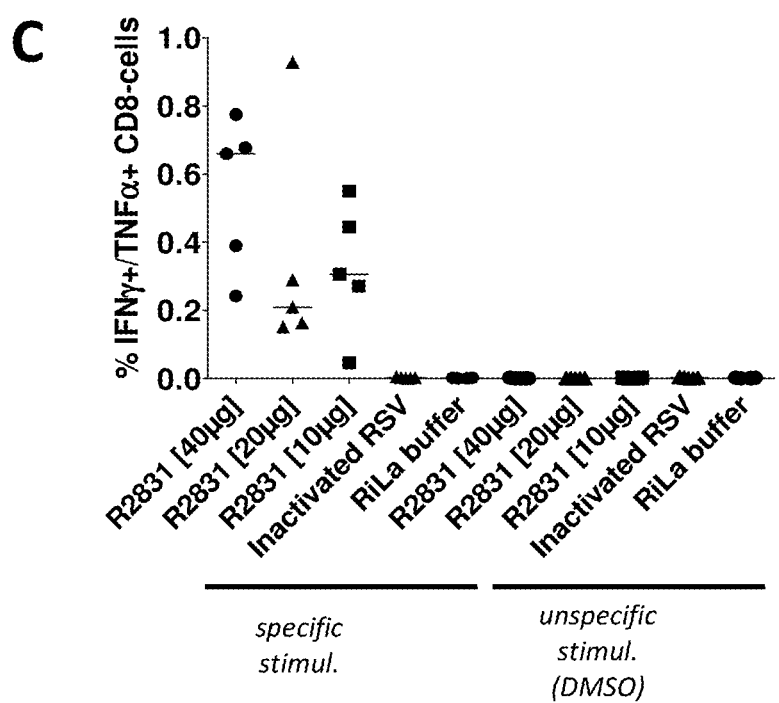

FIGS. 9A-C: show that the RSV-N mRNA vaccine (R2831) induces Nucleoprotein (N)-specific multifunctional CD8$^+$ T cells in mice.

The experiment was performed as described in Example 5 and T cells were analysed by intracellular cytokine staining for the antigen-specific induction of cytokines after stimulation with ProMix RSV-N(15mer peptides). The line in the graph represents the median value (n=5 mice/group).

As can be seen, the RSV-N mRNA vaccine induces RSV Nucleoprotein (N)-specific multifunctional CD8$^+$ T cells in contrast to the vaccine based on inactivated RSV which is not able to induce N protein-specific CD8$^+$ T cells.

Figure 10C:
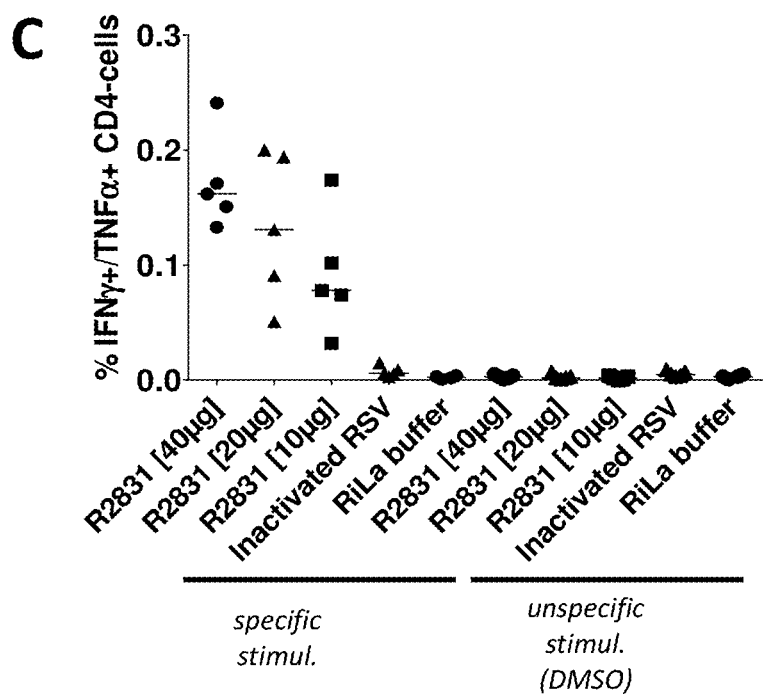

FIGS. 10A-C: show that the RSV-N mRNA vaccine (R2831) induces Nucleoprotein (N)-specific multifunctional CD4$^+$ T cells in mice.

The experiment was performed as described in Example 5 and T cells were analysed by intracellular cytokine staining for the antigen-specific induction of cytokines after stimulation with ProMix RSV-N(15mer peptides). The line in the graph represents the median value (n=5 mice/group).

As can be seen, the RSV-N mRNA vaccine induces RSV Nucleoprotein (N)-specific multifunctional CD4$^+$ T cells in contrast to the vaccine based on inactivated RSV which is not able to induce N protein-specific CD4$^+$ T cells.

Figure 11C:
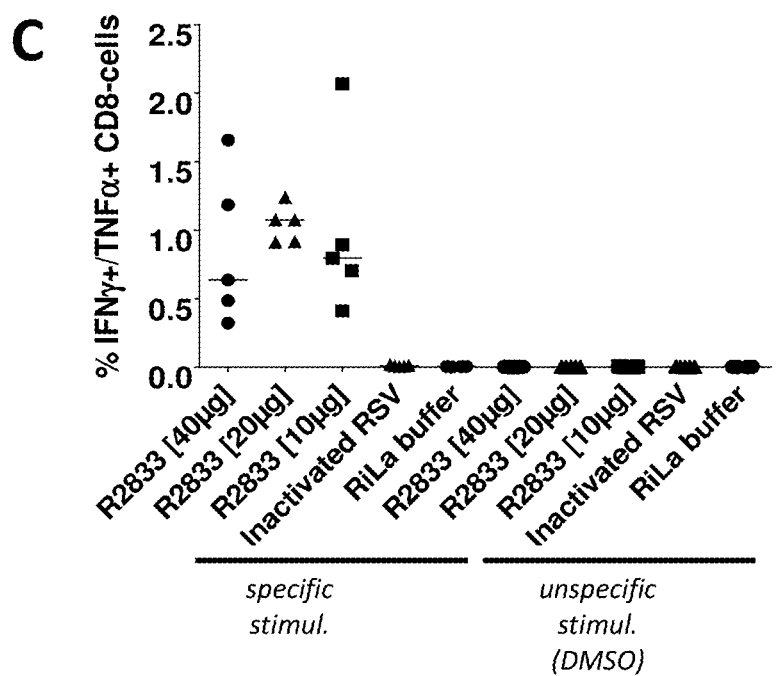

FIGS. 11A-C: show that the RSV-M2-1 mRNA vaccine (R2833) induces M2-1-specific multifunctional CD8$^+$ T cells in mice.

The experiment was performed as described in Example 5 and T cells were analysed by intracellular cytokine staining for the antigen-specific induction of cytokines after stimulation with a $M_{2-1}$ specific 9mer peptide. The line in the graph represents the median value (n=5 mice/group).

As can be seen, the RSV-$M_{2-1}$ mRNA vaccine induces RSV RSV-M2-$_1$-specific multifunctional CD8$^+$ T cells in contrast to the vaccine based on inactivated RSV which is not able to induce $M_{2-1}$ protein-specific CD8$^+$ T cells.

Figure 12:
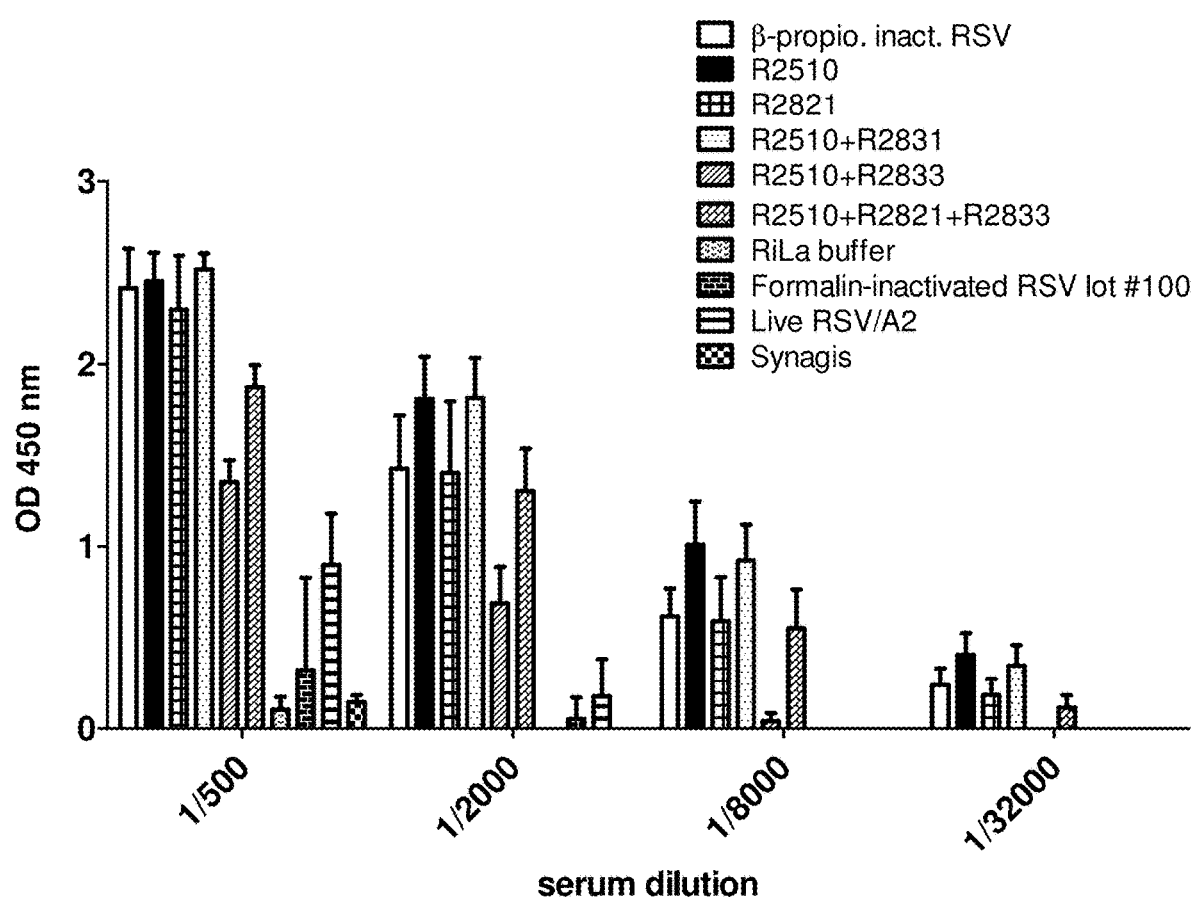

FIG. 12: shows that RSV-F mRNA vaccines either alone (RSV-F=R2510; RSV-Fdel554-574 mutant=R2821) or in combination with mRNAs encoding other RSV proteins (RSV-N=R2831; RSV-$M_{2-1}$=R2833) induce humoral immune responses in cotton rats.

The experiment was performed as described in Example 6 and RSV-F specific total IgG antibody titers were determined by ELISA on day 49. Serum was analyzed in different dilution, as given below the graph.

Figure 13:
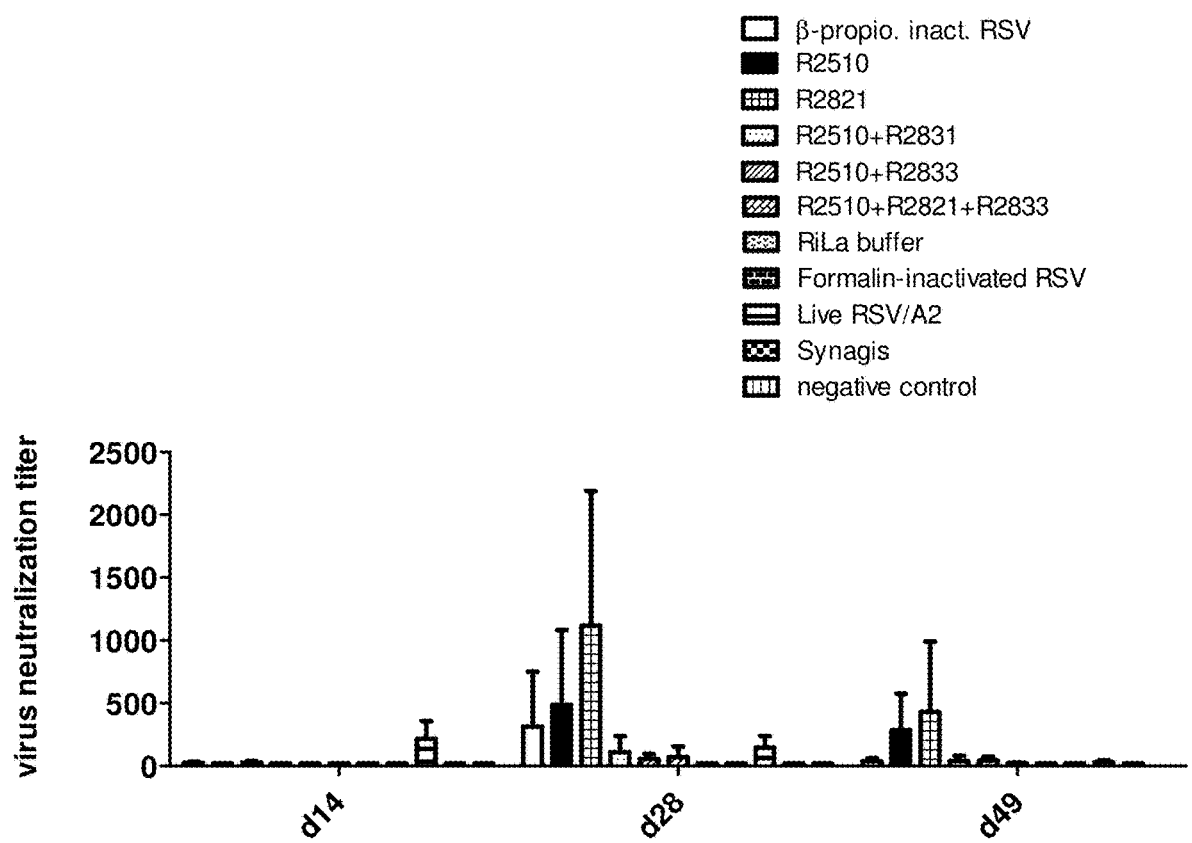

FIG. 13: shows that RSV-F mRNA vaccines either alone (RSV-F, R2510; RSV-Fdel554-574 mutant, R2821) or in combination with mRNAs encoding other RSV proteins (RSV-N=R2831; RSV-$M_{2-1}$=R2833) induce the formation of functional antibodies in cotton rats as shown by virus neutralizing antibody titers.

The experiment was performed as described in Example 6 and virus neutralizing titers on day 49 were determined by plaque reduction assay.

FIGS. 14A-B: show that RSV-F mRNA vaccines either alone (RSV-F=R2510; RSV-Fdel554-574 mutant=R2821) or in combination with mRNAs encoding other RSV proteins (RSV-N=R2831; RSV-M$_{2-1}$=R2833) reduce lung and nasal titers in cotton rats challenged with RSV virus.

The experiment was performed as described in Example 6.

(A) Lung titers on day 5 after RSV challenge infection. All animal groups vaccinated with mRNA vaccines showed virus titers below the level of detection of the performed virus titration demonstrating protection of vaccinated cotton rats in terms of viral lung titers. In comparison to the mRNA vaccines the vaccine based on formalin-inactivated virus were not able to prevent virus titers in the lung.

(B) Nasal titers on day 5 after RSV challenge infection. The viral titer in the nasal tissue was also strongly reduced in groups vaccinated with mRNA. In comparison to the mRNA vaccines the vaccine based on formalin-inactivated virus were not able to reduce the nasal virus titers.

Figure 15:
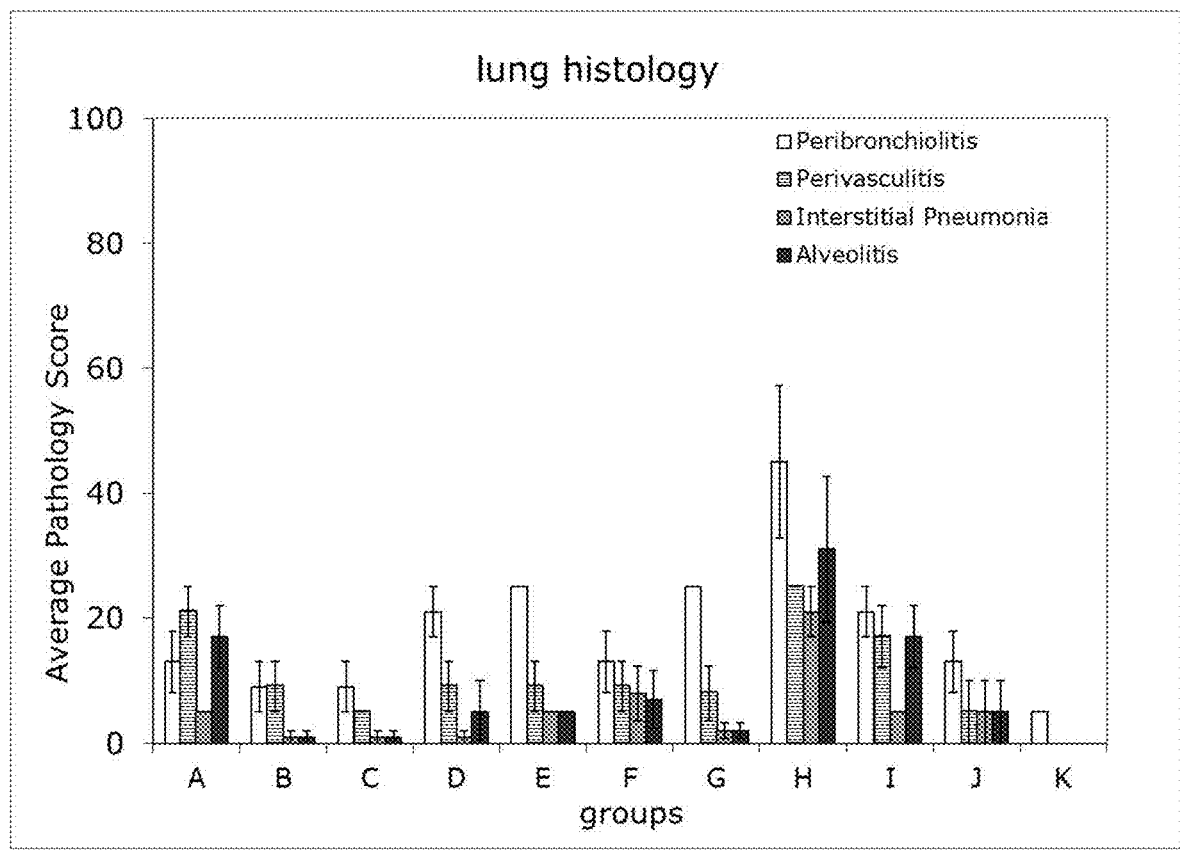

FIG. 15: shows the results of the lung histopathology analysis from the RSV cotton rat challenge study described in Example 6.

FIGS. 16A-D: show the results of the quantitative reverse transcription polymerase chain reaction (RT-PCR) of viral genome copy numbers (by measuring copy numbers of the RSV NS-1 gene) or expressed cytokines from lung tissue of the RSV infected animals (or controls) of the RSV cotton rat challenge study described in Example 6.

FIGS. 17A-B: show that RSV-F mRNA vaccines (RSV-F=R2510; RSV F* (RSV-Fdel554-574 mutant)=R2821) reduce lung titers in cotton rats challenged with RSV virus.

The experiment was performed as described in Example 7.

(A) Lung titers on day 5 after RSV challenge infection. All animal groups vaccinated intradermally with mRNA vaccines showed reduced virus titers compared to the buffer control group demonstrating protection of vaccinated cotton rats in terms of viral lung titers. Already one single dose of RSV-F mRNA vaccines efficiently reduced viral titers in the lung.

(B) Lung titers on day 5 after RSV challenge infection. The viral titer in the lung was also strongly reduced in groups intramuscularly vaccinated with mRNA.

EXAMPLES

The examples shown in the following are merely illustrative and shall describe the present invention in a further way. These examples shall not be construed to limit the present invention thereto.

Example 1: Preparation of the mRNA Vaccine

1. Preparation of DNA and mRNA Constructs

For the present examples DNA sequences, encoding the RSV-F protein (R1691 and R2510), the RSV-F del554-574 (R2821) mutant protein, the RSV N-protein (R2831) and the RSV M2-1 protein (R2833) of the RSV long strain were prepared and used for subsequent in vitro transcription reactions. The RSV-Fdel554-574 mutant protein has been described previously (Oomens et al. 2006. J. Virol. 80(21): 10465-77).

According to a first preparation, the DNA sequences coding for the above mentioned mRNAs were prepared. The construct R1691 was prepared by modifying the wild type coding sequence by introducing a GC-optimized sequence for stabilization, followed by a stabilizing sequence derived from the alpha-globin-3'-UTR (muag (mutated alpha-globin-3'-UTR) according to SEQ ID No. 29), a stretch of 64 adenosines (poly(A)-sequence), a stretch of 30 cytosines (poly(C)-sequence), and a histone stem loop according to SEQ ID No. 30. In SEQ ID NO: 31 (see FIG. 1) the sequence of the corresponding mRNA is shown. The constructs R2510, R2821, R2831 and R2833 were prepared by introducing a 5'-TOP-UTR derived from the ribosomal protein 32L according to SEQ ID No. 23, modifying the wild type coding sequence by introducing a GC-optimized sequence for stabilization, followed by a stabilizing sequence derived from the albumin-3'-UTR (albumin7 according to SEQ ID No. 25), a stretch of 64 adenosines (poly(A)-sequence), a stretch of 30 cytosines (poly(C)-sequence), and a histone stem loop according to SEQ ID No. 30. In SEQ ID NOs: 32-35 (see FIG. 2-5) the sequences of the corresponding mRNAs are shown.

TABLE 1

| mRNA constructs | | | |
|---|---|---|---|
| RNA | Antigen | FIG. | SEQ ID NO. |
| R1691 | RSV F | 1 | SEQ ID NO. 31 |
| R2510 | RSV F | 2 | SEQ ID NO. 32 |
| R2821 | RSV Fdel554-574 | 3 | SEQ ID NO. 33 |
| R2831 | RSV N | 4 | SEQ ID NO. 34 |
| R2833 | RSV M$_{2-1}$ | 5 | SEQ ID NO. 35 |

2. In Vitro Transcription

The respective DNA plasmids prepared according to paragraph 1 were transcribed in vitro using T7 polymerase in the presence of a CAP analog (m$^7$GpppG). Subsequently the mRNA was purified using PureMessenger® (CureVac, Tubingen, Germany; WO2008/077592A1).

3. Reagents

Complexation Reagent: protamine

4. Preparation of the Vaccine

The mRNA was complexed with protamine by addition of protamine to the mRNA in the ratio (1:2) (w/w) (adjuvant component). After incubation for 10 minutes, the same amount of free mRNA used as antigen-providing RNA was added.

For example: RSV-F long vaccine (R1691): comprising an adjuvant component consisting of mRNA coding for RSV F protein long (R1691) according to SEQ ID NO. 31 complexed with protamine in a ratio of 2:1 (w/w) and the antigen-providing free mRNA coding for RSV F protein long (R1691) according to SEQ ID NO. 31 (ratio 1:1; complexed RNA:free RNA).

Example 2: Induction of a Humoral Immune Response by the RSV-F Long mRNA Vaccine in Mice Immunization On day zero, BALB/c mice were intradermally (i.d.) injected with the RSV-F long mRNA vaccine (R1691 according to Example 1; 25 µg/mouse/vaccination day) or Ringer-lactate (RiLa) as buffer control as shown in Table 2. A control group was intramuscularly (i.m.) injected with 10 µg of the inactivated RSV long vaccine. The inactivated "Respiratory Syncytial Virus Antigen" (inactivated RSV long) was purchased from the INSTITUT VIRION/SERION GmbH-SERION IMMUNDIAGNOSTICA GmbH. The inactivated virus was diluted in sterile PBS, so that a final concentration of 0.2 µg/µL was achieved. All animals received boost injections on day 14 and day 28. Blood samples were collected on day 42 for the determination of anti-RSV F antibody titers.

TABLE 2

Animal groups

| Group | Strain sex | No. mice | Route volume | Vaccine dose | Vaccination schedule |
|---|---|---|---|---|---|
| 1 | BALB/c Female | 5 | i.d. 2 × 50 µl | R1691 2 µg | d0: prime, d14: boost, d28: boost, d42: blood collection |
| 2 | BALB/c Female | 5 | i.m. 2 × 25 µl | Inactivated RSV long 10 µg | d0: prime, d14: boost, d28: boost, d42: blood collection |
| 3 | BALB/c Female | 5 | i.d. 2 × 50 µl | 80% Ringer Lactate (RiLa) buffer | d0: prime, d14: boost, d28: boost, d42: blood collection |

Determination of Anti-RSV F Protein Antibodies by ELISA

ELISA plates are coated with recombinant human RSV fusion glycoprotein (rec.hu F-protein, final conc.: 5 µg/mL) (Sino Biological Inc.). Coated plates are incubated using given serum dilutions and binding of specific antibodies to the F protein is detected using biotinylated isotype specific anti-mouse antibodies in combination with streptavidin-HRP (horse radish peroxidase) with ABTS substrate.

Results

Figure 6C:
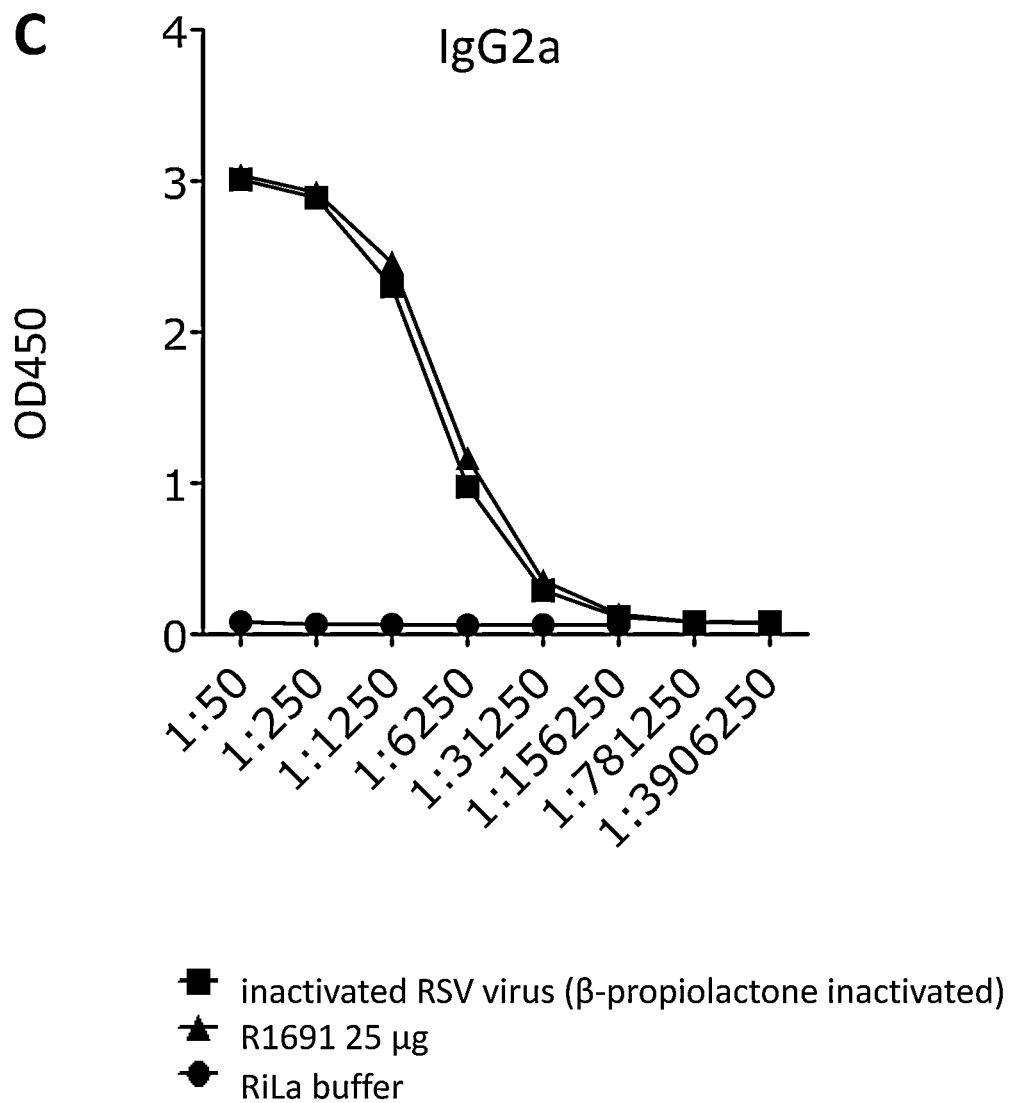

As can be seen in FIG. 6, the RSV-F long mRNA vaccine induces antibody titers (total IgG, IgG1 and IgG2a) against the RSV F protein comparable to those against inactivated RSV.

Example 3: Induction of a Long-Lived Humoral Immune Response by the RSV-F Long mRNA Vaccine in Mice Immunization BALB/c mice were intradermally (i.d.) injected with 20 µg of the RSV-F long mRNA vaccine (R1691) or Ringer Lactate (RiLa) buffer according to the vaccination schedule shown in Table 3. Blood was collected 2 weeks, 4 months and 11 months after the last immunization.

TABLE 3

Animal groups

| Group | Strain sex | Number of mice | Route volume | Vaccine dose | Vaccination schedule (day) |
|---|---|---|---|---|---|
| 1 | BALB/c Female | 5 | i.d. 100 µl | R1691 20 µg | d0, d14, d28 |
| 4 | BALB/c Female | 5 | i.d. 100 µl | 80% RiLa buffer | d0, d14, d28 |

Results

As can be seen in FIG. 7, the RSV-F long mRNA vaccine induced a long-lived immune response as demonstrated by stable antibody titers for at least 11 months after the last boost vaccination.

Example 4: Induction of a Cellular Immune Response by the RSV-F Long mRNA Vaccine in Mice Immunization On day zero, BALB/c mice were intradermally (i.d.) injected with the RSV-F long mRNA vaccine R1691 (20 µg/mouse/vaccination day) or Ringer-lactate (RiLa) as buffer control as shown in Table 4. A control group was intramuscularly (i.m.) injected with 10 µg of the inactivated RSV long vaccine. The inactivated "Respiratory Syncytial Virus Antigen" (inactivated RSV long) was purchased from the INSTITUT VIRION/SERION GmbH-SERION IMMUNDIAGNOSTICA GmbH. The inactivated virus was diluted in sterile PBS, so that a final concentration of 0.2 µg/µL was achieved.

All animals received boost injections on days 14 and 28. Spleens were collected on day 34 for the analysis of antigen-specific T cells.

TABLE 4

Animal groups

| Group | Strain sex | Number of mice | Route volume | Vaccine dose | Vaccination schedule |
|---|---|---|---|---|---|
| 1 | BALB/c Female | 5 | i.d. 2 × 50 µl | R1691 20 µg | d0: prime, d14: boost, d28: boost, d34: spleen collection |
| 2 | BALB/c Female | 5 | i.m. 2 × 25 µl | Inactivated RSV long 10 µg | d0: prime, d14: boost, d28: boost, d34: spleen collection |
| 3 | BALB/c Female | 5 | i.d. 2 × 50 µl | Ringer Lactate (RiLa) buffer | d0: prime, d14: boost, d28: boost, d34: spleen collection |

Intracellular Cytokine Staining

Splenocytes from vaccinated and control mice were isolated according to a standard protocol. Briefly, isolated spleens were grinded through a cell strainer and washed in PBS/1% FBS followed by red blood cell lysis. After an extensive washing step with PBS/1% FBS splenocytes were seeded into 96-well plates ($2\times10^6$ cells/well). The next day cells were stimulated with a RSV-F peptide (KYKNAVTEL; 5 µg/ml; H-2kd-restructed T-cell epitope) or an irrelevant control peptide derived from the influenza HA protein (IYSTVASSL; 5 µg/ml; purchased from EMC Microcollections) and 2.5 µg/ml of an anti-CD28 antibody (BD Biosciences) for 6 hours at 37° C. in the presence of the mixture of GolgiPlug™/GolgiStop™ (Protein transport inhibitors containing Brefeldin A and Monensin, respectively; BD Biosciences). After stimulation cells were washed and stained for intracellular cytokines using the Cytofix/Cytoperm reagent (BD Biosciences) according to the manufacturer's instructions. The following antibodies were used for staining: CD8-PECy7 (1:200), CD3-FITC (1:200), IL2-PerCP-Cy5.5 (1:100), TNFα-PE (1:100), IFNγ-APC (1:100) (eBioscience), CD4-BD Horizon V450 (1:200) (BD Biosciences) and incubated with Fcγ-block diluted 1:100. Aqua Dye was used to distinguish live/dead cells (Invitrogen). Cells were collected using a Canto II flow cytometer (Beckton Dickinson). Flow cytometry data were analysed using FlowJo software (Tree Star, Inc.). Statistical analysis was performed using GraphPad Prism software, Version 5.01. Statistical differences between groups were assessed by the Mann Whitney test.

Results

As can be seen from FIG. 8, the RSV-F long mRNA vaccine (R1691) induced IFNγ positive, TNFα positive and IFNγ/TNFα double-positive multifunctional $CD8^+$ T cells directed against RSV F protein. Surprisingly the vaccine based on inactivated RSV virus was not able to induce antigen-specific $CD8^+$ T cells.

Example 5: Induction of Cellular Immune Responses by the RSV-N and RSV-M2-1 mRNA Vaccines in Mice Immunization On day zero, BALB/c mice were intradermally (i.d.) injected with different doses of the RSV-N mRNA vaccine R2831, the RSV-$M_{2-1}$ mRNA vaccine R2833 or Ringer-lactate (RiLa) as buffer control as shown in Table 5. A control group was intramuscularly (i.m.) injected with 10 µg of the inactivated RSV long vaccine. The inactivated "Respiratory Syncytial Virus Antigen" (inactivated RSV long) was purchased from the INSTITUT VIRION/SERION GmbH-SERION IMMUNDIAGNOSTICA GmbH. The inactivated virus was diluted in sterile PBS, so that a final concentration of 0.2 µg/µL was achieved. All animals received boost injections on days 7 and 21. Spleens were collected on day 27 for the analysis of antigen-specific T cells.

Intracellular cytokine staining was performed as described in Example 4 except that cells were treated with the following stimulators at:

M2-1 peptide (5 ag/ml) group 4 to 8; (SYIGSINNI from ProImmune); ProMix N (1 µg/ml) 1-3, group 7 and 8; (PX39 from Proimmune); control: medium+DMSO+anti-CD28, group 1-8 as descripted above.

Results

As can be seen from FIG. 9, the RSV-N mRNA vaccine (R2831) induced IFNγ positive, TNFα positive and IFNγ/TNFα double-positive multifunctional $CD8^+$ T cells directed against RSV N protein in mice.

Surprisingly the vaccine based on inactivated RSV virus was not able to induce antigen-specific $CD8^+$ T cells.

As can be seen from FIG. 10, the RSV-N mRNA vaccine (R2831) induced IFNγ positive, TNFα positive and IFNγ/TNFα double-positive multifunctional $CD4^+$ T cells directed against RSV N protein in mice.

Surprisingly the vaccine based on inactivated RSV virus was not able to induce antigen-specific $CD4^+$ T cells.

As can be seen from FIG. 11, the RSV-$M_{2-1}$ mRNA vaccine (R2833) induced IFNγ positive, TNFα positive and IFNγ/TNFα double-positive multifunctional $CD8^+$ T cells directed against RSV $M_{2-1}$ protein in mice.

Surprisingly the vaccine based on inactivated RSV virus was not able to induce antigen-specific $CD8^+$ T cells.

Example 6: RSV Cotton Rat Challenge Study I

For the development of RSV vaccines the cotton rat is an accepted animal model, especially for the challenge infection. Cotton rats respond to formalin-inactivated RSV virus vaccine preparations with enhanced lung pathology. This allows the evaluation of the safety of a vaccination in terms of enhanced disease phenomenon.

To broaden and optimize the RSV-specific immune response, mRNA vaccines encoding different RSV proteins (RSV F, mutant RSV-Fdel554-574, N and $M_2$-1) were prepared according to Example 1. In order to assess the effect of single or combined vaccines, these vaccines were administered either alone or in combination (cocktail vaccine) as shown in Table 5. Vaccine volumes of 2×50 µl were

TABLE 5

Animal groups

| Group | Strain sex | No. mice | Route volume | Vaccine dose | Vaccination schedule |
|---|---|---|---|---|---|
| 1 | BALB/c Female | 5 | i.d. 1 × 50 µl | R2831 RSV-N 40 µg | d0: prime, d7: boost, d21: boost, d27: spleen collection |
| 2 | BALB/c Female | 5 | i.d. 1 × 25 µl | R2831 RSV-N 20 µg | d0: prime, d7: boost, d21: boost, d27: spleen collection |
| 3 | BALB/c Female | 5 | i.d. 1 × 12.5 µl | R2831 RSV-N 10 µg | d0: prime, d7: boost, d21: boost, d27: spleen collection |
| 4 | BALB/c Female | 5 | i.d. 1 × 50 µl | R2833 RSV-$M_{2-1}$ 40 µg | d0: prime, d7: boost, d21: boost, d27: spleen collection |
| 5 | BALB/c Female | 5 | i.d. 1 × 25 µl | R2833 RSV-$M_{2-1}$ 20 µg | d0: prime, d7: boost, d21: boost, d27: spleen collection |
| 6 | BALB/c Female | 5 | i.d. 1 × 12.5 µl | R2833 RSV-$M_{2-1}$ 10 µg | d0: prime, d7: boost, d21: boost, d27: spleen collection |
| 7 | BALB/c Female | 5 | i.m. 2 × 25 µl | Inactiv. RSV long 10 µg | d0: prime, d7: boost, d21: boost, d27: spleen collection |
| 8 | BALB/c Female | 5 | i.d. 1 × 50 µl | 100% RiLa buffer | d0: prime, d7: boost, d21: boost, d27: spleen collection | injected intradermally (i.d.) into the back skin of cotton rats. Additional groups were immunized intramuscularly (i.m.) with β-propiolactone inactivated RSV (INSTITUT VIRION/SERION GmbH-SERION IMMUNDIAGNOSTICA GmbH), formalin-inactivated RSV (Sigmovir) or live RSV/A2 (Sigmovir) ($10^5$ plaque forming units, pfu) to compare their immunogenicity to mRNA vaccines. Another group received i.m. injections of the monoclonal anti-RSV antibody SYNAGIS® (Palivizumab) as passive immunization. SYNAGIS® was administered with a dose of 15 mg/kg on the day prior to RSV challenge infection. Therefore the animals were weighed and the appropriate amount of SYNAGIS® was calculated according to the animals' weight. The maximal volume for i.m. injection was 200 μl per 100 g rat. After immunization the cotton rats were challenged by intranasal (i.n.) infection with RSV/A2 virus ($10^5$ PFU in 100 μl; Sigmovir).

confluent HEp-2 monolayers in 24 well plates. After one hour incubation at 37° C. in a 5% $CO_2$ incubator, the wells were overlayed with 0.75% Methylcellulose medium. After 4 days of incubation, the overlay was removed and the cells were fixed with 0.1% crystal violet stain for one hour and then rinsed and air dried. The corresponding reciprocal neutralizing antibody titers were determined at the 60% reduction end-point of the virus control.

RSV Viral Titrations and Pulmonary Histopathology

On day 54 nasal tissue was harvested and homogenized for viral titrations. The lung was harvested en bloc and tri-sected for viral titration (left section), histopathology (right section), and PCR analysis (lingular lobe). In addition, RSV viral genome copy numbers (by measuring copy numbers of the RSV NS-1 gene) and cytokine mRNA levels were determined by quantitative reverse transcription polymerase chain reaction (qRT-PCR).

TABLE 5

Animal groups

| Groups | Vaccine dose | Volume | Antigen | Route | # of administrations | N per group | Vaccination (day) | Bleed (day) |
|---|---|---|---|---|---|---|---|---|
| A | β-propiolactone inactivated RSV 20 μg | 100 μl | — | IM | 3 | 5 | 0, 14, 28 | 14, 28, 49 |
| B | R2510 80 μg | 2 × 50 μl | RSV F | ID | 3 | 5 | 0, 14, 28 | 14, 28, 49 |
| C | R2821 80 μg | 2 × 50 μl | RSV F mutant | ID | 3 | 5 | 0, 14, 28 | 14, 28, 49 |
| D | R2510 + R2831 "cocktail I" each 40 μg | 2 × 50 μl | RSV F + RSVN | ID | 3 | 5 | 0, 14, 28 | 14, 28, 49 |
| E | R2510 + R2833 "cocktail II" each 40 μg | 2 × 50 μl | RSV F + RSV $M_{2-1}$ | ID | 3 | 5 | 0, 14, 28 | 14, 28, 49 |
| F | R2510 + R2831 + R2833 "cocktail III" each 26.666 μg | 2 × 50 μl | RSV F + RSV $M_{2-1}$ + RSVN | ID | 3 | 5 | 0, 14, 28 | 14, 28, 49 |
| G | RiLa | 2 × 50 μl | — | ID | 3 | 5 | 0, 14, 28 | 14, 28, 49 |
| H | FI-RSV Lot#100 (diluted 1:100 in PBS) | 100 μl | — | IM | 2 | 5 | 0, 28 | 28, 49 |
| I | Live RSV/A2 $10^5$ pfu | 100 μl | — | IM | 1 | 5 | 0 | 49 |
| J | SYNAGIS ® (15 mg/kg) | | — | IM | 1 | 5 | 48 | 49 |
| K | Neg. control | | — | N/A | N/A | 5 | — | — |

The following assays were performed to analyze the immune responses: RSV F-protein serum IgG ELISA, RSV virus neutralizing antibody titers (VNT), RSV viral titrations and pulmonary histopathology.

RSV F-Protein Serum IgG ELISA

The induction of anti-RSV F protein antibodies were determined by ELISA according to Example 2.

RSV Virus Neutralizing Antibody Titers (VNT)

Sera were analysed by the virus neutralization test (VNT). Briefly, sera samples were diluted 1:10 with EMEM, heat inactivated and serially diluted further 1:4. Diluted sera samples were incubated with RSV (25-50 PFU) for 1 hour at room temperature and inoculated in duplicates onto Results As can be seen from FIG. 12, the RSV-F mRNA vaccines either alone (RSV-F=R2510; RSV-Fdel554-574 mutant=R2821) or in combination with mRNAs encoding other RSV proteins (RSV-N=R2831; RSV-M2-1=R2833), induce RSV F specific humoral immune responses in cotton rats as shown by total IgG antibody titers on day 49.

As can be seen from FIG. 13, the RSV-F mRNA vaccines either alone (RSV-F=R2510; RSV-Fdel554-574 mutant=R2821) or in combination with mRNAs encoding other RSV proteins (RSV-N, R2831=RSV-M2-1=R2833), induce the formation of RSV specific functional antibodies in cotton rats as shown by virus neutralizing antibody titers.

Figure 14:
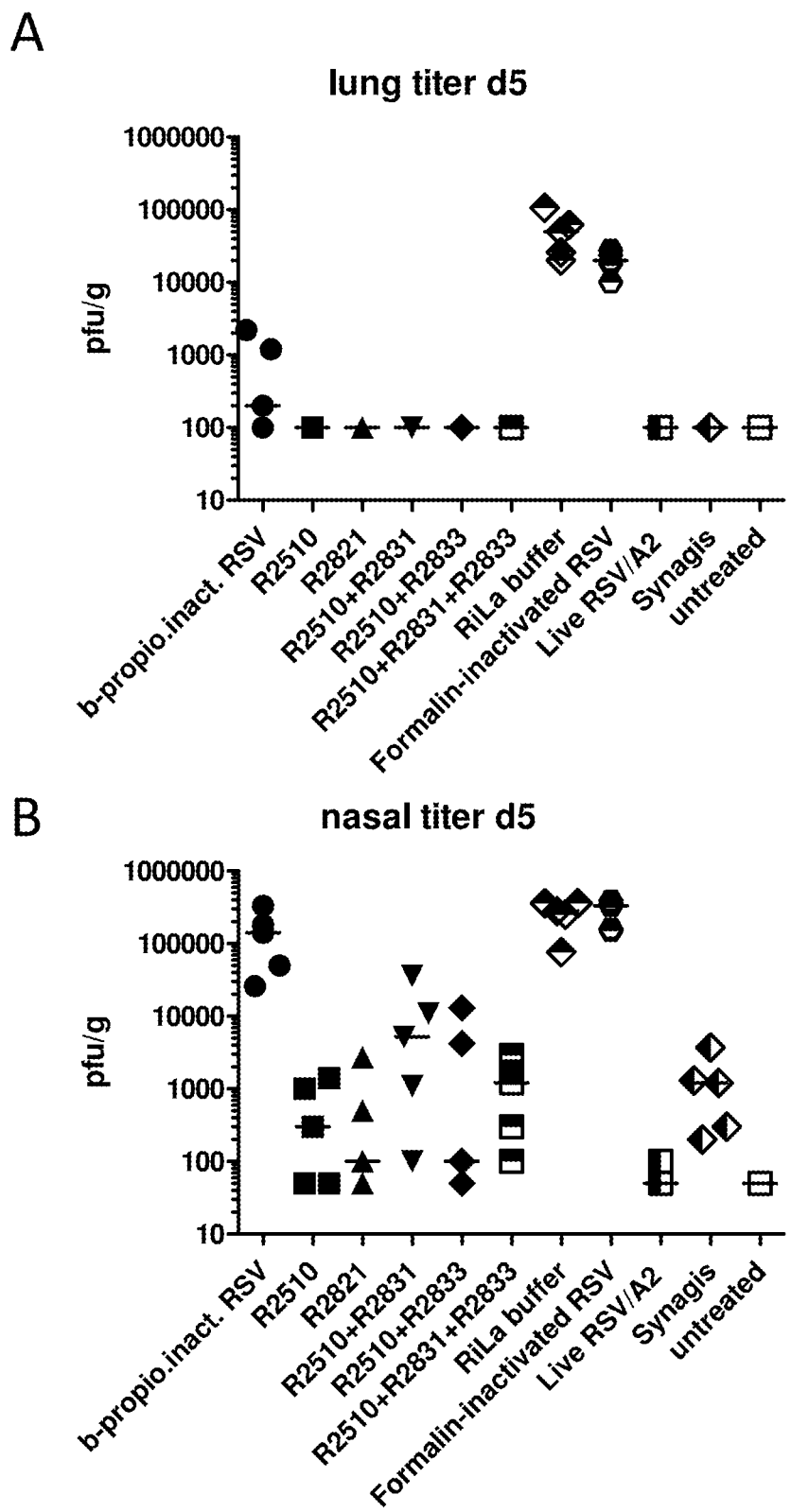

As can be seen from FIG. 14, the RSV-F mRNA vaccines either alone (RSV-F=R2510; RSV-Fdel554-574 mutant=R2821) or in combination with mRNAs encoding other RSV proteins (RSV-N=R2831; RSV-M2-1=R2833), reduce lung and nasal viral titers in cotton rats challenged with RSV virus.

As can be seen in FIG. 14A, all animal groups vaccinated with mRNA vaccines showed virus titers below the level of detection of the performed virus titration demonstrating protection of vaccinated cotton rats in terms of viral lung titers. By contrast, the Formalin-inactivated virus vaccine reduced only minimally the lung virus titer compared to the RiLa buffer control group. The effect of the β-propiolactone inactivated RSV vaccine was more pronounced but did not reduce the virus lung titer below the detection level in all animals of this group. As can be seen in FIG. 14B, the viral titer in the nasal tissue was also strongly reduced in groups vaccinated with mRNA. Nasal viral titers of the Formalin-inactivated virus were comparable to the viral titer in the RiLa vaccinated group. The β-propiolactone inactivated virus vaccine was more effective (at least for two of five animals). In contrast thereto, all mRNA vaccinated groups had reduced nasal virus titer compared to RiLa vaccinated group.

As can be seen from FIG. 15, the lung histopathology analysis from the RSV cotton rat challenge study reveals different pathology scores for the various animal groups. From the histopathology it can be concluded that none of the mRNA vaccinated groups displayed enhanced lung pathology as it is the case for the group that was vaccinated using the Formalin-inactivated RSV vaccine. The average pathology scores for peribronchiolitis (PB), perivasculitis (PV), insterstitial pneumonia (IP) and alveolitis (A) are much lower for all groups vaccinated with mRNA compared to group H (Formalin-inactivated RSV). In addition the groups being vaccinated with R2510 (group B; RSV F) or R2821 (group C; RSV F mutant) seem to exhibit reduced lung pathology compared to the RiLa buffer vaccinated and subsequently RSV infected group (G).

As can be seen in FIG. 16, the quantitative RT-PCR reveals different expression patterns for the various animal groups. The quantification of RSV genome copies by measuring the RSV NS-1 gene is displayed in A. Genome copy numbers are reduced by vaccination using mRNA vaccines compared to the RiLa buffer control (group G). This is not the case for the group that was vaccinated using formalin-inactivated-RSV (group H). As it is shown in B, the vaccination using the formalin-inactivated-RSV vaccine (group H) induces enhanced expression of the TH2 cytokine IL-4 compared to the control group that was vaccinated with RiLa buffer (group G). By contrast, the vaccination with mRNA R2821 encoding the RSV-F mutant significantly reduced IL-4 mRNA expression compared to the RiLa control group in the lung after RSV challenge infection. C. Expression of INF-γ mRNA. D. Expression of IL-5 mRNA. The expression of IL-5 is significant reduced in groups vaccinated using R2510 or R2821 compared to RiLa buffer vaccinated animals. The expression of the viral NS-1 RNA or cytokine mRNAs, which were isolated from lung tissue, is measured on day 5 post-challenge. The statistical analysis was performed with the student T-test (* p<0.05 when compared to group G (RiLa control)).

Example 7: RSV Cotton Rat Challenge Study II mRNA vaccines encoding RSV F protein (F) or mutant RSV-F protein (F*) (RSV F de1554-574) were prepared according to Example 1. In order to assess the effect of single or several vaccinations (prime and boost vaccinations), these vaccines were administered once, twice or 3 times (as shown in Table 6). Vaccine volumes of 2×50 µl were injected intradermally (i.d.) into the back skin of cotton rats. Additional groups were immunized intramuscularly (i.m.) with vaccine volumes of 1×100 µl into the right hind leg. As a control, one group was injected intradermally with Ringer-Lactate buffer (buffer). After immunization, the cotton rats were challenged by intranasal (i.n.) infection with RSV/A2 virus ($10^5$ PFU in 100 µl; Sigmovir). As a control, one group was not treated and remained unchallenged with virus (untreated).

TABLE 5

Animal groups

| Groups | Vaccine dose | Volume | Antigen | Route | # of administrations | N per group | Vaccination (day) | Challenge (day) |
|---|---|---|---|---|---|---|---|---|
| F* i.d. 3x | R2821 80 µg | 2 × 50 µl | RSV F mutant | ID | 3 | 5 | 0, 14, 28 | 49 |
| F* i.d. 2x | R2821 80 µg | 2 × 50 µl | RSV F mutant | ID | 2 | 5 | 0, 14 | 49 |
| F* i.d. 1x | R2821 80 µg | 2 × 50 µl | RSV F mutant | ID | 1 | 5 | 0 | 49 |
| F i.d. 3x | R2510 80 µg | 2 × 50 µl | RSV F | ID | 3 | 5 | 0, 14, 28 | 49 |
| F i.d. 2x | R2510 80 µg | 2 × 50 µl | RSV F | ID | 2 | 5 | 0, 14 | 49 |
| F i.d. 1x | R2510 80 µg | 2 × 50 µl | RSV F | ID | 1 | 5 | 0 | 49 |
| F* i.m. | R2821 80 µg | 1 × 100 µl | RSV F mutant | IM | 2 | 5 | 0, 14 | 49 |
| F i.m. | R2510 80 µg | 1 × 100 µl | RSV F | IM | 2 | 5 | 0, 14 | 49 |
| Buffer | — | 2 × 50 µl | | ID | 3 | 5 | 0, 14, 28 | 49 |
| untreated | — | | — | N/A | N/A | 5 | — | — |

RSV Viral Titrations

The determination of RSV viral titers was conducted as described in Example 6.

Results

As shown in FIG. 17A, already one single intradermal vaccination with mRNA vaccines coding for RSV F protein (F) or mutant RSV-F protein (F*) (RSV F del554-574) was highly efficient in reducing the viral titer in the lung compared to the buffer control group. A second and third vaccination ("boost vaccinations) reduced the viral titers below detection level.

As shown in FIG. 17B, already two intramuscular vaccinations with mRNA vaccines coding for RSV F protein (F) or mutant RSV-F protein (F*) (RSV F del554-574) strongly reduced the viral titer in the lung compared to the buffer control group.

```

The invention claimed is:

1. A pharmaceutical composition comprising a mRNA molecule having a coding sequence encoding a Respiratory Syncytial Virus fusion protein (RSV-F) with a deleted C-terminus (F-del) lacking amino acids 554-574 of native RSV-F, said coding sequence comprising a nucleic acid sequence at least 80% identical to the protein coding portion of the sequence of SEQ ID NO: 33, wherein the mRNA comprises from 5' to 3': (i) a 5'-cap structure, (ii) a 5' untranslated region (UTR); (iii) the coding sequence encoding the F protein; (iv) a 3' UTR and (v) a poly(A) sequence, wherein the mRNA molecule is formulated with a cationic lipid.

2. The pharmaceutical composition of claim 1, wherein the 5' structure is m7GpppN.

3. The pharmaceutical composition of claim 1, wherein the 5' cap structure is a Cap1 structure.

4. The pharmaceutical composition of claim 1, wherein the poly(A) sequence comprises a sequence of 25 to 400 adenosine nucleotides.

5. The pharmaceutical composition of claim 4, wherein the poly(A) sequence comprises 60 to 250 adenosine nucleotides.

6. The pharmaceutical composition of claim 5, wherein the poly(A) sequence is at the 3' end of the mRNA molecule.

7. The pharmaceutical composition of claim 1, wherein the 3' UTR comprises a stabilizing sequence from the alpha globin 3' UTR.

8. The pharmaceutical composition of claim 1, wherein the composition comprises at least a second, different, mRNA encoding an antigen from a different virus or an antigenic fragment thereof.

9. The pharmaceutical composition of claim 1, wherein the pharmaceutical composition is formulated for intramuscular injection.

10. The pharmaceutical composition of claim 1, wherein the encoded RSV-F comprises the transmembrane domain of native RSV-F.

11. The pharmaceutical composition of claim 10, wherein the poly(A) sequence comprises 60 to 250 adenosine nucleotides.

12. The pharmaceutical composition of claim 11, wherein the 5' cap structure is a Cap1 structure.

13. A method of stimulating an immune response to Respiratory Syncytial Virus (RSV) in a subject comprising administering to the subject a pharmaceutical composition comprising a mRNA molecule having a coding sequence encoding a RSV fusion protein (RSV-F) with a deleted C-terminus (F-del) lacking amino acids 554-574 of native RSV-F, said coding sequence comprising a nucleic acid sequence at least 80% identical to the protein coding portion of the sequence of SEQ ID NO: 33, wherein the mRNA comprises from 5' to 3': (i) a 5'-cap structure, (ii) a 5' untranslated region (UTR); (iii) the coding sequence encoding the F protein; (iv) a 3' UTR and (v) a poly(A) sequence of 60 to 250 adenosine nucleotides, wherein the mRNA molecule is formulated with a cationic lipid.

14. The method of claim 13, wherein the pharmaceutical composition is administered by intramuscular injection.

15. The method of claim 14, wherein the 5' cap structure is m7GpppN.

16. The method of claim 14, wherein the 5' structure is a Cap1 structure.

17. The method of claim 14, wherein the poly(A) sequence is at the 3' end of the mRNA molecule.

18. The method of claim 14, wherein the 3' UTR comprises a stabilizing sequence from the alpha globin 3' UTR.

19. The method of claim 14, wherein the composition comprises at least a second, different, mRNA encoding an antigen from a different virus or an antigenic fragment thereof.

20. The method of claim 14, wherein the encoded RSV-F comprises the transmembrane domain of native RSV-F.

21. A method of stimulating an immune response to Respiratory Syncytial Virus (RSV) in a subject comprising administering to the subject a pharmaceutical composition comprising a mRNA molecule having a coding sequence encoding a RSV fusion protein (RSV-F) with a deleted C-terminus (F-del) lacking amino acids 554-574 of native RSV-F, said coding sequence comprising a nucleic acid sequence at least 80% identical to the protein coding portion of the sequence of SEQ ID NO: 33, wherein the mRNA comprises from 5' to 3': (i) a 5' cap structure, (ii) a 5' untranslated region (UTR); (iii) the coding sequence encoding the F protein; (iv) a 3' UTR and (v) a poly(A) sequence of 60 to 250 adenosine nucleotides, wherein the mRNA molecule is formulated with a cationic component and wherein the immune response stimulated by the pharmaceutical composition produces an increased amount of RSV neutralizing antibodies compared to a composition comprising a mRNA encoding a full length RSV-F.

22. The method of claim 21, wherein the pharmaceutical composition is administered by intradermal or intramuscular injection.

23. The method of claim 22, wherein the pharmaceutical composition is administered by intramuscular injection.

24. The method of claim 22, wherein the mRNA molecule is formulated with a cationic lipid.

25. The method of claim 22, wherein the 5' cap structure is m7GpppN.

26. The method of claim 22, wherein the 5' structure is a Cap1 structure.

27. The method of claim 22, wherein the poly(A) sequence is at the 3' end of the mRNA molecule.

28. The method of claim 22, wherein the 3' UTR comprises a stabilizing sequence from the alpha globin 3' UTR.

29. The method of claim 22, wherein the composition comprises at least a second, different, mRNA encoding an antigen from a different virus or an antigenic fragment thereof.

30. The method of claim 22, wherein the encoded RSV-F comprises the transmembrane domain of native RSV-F.

* * * * *

                            SEQUENCE LISTING

Sequence total quantity: 37
SEQ ID NO: 1            moltype = AA  length = 574
FEATURE                 Location/Qualifiers
source                  1..574
                        mol_type = protein
                        organism = Human orthopneumovirus
SEQUENCE: 1
MELPILKANA ITTILAAVTF CFASSQNITE EFYQSTCSAV SKGYLSALRT GWYTSVITIE   60
LSNIKENKCN GTDAKVKLIN QELDKYKNAV TELQLLMQST TAANNRARRE LPRFMNYTLN  120
NTKKTNVTLS KKRKRRFLGF LLGVGSAIAS GIAVSKVLHL EGEVNKIKSA LLSTNKAVVS  180
LSNGVSVLTS KVLDLKNYID KQLLPIVNKQ SCRISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCYGKT  420
KCTASNKNRG IIKTFSNGCD YVSNKGVDTV SVGNTLYYVN KQEGKSLYVK GEPIINFYDP  480
LVFPSDEFDA SISQVNEKIN QSLAFIRKSD ELLHHVNAGK STTNIMITTI IIVIIVILLS  540
LIAVGLLLYC KARSTPVTLS KDQLSGINNI AFSN                             574

SEQ ID NO: 2            moltype = AA  length = 298
FEATURE                 Location/Qualifiers
source                  1..298
                        mol_type = protein
                        organism = Human orthopneumovirus
SEQUENCE: 2
MSKNKDQRTA KTLEKTWDTL NHLLFISSGL YKLNLKSIAQ ITLSILAMII STSLIITAII   60
FIASANHKVT LTTAIIQDAT SQIKNTTPTY LTQDPQLGIS FSNLSEITSQ TTTILASTTP  120
GVKSNLQPTT VKTKNTTTTQ TQPSKPTTKQ RQNKPPNKPN NDFHFEVFNF VPCSICSNNP  180
TCWAICKRIP NKKPGKKTTT KPTKKPTFKT TKKDLKPQTT KPKEVPTTKP TEEPTINTTK  240
TNITTTLLTN NTTGNPKLTS QMETFHSTSS EGNLSPSQVS TTSEHPSQPS SPPNTTRQ   298

SEQ ID NO: 3            moltype = AA  length = 64
FEATURE                 Location/Qualifiers
source                  1..64
                        mol_type = protein
                        organism = Human orthopneumovirus
SEQUENCE: 3
MENTSITIEF SSKFWPYFTL IHMITTIISL LIIISIMTAI LNKLCEYNVF HNKTFELPRA   60
RVNT                                                               64

SEQ ID NO: 4            moltype = AA  length = 256
FEATURE                 Location/Qualifiers
source                  1..256
                        mol_type = protein
                        organism = Human orthopneumovirus
SEQUENCE: 4
METYVNKLHE GSTYTAAVQY NVLEKDDDPA SLTIWVPMFQ SSMPADLLIK ELANVNILVK   60
QISTPKGPSL RVMINSRSAL LAQMPSKFTI CANVSLDERS KLAYDVTTPC EIKACSLTCL  120
KSKNMLTTVK DLTMKTLNPT HDIIALCEFE NIVTSKKVII PTYLRSISVR NKDLNTLENI  180
TTTEFKNAIT NAKIIPYSGL LLVITVTDNK GAFKYIKPQS QFIVDLGAYL EKESIYYVTT  240
NWKHTATRFA IKPMED                                                 256

SEQ ID NO: 5            moltype = AA  length = 391
FEATURE                 Location/Qualifiers
source                  1..391
                        mol_type = protein
                        organism = Human orthopneumovirus
SEQUENCE: 5
MALSKVKLND TLNKDQLLSS SKYTIQRSTG DSIDTPNYDV QKHINKLCGM LLITEDANHK   60
FTGLIGMLYA MSRLGREDTI KILRDAGYHV KANGVDVTTH RQDINGKEMK FEVLTLASLT  120
TEIQINIEIE SRKSYKKMLK EMGEVAPEYR HDSPDCGMII LCIAALVITK LAAGDRSGLT  180
AVIRRANNVL KNEMKRYKGL LPKDIANSFY EVFEKHPHFI DVFVHFGIAQ SSTRGGSRVE  240
GIFAGLFMNA YGAGQVMLRW GVLAKSVKNI MLGHASVQAE MEQVVEVYEY AQKLGGEAGF  300
YHILNNPKAS LLSLTQFPHF SSVVLGNAAG LGIMGEYRGT PRNQDLYDAA KAYAEQLKEN  360
GVINYSVLDL TAEELEAIKH QLNPKDNDVE L                                391

SEQ ID NO: 6            moltype = AA  length = 2165
FEATURE                 Location/Qualifiers
source                  1..2165
                        mol_type = protein
                        organism = Human orthopneumovirus
SEQUENCE: 6
```

```
MDPIINGNSA NVYLTDSYLK GVISFSECNA LGSYIFNGPY LKNDYTNLIS RQNPLIEHMN    60
LKKLNITQSL ISKYHKGEIK LEEPTYFQSL LMTYKSMTSL EQIATTNLLK KIIRRAIEIS   120
DVKVYAILNK LGLKEKDKIK SNNGQDEDNS VITTIIKDDI LSAVKDNQSH LKADKNHSTK   180
QKDTIKTTLL KKLMCSMQHP PSWLIHWFNL YTKLNNILTQ YRSNEVKNHG FILIDNQTLS   240
GPQFILNQYG CIVYHKELKR ITVTTYNQFL TWKDISLSRL NVCLITWISN CLNTLNKSLG   300
LRCGFNNVIL TQLFLYGDCI LKLFHNEGFY IIKEVEGFIM SLILNITEED QFRKRFYNSM   360
LNNITDAANK AQKNLLSRVC HTLLDKTVSD NIINGRWIIL LSKFLKLIKL AGDNNLNNLS   420
ELYFLFRIFG HPMVDERQAM DAVKVNCNET KFYLLSSLSM LRGAFIYRII KGFVNNYNRW   480
PTLRNAIVLP LRWLTYYKLN TYPSLLELTE RDLIVLSGLR FYREFRLPKK VDLEMIINDK   540
AISPPKNLIW TSFPRNYMPS HIQNYIEHEK LKFSESDKSR RVLEYYLRDN KFNECDLYNC   600
VVNQSYLNNP NHVVSLTGKE RELSVGRMFA MQPGMFRQVQ ILAEKMIAEN ILQFFPESLT   660
RYGDLELQKI LELKAGISNK SNRYNDNYNN YISKCSIITD LSKFNQAFRY ETSCICSDVL   720
DELHGVQSLF SWLHLTIPHV TIICTYRHAP PYIRDHIVDL NNVDEQSGLY RYHMGGIEGW   780
CQKLWTIEAI SLLDLISLKG KFSITALING DNQSIDISKP VRLMEGQTHA QADYLLALNS   840
LKLLYKEYAG IGHKLKGTET YISRDMQFMS KTIQHNGVYY PASIKKVLRV GPWINTILDD   900
FKVSLESIGS LTQELEYRGE SLLCSLIFRN VWLYNQIALQ LKNHALCNNK LYLDILKVLK   960
HLKTFFNLDN IDTALTLYMN LPMLFGGGDP NLLYRSFYRR TPDFLTEAIV HSVFILSYYT  1020
NHDLKDKLQD LSDDRLNKFL TCIITFDKNP NAEFVTLMRD PQALGSERQA KITSEINRLA  1080
VTEVLSTAPN KIFSKSAQHY TTTEIDLNDI MQNIEPTYPH GLRVVYESLP FYKAEKIVNL  1140
ISGTKSITNI LEKTSAIDLT DIDRATEMMR KNITLLIRIL PLDCNRDKRE ILSMENLSIT  1200
ELSKYVRERS WSLSNIVGVT SPSIMYTMDI KYTTSTIASG IIIEKYNVNS LTRGERGPTK  1260
PWVGSSTQEK KTMPVYNRQV LTKKQRDQID LLAKLDWVYA SIDNKDEFME ELSIGTLGLT  1320
YEKAKKLFPQ YLSVNYLHRL TVSSRPCEFP ASIPAYRTTN YHFDTSPINR ILTEKYGDED  1380
IDIVFQNCIS FGLSLMSVVE QFTNVCPNRI ILIPKLNEIH LMKPPIFTGD VDIHKLKQVI  1440
QKQHMFLPDK ISLTQYVELF LSNKTLKSGS HVNSNLILAH KISDYFHNTY ILSTNLAGHW  1500
ILIIQLMKDS KGIFEKDWGE GYITDHMFIN LKVFFNAYKT YLLCFHKGYG KAKLECDMNT  1560
SDLLCVLELI DSSYWKSMSK VFLEQKVIKY ILSQDASLHR VKGCHSFKLW FLKRLNVAEF  1620
TVCPWVVNID YHPTHMKAIL TYIDLVRMGL INIDRIHIKN KHKFNDEFYT SNLFYINYNF  1680
SDNTHLLTKH IRIANSELEN NYNKLYHPTP ETLENILANP IKSNDKKTLN DYCIGKNVDS  1740
IMLPLLSNKK LVKSSAMIRT NYSKQDLYNL FPTVVIDRII DHSGNTAKSN QLYTTTSHQI  1800
SLVHNSTSLY CMLPWHHINR FNFVFSSTGC KISIEYILKD LKIKDPNCIA FIGEGAGNLL  1860
LRTVVELHPD IRYIYRSLKD CNDHSLPIEF LRLYNGHINI DYGENLTIPA TDATNNIHWS  1920
YLHIKFAEPI SLFVCDAELP VTVNWSKIII EWSKHVRKCK YCSSVNKCTL IVKYHAQDDI  1980
DFKLDNITIL KTYVCLGSKL KGSEVYLVLT IGPANIPVF NVVQNAKLIL SRTKNFIMPK  2040
KADKESIDAN IKSLIPFLCY PITKKGINTA LSKLKSVVSG DILSYSIAGR NEVFSNKLIN  2100
HKHMNILKWF NHVLNFRSTE LNYNHLYMVE STYPYLSELL NSLTTNELKK LIKITGSLLY  2160
NFHNE                                                             2165

SEQ ID NO: 7           moltype = AA   length = 194
FEATURE                Location/Qualifiers
source                 1..194
                       mol_type = protein
                       organism = Human orthopneumovirus
SEQUENCE: 7
MSRRNPCKFE IRGHCLNGKR CHFSHNYFEW PPHALLVRQN FMLNRILKSM DKSIDTLSEI    60
SGAAELDRTE EYALGVVGVL ESYIGSINNI TKQSACVAMS KLLTELNSDD IKKLRDNEEL   120
NSPKIRVYNT VISYIESNRK NNKQTIHLLK RLPADVLKKT IKNTLDIHKS ITINNPKELT   180
VSDTNDHAKN NDTT                                                    194

SEQ ID NO: 8           moltype = AA   length = 90
FEATURE                Location/Qualifiers
source                 1..90
                       mol_type = protein
                       organism = Human orthopneumovirus
SEQUENCE: 8
MTMPKIMILP DKYPCSITSI LITSRCRVTM YNRKNTLYFN QNNPNNHMYS PNQTFNEIHW    60
TSQDLIDTIQ NFLQHLGVIE DIYTIYILVS                                    90

SEQ ID NO: 9           moltype = AA   length = 241
FEATURE                Location/Qualifiers
source                 1..241
                       mol_type = protein
                       organism = Human orthopneumovirus
SEQUENCE: 9
MEKFAPEFHG EDANNRATKF LESIKGKFTS PKDPKKKDSI ISVNSIDIEV TKESPITSNS    60
TIINPTNETD DNAGNKPNYQ RKPLVSFKED PIPSDNPFSK LYKETIETFD NNEEESSYSY   120
EEINDQTNDN ITARLDRIDE KLSEILGMLH TLVVASAGPT SARDGIRDAM VGLREEMIEK   180
IRTEALMTND RLEAMARLRN EESEKMAKDT SDEVSLNPTS EKLNNLLEGN DSDNDLSLED   240
F                                                                  241

SEQ ID NO: 10          moltype = AA   length = 139
FEATURE                Location/Qualifiers
source                 1..139
                       mol_type = protein
                       organism = Human orthopneumovirus
SEQUENCE: 10
MGSNSLSMIK VRLQNLFDND EVALLKITCY TDKLIHLTNA LAKAVIHTIK LNGIVFVHVI    60
TSSDICPNNN IVVKSNFTTM PVLQNGGYIW EMMELTHCSQ PNGLIDDNCE IKFSKKLSDS   120
TMTNYMNQLS ELLGFDLNP                                               139
```

```
SEQ ID NO: 11          moltype = AA  length = 124
FEATURE                Location/Qualifiers
source                 1..124
                       mol_type = protein
                       organism = Human orthopneumovirus
SEQUENCE: 11
MDTTHNDTTP QRLMITDMRP LSLETTITSL TRDIITHRFI YLINHECIVR KLDERQATFT  60
FLVNYEMKLL HKVGSTKYKK YTEYNTKYGT FPMPIFINHD GFLECIGIKP TKHTPIIYKY  120
DLNP                                                              124

SEQ ID NO: 12          moltype = RNA  length = 1725
FEATURE                Location/Qualifiers
source                 1..1725
                       mol_type = genomic RNA
                       organism = Human orthopneumovirus
SEQUENCE: 12
atggagttgc caatcctcaa agcaaatgca attaccacaa tcctcgctgc agtcacattt  60
tgctttgctt ctagtcaaaa catcactgaa gaattttatc aatcaacatg cagtgcagtt  120
agcaaaggct atcttagtgc tctaagaact ggttggtata ctagtgttat aactatagaa  180
ttaagtaata tcaaggaaaa taagtgtaat ggaacagatg ctaaggtaaa attgataaac  240
caagaattag ataaatataa aaatgctgta acagaattgc agttgctcat gcaaagcaca  300
acagcagcaa acaatcgagc cagaagagaa ctaccaaggt ttatgaatta tacactcaac  360
aataccaaaa aaaccaatgt aacattaagc aagaaaagga aaagaagatt tcttggtttt  420
ttgttaggtg ttggatctgc aatcgccagt ggcattgctg tatctaaggt cctgcactta  480
gaaggagaag tgaacaagat caaaagtgct ctactatcca caaacaaggc cgtagtcagc  540
ttatcaaatg gagttagtgt cttaaccagc aaagtgttag acctcaaaaa ctatatagat  600
aaacaattgt tacctattgt gaataagcaa agctgcagaa tatcaaatat agaaactgtg  660
atagagttcc aacaaaagaa caacagacta ctagagatta ccagggaatt tagtgttaat  720
gcaggtgtaa ctacacctgt aagcacttac atgttaacta atagtgaatt attgtcatta  780
atcaatgata tgcctataac aaatgatcag aaaaagttaa tgtccaacaa tgttcaaata  840
gttagacagc aaagttactc tatcatgtcc ataataaaag aggaagtctt agcatatgta  900
gtacaattac cactatatgg tgtgatagat acaccttgtt ggaaattaca cacatcccct  960
ctatgtacaa ccaacacaaa agaagggtca aacatctgtt taacaagaac tgacagagga  1020
tggtactgtg acaatgcagg atcagtatct ttcttcccac aagctgaaac atgtaaagtt  1080
caatcgaatc gagtattttg tgacacaatg aacagtttaa cattaccaag tgaagtaaat  1140
ctctgcaatg ttgacatatt caatcccaaa tatgattgta aaattatgac ttcaaaaaca  1200
gatgtaagca gctccgttat cacatctcta ggagccattg tgtcatgcta tggcaaaact  1260
aaatgtacag catccaataa aaatcgtgga atcataaaga cattttctaa cgggtgtgat  1320
tatgtatcaa ataaaggggt ggacactgtg tctgtaggta acacattata ttatgtaaat  1380
aagcaagaag gcaaaagtct ctatgtaaaa ggtgaaccaa taataaattt ctatgaccca  1440
ttagtattcc cctctgatga atttgatgca tcaatatctc aagtcaatga gaagattaac  1500
cagagtttag catttattcg taaatccgat gaattattac atcatgtaaa tgctggtaaa  1560
tcaaccacaa atatcatgat aactactata attatagtga ttatagtaat attgttatca  1620
ttaattgctg ttggactgct cctatactgt aaggccagaa gcacaccagt cacactaagc  1680
aaggatcaac tgagtggtat aaataatatt gcatttagta actga                 1725

SEQ ID NO: 13          moltype = RNA  length = 897
FEATURE                Location/Qualifiers
source                 1..897
                       mol_type = genomic RNA
                       organism = Human orthopneumovirus
SEQUENCE: 13
atgtccaaaa acaaggacca acgcaccgct aagacactag aaaagacctg ggacactctc  60
aatcatttat tattcatatc atcgggctta tataagttaa atcttaaatc tatagcacaa  120
atcacattat ccattctggc aatgataatc tcaacttcac ttataattac agccatcata  180
ttcatagcct cggcaaacca caaagtcaca ctaacaactg caatcataca agatgcaaca  240
agccagatca agaacacaac cccaacatac ctcactcagg atcctcagct tggaatcagc  300
ttctccaatc tgtctgaaat tacatcacaa accaccacca tactagcttc aacaacacca  360
ggagtcaagt caaacctgca acccacaaca gtcaagacta aaaacacaac aacaacccaa  420
acacaaccca gcaagcccac tacaaaacaa cgccaaaaca aaccaccaaa caaacccaat  480
aatgattttc acttcgaagt gtttaacttt gtaccctgca gcatatgcag caacaatcca  540
acctgctggg ctatctgcaa aagaatacca aacaaaaaac caggaaagaa aaccaccacc  600
aagcctacaa aaaaaccaac cttcaagaca accaaaaaag atctcaaacc tcaaaccact  660
aaaccaaagg aagtacccac caccaagccc acagaagagc caaccatcaa caccaccaaa  720
acaaacatca caactacact gctcaccaac aacaccacag gaaatccaaa actcacaagt  780
caaatggaaa ccttccactc aacctcctcc gaaggcaatc taagcccttc tcaagtctcc  840
acaacatccg agcacccatc acaaccctca tctccaccca acacaacacg ccagtag     897

SEQ ID NO: 14          moltype = RNA  length = 195
FEATURE                Location/Qualifiers
source                 1..195
                       mol_type = genomic RNA
                       organism = Human orthopneumovirus
SEQUENCE: 14
atggaaaata catccataac aatagaattc tcaagcaaat tctggcctta ctttacacta  60
atacacatga tcacaacaat aatctctttg ctaatcataa tctccatcat gactgcaata  120
ctaaacaaac tttgtgaata taacgtattc cataacaaaa cctttgagtt accaagagct  180
cgagtcaaca catag                                                  195
```

-continued

```
SEQ ID NO: 15          moltype = RNA  length = 771
FEATURE                Location/Qualifiers
source                 1..771
                       mol_type = genomic RNA
                       organism = Human orthopneumovirus
SEQUENCE: 15
atggaaacat acgtgaacaa gcttcacgaa ggctccacat acacagctgc tgttcaatac  60
aatgtcctag aaaaagacga tgaccctgca tcacttacaa tatgggtgcc catgttccaa  120
tcatctatgc cagcagattt acttataaaa gaactagcta atgtcaacat actagtgaaa  180
caaatatcca cacccaaggg accttcacta agagtcatga taaactcaag aagtgcattg  240
ctagcacaaa tgcccagcaa atttaccata tgtgctaatg tgtccttgga tgaaagaagc  300
aaactggcat atgatgtaac cacaccctgt gaaatcaagg catgtagtct aacatgccta  360
aaatcaaaaa atatgttaac tacagttaaa gatctcacta tgaagacact caaccccaca  420
catgatatta ttgctttatg tgaatttgaa aacatagtaa catcaaaaaa agtcataata  480
ccaacatacc taagatccat cagtgtcaga aataaagatc tgaacacact tgaaaatata  540
acaaccactg aattcaaaaa tgccatcaca aatgcaaaaa tcatccctta ctcaggatta  600
ctattagtca tcacagtgac tgacaacaaa ggagcattca aatacataaa gccgcaaagt  660
caattcatag tagatcttgg agcttaccta gaaaaagaaa gtatatatta tgttaccaca  720
aattggaagc acacagctac acgatttgca atcaaaccca tggaagatta a           771

SEQ ID NO: 16          moltype = RNA  length = 1176
FEATURE                Location/Qualifiers
source                 1..1176
                       mol_type = genomic RNA
                       organism = Human orthopneumovirus
SEQUENCE: 16
atggctctta gcaaagtcaa gttgaatgat acactcaaca aagatcaact tctgtcatct  60
agcaaataca ccatccaacg gagcacagga gatagtattg atactcctaa ttatgatgtg  120
cagaaacaca tcaataagtt atgtggcatg ttattaatca cagaagatgc taatcataaa  180
ttcactgggt taataggtat gttatatgct atgtctaggt taggaagaga agacaccata  240
aaaatactca gagatgcggg atatcatgta aaagcaaatg gagtagatgt aacaacacat  300
cgtcaagaca tcaatgggaa agaaatgaaa tttgaagtgt taacattggc aagcttaaca  360
actgaaattc aaatcaacat tgagatagaa tctagaaaat cctacaaaaa aatgctaaaa  420
gaaatgggag aggtagctcc agaatacagg catgattctc ctgattgtgg gatgataata  480
ttatgtatag cagcattagt aataaccaaa ttggcagcag gggatagatc tggtcttaca  540
gccgtgatta ggagagctaa taatgtccta aaaaatgaaa tgaaacgtta caaaggctta  600
ctacccaagg atatagccaa cagcttctat gaagtgtttg aaaaacatcc ccactttata  660
gatgtttttg ttcattttgg tatagcacaa tcttccacca gaggtggcag tagagttgaa  720
gggatttttg caggattgtt tatgaatgcc tatggtgcag ggcaagtaat gctacggtgg  780
ggagtcttag caaaatcagt taaaaatatt atgttaggac atgctagtgt gcaagcagaa  840
atggaacaag ttgttgaggt ttatgaatat gcccaaaaat tgggtggaga agcaggattc  900
taccatatat tgaacaaccc aaaagcatca ttattatctt tgactcaatt tcctcacttt  960
tccagtgtag tattaggcaa tgctgctggc ctaggcataa tgggagagta cagaggtaca  1020
ccgaggaatc aagatctata tgatgcagca aaggcatatg ctgaacaact caaagaaaat  1080
ggtgtgatta actacagtgt attagacttg acagcagaag aactagaggc tatcaaacat  1140
cagcttaatc caaaagataa tgatgtagag ctttga                            1176

SEQ ID NO: 17          moltype = RNA  length = 6498
FEATURE                Location/Qualifiers
source                 1..6498
                       mol_type = genomic RNA
                       organism = Human orthopneumovirus
SEQUENCE: 17
atggatccca ttattaatgg aaattctgct aatgtttatc taaccgatag ttatttaaaa  60
ggtgttatct ctttctcaga gtgtaatgct ttaggaagtt acatattcaa tggtccttat  120
ctcaaaaatg attataccaa cttaattagt agacaaaatc cattaataga acacatgaat  180
ctaaagaaac taaatataac acagtcctta atatctaagt atcataaagg tgaaataaaa  240
ttagaagagc ctacttattt tcagtcatta cttatgacat acaagagtat gacctcgttg  300
gaacagattg ctaccactaa tttacttaaa aagataataa gaagagctat agaaataagt  360
gatgtcaaag tctatgctat attgaataaa ctagggctta aagaaaagga caagattaaa  420
tccaacaatg gacaggatga agacaactca gttattacga ccataatcaa agatgatata  480
ctttcagctg ttaaggataa tcaatctcat cttaaagcag acaaaaatca ctctacaaaa  540
caaaaagaca caatcaaaac aacactcttg aagaaattaa tgtgttcaat gcagcatcct  600
ccatcatggt taatacattg gtttaattta tacacaaaat taaacaacat attaacacag  660
tatcgatcaa atgaggttaa aaaccatggg tttatattga tagataatca aactcttagt  720
ggatttcaat ttattttgaa tcaatatggt tgtatagttt atcataagga actcaaaaga  780
attactgtga caacctataa tcaattcttg acatggaaag atattagcct tagtagatta  840
aatgtttgtt taattacatg gattagtaac tgcttgaaca cattaaataa aagcttaggc  900
ttaagatgcg gattcaataa tgttatcttg acacaactat tcctttatgg tgattgtata  960
ctaaagctat ttcacaatga ggggttctac ataataaaag aggtagaggg atttattatg  1020
tctctaattt taaatataac agaagaagat caattcagaa aacgatttta taatagtatg  1080
ctcaacaaca tcacagatgc tgctaataaa gctcagaaaa atctgctatc aagagtatgt  1140
catacattat tagataagac agtatccgat aatataataa atggcagatg gataattcta  1200
ttaagtaagt tccttaaatt aattaagctt gcaggtgaca ataaccttaa caatctgagt  1260
gaactatatt ttttgttcag aatatttgga cacccaatgg tagatgaaag acaagccatg  1320
gatgctgtta aagttaattg caatgagacc aaattttact tgttaagcag tttgagtatg  1380
ttaagaggtg cctttatata tagaattata aaagggtttg taaataatta caacagatgg  1440
cctactttaa gaaatgctat tgttttaccc ttaagatggt taacttacta taaactaaac  1500
```

```
acttatcctt ctttgttgga acttacagaa agagatttga ttgtgttatc aggactacgt   1560
ttctatcgtg agtttcggtt gcctaaaaaa gtggatcttg aaatgattat aaatgataaa   1620
gctatatcac cccctaaaaa tttgatatgg actagtttcc ctagaaatta tatgccgtca   1680
cacatacaaa actatataga acatgaaaaa ttaaaatttt ccgagagtga taaatcaaga   1740
agagtattag agtattattt aagagataac aaattcaatg aatgtgattt atacaactgt   1800
gtagttaatc aaagttatct caacaaccct aatcatgtgg tatcattgac aggcaaagaa   1860
agagaactca gtgtaggtag aatgtttgca atgcaaccgg gaatgttcag acaggttcaa   1920
atattggcag agaaaatgat agctgaaaac attttacaat tctttcctga aagtcttaca   1980
agatatggtg atctagaact acaaaaaata ttagaattga aagcaggaat aagtaacaaa   2040
tcaaatcgct acaatgataa ttacaacaat tacattagta agtgctctat catcacagat   2100
ctcagcaaat tcaatcaagc atttcgatat gaaacgtcat gtatttgtag tgatgtgctg   2160
gatgaactgc atggtgtaca atctctattt tcctggttac atttaactat tcctcatgtc   2220
acaataatat gcacatatag gcatgcaccc cctatataa gagatcatat tgtagatctt   2280
aacaatgtag atgaacaaag tggattatat agatatcaca aattaaaagg tgaagggtgg   2340
tgtcaaaaac tatggaccat agaagctata tcactattgg atctaatatc tctcaaaggg   2400
aaattctcaa ttactgcttt aattaatggt gacaatcaat caatagatat aagcaaacca   2460
gtcagactca tggaaggtca aactcatgct caagcagatt atttgctagc attaaatagc   2520
cttaaattac tgtataaaga gtatgcaggc ataggtcaca aattaaaagg aactgagact   2580
tatatatcac gagatatgca atttatgagt aaaacaattc aacataacgg tgtatattac   2640
cctgctagta taaagaaagt cctaagagtg ggaccgtgga taaacactat acttgatgat   2700
ttcaaagtga gtctagaatc tataggtagt ttgacacaag aattagaata tagaggtgaa   2760
agtctattat gcagtttaat atttagaaat gtatggtaat ataatcaaat tgctctacaa   2820
ttaaaaaatc atgcgttatg taacaataaa ttatatttgg acatattaaa ggttctgaaa   2880
cacttaaaaa cctttttaa tcttgataat attgatacag cattaacatt gtatatgaat   2940
ttacccatgt tatttggtgg tggtgatccc aacttgttat atcgaagttt ctatagaaga   3000
actcctgatt tcctcacaga ggctatagtt cactctgtgt tcatacttag ttattataca   3060
aaccatgact aaaagataaa acttcaagat ttgtcagatg atagattgaa taagttctta   3120
acatgcataa tcacgtttga caaaaaccct aatgctgaat tcgtaacatt gatgagagat   3180
cctcaagctt tagggtctga gagacaagct aaaattacta gtgaaatcaa tagactggca   3240
gttacaggg ttttgagtac agctccaaac aaaatattcc ccaaaagtgc acaacattat   3300
accactacag agatagatct aaatgatatt atgcaaaaata tagaacctac atatcctcac   3360
gggctaagag ttgtttatga agtttaccc ttttataaag cagagaaaat agtaaatctt   3420
atatcaggta caaaatctat aactaacata ctggaaaaga cttctgccat agacttaaca   3480
gatattgata gagccactga gatgatgagg aaaaacataa ctttgcttat aaggatactt   3540
ccattggatt gtaacagaga taaaagagaa atattgagta tggaaaacct aagtattact   3600
gaattaagca aatatgttag ggaaagatct tggtctttat ccaatatagt tggtgttaca   3660
tcacccagta tcatgtatac aatggacatc aaatatacaa caagcactat agctagtggc   3720
ataattatag agaaatataa tgttaacagt ttaacacgtg gtgagagagg accaactaaa   3780
ccatgggttg gttcatctac acaagagaaa aaaacaatgc cagtttataa tagacaagtt   3840
ttaaccaaaa aacaaagaga tcaaatagat ctattagcaa aattggattg ggtgtatgca   3900
tctatagata acaaggatga attcatgaaa gaactcagca taggaccct tgggttaaca   3960
tatgaaaagg ccaaaaaatt atttccacaa tatttaagtg tcaactattt gcatcgcctt   4020
acagtcagta gtagaccatg tgaattccct gcatcaaatac cagcttatag gcaacaacaaat   4080
tatcactttg acactagccc tattaatcgc atattaacag aaaagtatgg tgatgaagat   4140
attgacatag tattccaaaa ctgtataagc tttggcctta gcttaatgtc agtagtagaa   4200
caatttacta atgtatgtcc taacagaatt attctctac ctaagcttaa tgagatacat   4260
ttgatgaaac ctcccatatt cacaggtgat gttgatatcc acaagttaaa acaagtgata   4320
caaaacagc atatgttttt accagacaaa ataagtttga ctcaatatgt ggaattattc   4380
ttaagtaaca aaacactcaa atctggatct catgttaatt ctaatttaat attggcacat   4440
aaaatatctg actatttca taatacttac attttaagta ctaatttagc tggacattgg   4500
attctaatta tacaacttat gaaagattcc aaaggtattt ttgaaaaaga ttggggagag   4560
ggatatataa ctgatcatat gtttattaat ttgaaagttt tcttcaatgc ttataagacc   4620
tatctcttgt gttttcataa aggttatggc aaagcaaaac tggagtgtga tatgaacact   4680
tcagatcttc tatgtgtatt ggaattaata gacagtagtt attggaagtc tatgtctaag   4740
gtattttag aacaaaaagt tatcaaatac attcttagcc aagtgcaag tttacataga   4800
gtaaaaggat gtcatagctt caaattatgg tttcttaaac gtcttaatgt agcagaattc   4860
acagtttgcc cttgggttgt taacatagat tatcatccaa cacatatgaa agcaatatta   4920
acttatatag atcttgttag aatgggattg ataaatatag agaatacaca cattaaaaat   4980
aaacacaaat tcaatgatga atttatact tctaatctct tttacattaa ttataacttc   5040
tcagataata ctcatctatt aactaaacat ataaggattg ctaattcaga attgaaaat   5100
aattacaaca aattatatca tcctacacca gaaaccctag agaatatact agccaatccg   5160
attaaaagta atgacaaaaa gacactgaac gactattgta taggtaaaaa tgttgactca   5220
ataatgttac cattgttatc taataagaag cttgttaaat cgtctgcaat gattagaacc   5280
aattacagca aacaagacct gtacaatcta ttccctaccg ttgtgatcga tagaattata   5340
gatcattcag gtaatacagc caaatccaac caacttacca ctactactc ccatcaaata   5400
tctttagtgc acaatagcac atcactttat tgcatgcttc cttggcatca tattaataga   5460
ttcaattttg tatttagttc tacaggttgt aaaattagta tagagtatat tttaaaagac   5520
cttaaaatta aagatcctaa ttgtatagca ttcataggtg aaggagcagg gaatttatta   5580
ttgcgtacag tggtggaact tcatcctgac ataagatata tttacagag tctgaaagat   5640
tgcaatgatc atagtttacc tattgagttt ttaaggctat acaatggaca tatcaacatt   5700
gattatggtg aaaatttgac cattcctgct acagatgcaa ccaacaacat tcattggtct   5760
tatttacata taaagtttgc tgaacctatc agtcttttg tatgtgatgc cgaattgcct   5820
gtaacagtca actggagtaa aattataata gaatgggca agcatgtaag aaaatgcaag   5880
tactgttcct cagttaataa gtgtacgtta atgtgcgctca agatgatatt   5940
gatttcaaat tagacaatat aactatatta aaaacttatg tatgcttagg cagtaagtta   6000
aagggatcgg aggtttactt agtccttaca ataggtcctg caaatatatt tccagtttt   6060
aatgtagtac aaaatgctaa attgatacta tcaagaacca aaaatttcat catgcctaag   6120
aaagctgata aagagtctat tgatgcaaat attaaaagtt tgataccctt tctttgttac   6180
cctataacaa aaaaaggaat taatactgca ttgtcaaaac taaagagtgt tgttagtgga   6240
```

```
gatatactat catattctat agctggacgg aatgaagttt tcagcaataa acttataaat 6300
cataagcata tgaacatctt aaagtggttc aatcatgttt taaatttcag atcaacagaa 6360
ctaaactata accatttata tatggtagaa tctacatatc cttacctaag tgaattgtta 6420
aacagcttga caactaatga acttaaaaaa ctgattaaaa tcacaggtag tctgttatac 6480
aactttcata atgaataa                                                6498

SEQ ID NO: 18          moltype = RNA   length = 585
FEATURE                Location/Qualifiers
source                 1..585
                       mol_type = genomic RNA
                       organism = Human orthopneumovirus
SEQUENCE: 18
atgtcacgaa ggaatccttg caaatttgaa attcgaggtc attgcttgaa tggtaagaga 60
tgtcattta gtcataatta ttttgaatgg ccaccccatg cactgctcgt aagacaaaac 120
tttatgttaa acagaatact taagtctatg gataaaagta tagataccct atcagaaata 180
agtggagctg cagagttgga cagaacagaa gagtatgctc ttggtgtagt tggagtgcta 240
gagagttata taggatcaat aaataatata actaaacaat cagcatgtgt tgccatgagc 300
aaactcctca ctgaactcaa tagtgatgat atcaaaaaac tgagagacaa tgaagagcta 360
aattcaccca agataagagt gtacaatact gtcatatcat atattgaaag caacaggaaa 420
aacaataaac aaactatcca tctgttaaaa agattgccag cagacgtatt gaagaaaacc 480
atcaaaaaca cattggatat ccacaagagc ataaccatca caacccaaa gaattaact  540
gttagtgata caaatgacca tgccaaaaat aatgatacta cctga                585

SEQ ID NO: 19          moltype = RNA   length = 273
FEATURE                Location/Qualifiers
source                 1..273
                       mol_type = genomic RNA
                       organism = Human orthopneumovirus
SEQUENCE: 19
atgaccatgc caaaaataat gatactacct gacaaatatc cttgtagtat aacttccata 60
ctaataacaa gtagatgtag agtcactatg tataatcgaa agaacacact atatttcaat 120
caaaacaacc caataaacca tatgtactca ccgaatcaaa cattcaatga aatccattgg 180
acctcacaag acttgattga cacaattcaa aattttctac agcatctagg tgttattgag 240
gatatatata caatatatat attagtgtca taa                              273

SEQ ID NO: 20          moltype = RNA   length = 726
FEATURE                Location/Qualifiers
source                 1..726
                       mol_type = genomic RNA
                       organism = Human orthopneumovirus
SEQUENCE: 20
atggaaaagt ttgctcctga attccatgga gaagatgcaa caacagggc tactaaattc 60
ctagaatcaa taagggcaa attcacatca cctaaagatc caagaaaaa agatagtatc 120
atatctgtca actcaataga tatagaagta accaagaaa gccctataac atcaaattca 180
accattatta acccaacaaa tgagacagat gataatgcag gaacaagcc aattatcaa  240
agaaaacctc tagtaagttt caagaagac cctataccaa gtgataatcc cttttcaaaa 300
ctatacaaag aaaccataga gacatttgat aacaatgaag aagaatctag ctattcatat 360
gaagaaataa atgatcagac gaacgataat ataactgcaa gattagatag gattgatgaa 420
aaattaagtg aaatactagg aatgcttcac acattagtag tagcaagtgc aggacctaca 480
tctgctaggg atggtataag agatgccatg gttggtttaa gaagaaat gatagaaaaa 540
atcagaacta aagcattaat gaccaatgac agattagaag ctatggcaag actcaggag 600
gaggaaagtg aaaagatggc aaaagacaca tcagatgaag tgtctctcaa tccaacatca 660
gagaaattga acaacctgtt ggaagggaat gatagtgaca atgatctatc acttgaagat 720
ttctga                                                             726

SEQ ID NO: 21          moltype = RNA   length = 420
FEATURE                Location/Qualifiers
source                 1..420
                       mol_type = genomic RNA
                       organism = Human orthopneumovirus
SEQUENCE: 21
atgggcagca attcgttgag tatgataaaa gttagattac aaaatttgtt tgacaatgat 60
gaagtagcat tgtaaaaat aacatgctat actgacaaat taataacttt aactaatgct 120
ttggctaagg cagtgataca tacaatcaaa ttgaatggca ttgtgttttgt gcatgttatt 180
acaagtagtg atatttgccc taataataat attgtagtaa aatccaattt cacaacaatg 240
ccagtgctac aaaatggagg ttatatatgg gaaatgatgg aattaacaca ttgctctcaa 300
cctaatggtc taatagatga caattgtgaa attaaattct ccaaaaaact aagtgattca 360
acaatgacca attatatgaa tcaattatct gaattacttg gatttgatct taatcataa  420

SEQ ID NO: 22          moltype = RNA   length = 375
FEATURE                Location/Qualifiers
source                 1..375
                       mol_type = genomic RNA
                       organism = Human orthopneumovirus
SEQUENCE: 22
atggacacaa cccacaatga taccacacca caaagactga tgatcacaga catgagaccg 60
ttgtcacttg agactacaat aacatcacta accagagaca tcataacaca cagatttata 120
tacttaataa atcatgaatg catagtgaga aaacttgatg aaagacaggc cacatttaca 180
ttcctggtca actatgaaat gaaactattg cacaaagtag gaagcactaa atataaaaaa 240
```

```
tatactgaat acaacacaaa atatggcact ttccctatgc cgatattcat caatcatgat    300
gggttcttag aatgcattgg cattaagcct acaaagcata ctcccataat atacaagtat    360
gatctcaatc catag                                                     375

SEQ ID NO: 23            moltype = DNA   length = 42
FEATURE                  Location/Qualifiers
source                   1..42
                         mol_type = other DNA
                         organism = Homo sapiens
SEQUENCE: 23
ggcgctgcct acggaggtgg cagccatctc cttctcggca tc                        42

SEQ ID NO: 24            moltype = DNA   length = 186
FEATURE                  Location/Qualifiers
source                   1..186
                         mol_type = other DNA
                         organism = Homo sapiens
SEQUENCE: 24
catcacattt aaaagcatct cagcctacca tgagaataag agaaagaaaa tgaagatcaa     60
aagcttattc atctgttttt cttttcgtt ggtgtaaagc caacccctg tctaaaaaac     120
ataaatttct ttaatcattt tgcctctttt ctctgtgctt caattaataa aaatggaaa    180
gaatct                                                              186

SEQ ID NO: 25            moltype = DNA   length = 186
FEATURE                  Location/Qualifiers
source                   1..186
                         mol_type = other DNA
                         organism = Homo sapiens
SEQUENCE: 25
catcacattt aaaagcatct cagcctacca tgagaataag agaaagaaaa tgaagatcaa     60
tagcttattc atctcttttt cttttcgtt ggtgtaaagc caacccctg tctaaaaaac     120
ataaatttct ttaatcattt tgcctctttt ctctgtgctt caattaataa aaatggaaa    180
gaacct                                                              186

SEQ ID NO: 26            moltype = DNA   length = 110
FEATURE                  Location/Qualifiers
source                   1..110
                         mol_type = other DNA
                         organism = Homo sapiens
SEQUENCE: 26
gctggagcct cggtggccat gcttcttgcc ccttgggcct cccccagcc cctcctcccc     60
ttcctgcacc cgtacccccg tggtctttga ataaagtctg agtgggcggc              110

SEQ ID NO: 27            moltype = DNA   length = 108
FEATURE                  Location/Qualifiers
source                   1..108
                         mol_type = other DNA
                         organism = Homo sapiens
SEQUENCE: 27
gctggagcct cggtagccgt tcctcctgcc cgctgggcct cccaacgggc cctcctcccc     60
tccttgcacc ggcccttcct ggtctttgaa taaagtctga gtgggcag                108

SEQ ID NO: 28            moltype = DNA   length = 132
FEATURE                  Location/Qualifiers
source                   1..132
                         mol_type = other DNA
                         organism = Homo sapiens
SEQUENCE: 28
gctcgctttc ttgctgtcca atttctatta aaggttcctt tgttccctaa gtccaactac     60
taaactgggg gatattatga agggccttga gcatctggat tctgcctaat aaaaaacatt    120
tattttcatt gc                                                       132

SEQ ID NO: 29            moltype = DNA   length = 44
FEATURE                  Location/Qualifiers
misc_feature             1..44
                         note = Center, alpha-complex-binding portion of the 3'UTR
                          of an alpha-globin gene (muag)
source                   1..44
                         mol_type = other DNA
                         organism = synthetic construct
SEQUENCE: 29
gcccgatggg cctcccaacg ggccctcctc ccctccttgc accg                      44

SEQ ID NO: 30            moltype = DNA   length = 24
FEATURE                  Location/Qualifiers
misc_feature             1..24
                         note = particular preferred histone stem-loop sequence
source                   1..24
                         mol_type = other DNA
```

```
                         organism = synthetic construct
SEQUENCE: 30
caaaggctct tttcagagcc acca                                           24

SEQ ID NO: 31            moltype = RNA  length = 1942
FEATURE                  Location/Qualifiers
misc_feature             1..1942
                         note = RSV-F long (GC) R1691
source                   1..1942
                         mol_type = other RNA
                         organism = synthetic construct
SEQUENCE: 31
gggagaaagc ttaccatgga gctgcccatc ctcaaggcca acgccatcac caccatcctg  60
gcggccgtga cgttctgctt cgccagctcc cagaacatca ccgaggagtt ctaccagagc  120
acctgctccg ccgtcagcaa gggctacctg tccgccctcc ggaccgggtg gtacacgagc  180
gtgatcacca tcgagctgtc caacatcaag gagaacaagt gcaacggcac cgacgcgaag  240
gtgaagctga tcaaccagga gctcgacaag tacaagaacg ccgtcaccga gctgcagctg  300
ctcatgcaga gcacgaccgc cgccaacaac cgcgcgcggc gcgagctgcc gcggttcatg  360
aactacaccc tgaacaacac caagaagacg aacgtgaccc tctccaagaa gcgcaagcgg  420
cgcttcctgg ggttcctgct cggcgtgggg agcgccatcg cctccggcat cgccgtcagc  480
aaggtgctgc acctggaggg cgaggtgaac aagatcaagt ccgccctcct gagcaccaac  540
aaggcggtcg tgtccctgag caacggggtg tccgtcctca ccagcaaggt gctggacctg  600
aagaactaca tcgacaagca gctcctgccc atcgtgaaca agcagtcctg ccggatcagc  660
aacatcgaga cggtcatcga gttccagcag aagaacaacc gcctgctcga gatcacccgg  720
gagttcagcg tgaacgccgg cgtgaccacc cccgtctcca cgtacatgct gaccaacagc  780
gagctgctct ccctgatcaa cgacatgccc atcaccaacg accagaagaa gctgatgagc  840
aacaacgtgc agatcgtgcg ccagcagtcc tacagcatca tgtccatcat caaggaggag  900
gtcctcgcct acgtggtgca gctgccgctg tacggggtca tcgacacccc ctgctggaag  960
ctccacacga gcccccctgtg caccaccaac accaaggagg gctccaacat ctgcctgacg  1020
cggaccgacc gcgggtggta ctgcgacaac gccggcagcg tgtccttctt cccccaggcc  1080
gagacctgca aggtccagag caaccgggtg ttctgcgaca ccatgaactc cctcacgctg  1140
ccgagcgagg tgaacctgtg caacgtcgac atcttcaacc ccaagtacga ctgcaagatc  1200
atgacctcca agaccgacgt gagctccagc gtgatcacct ccctcggcgc gatcgtcagc  1260
tgctacggga agacgaagtg caccgccagc aacaagaacc gcggcatcat caagaccttc  1320
tccaacgggt gcgactacgt gagcaacaag ggcgtggaca ccgtctccgt gggcaacacc  1380
ctgtactacg tgaacaagca ggaggggaag agcctgtacg tcaagggcga gcccatcatc  1440
aacttctacg acccccctcgt gttcccgtcc gacgagttcg acgccagcat ctcccaggtg  1500
aacgagaaga tcaaccagag cctggccttc atccggaagt ccgacgagct gctgcaccac  1560
gtcaacgccg ggaagagcac gaccaacatc atgatcacca ccatcatcat cgtgatcatc  1620
gtgatcctcc tgtccctgat cgcggtcggc ctcctgctgt actgcaaggc ccgcagcacg  1680
cccgtgaccc tctccaagga ccagctgagc gggatcaaca acatcgcctt ctccaactga  1740
ggactagtta taagactgac tagcccgatg ggcctcccaa cgggccctcc tcccctcctt  1800
gcaccgagat taataaaaaa aaaaaaaaaa aaaaaaaaaa aaaaaaaaaa aaaaaaaaaa  1860
aaaaaaaaaa aaaaaaaatg catccccccc cccccccccc cccccccccc ccccaaaggc  1920
tcttttcaga gccaccagaa tt                                           1942

SEQ ID NO: 32            moltype = RNA  length = 2107
FEATURE                  Location/Qualifiers
misc_feature             1..2107
                         note = RSV-F long (GC) R2510
source                   1..2107
                         mol_type = other RNA
                         organism = synthetic construct
SEQUENCE: 32
ggggcgctgc ctacggaggt ggcagccatc tccttctcgg catcaagctt accatggagc  60
tgcccatcct caaggccaac gccatcacca ccatcctggc ggccgtgacg ttctgcttcg  120
ccagctccca gaacatcacc gaggagttct accagagcac ctgctccgcc gtcagcaagg  180
gctacctgtc cgccctccgg accgggtggt acacgagcgt gatcaccatc gagctgtcca  240
acatcaagga gaacaagtgc aacggcaccg acgcgaaggt gaagctgatc aaccaggagc  300
tcgacaagta caagaacgcc gtcaccgagc tgcagctgct catgcagagc acgaccgccg  360
ccaacaaccg cgcgcggcgc gagctgccgc ggttcatgaa ctacaccctg aacaacacca  420
agaagacgaa cgtgaccctc tccaagaagc gcaagcggcg cttcctgggg ttcctgctcg  480
gcgtggggag cgccatcgcc tccggcatcg ccgtcagcaa ggtgctgcac ctggagggcg  540
aggtgaacaa gatcaagtcc gccctcctga gcaccaacaa ggcggtcgtg tccctgagca  600
acggggtgtc cgtcctcacc agcaaggtgc tggacctgaa gaactacatc gacaagcagc  660
tcctgcccat cgtgaacaag cagtcctgcc ggatcagcaa catcgagacg gtcatcgagt  720
tccagcagaa gaacaaccgc ctgctcgaga tcacccggga gttcagcgtg aacgccggcg  780
tgaccacccc cgtctccacg tacatgctga ccaacagcga gctgctctcc ctgatcaacg  840
acatgcccat caccaacgac cagaagaagc tgatgagcaa caacgtgcag atcgtgcgcc  900
agcagtccta cagcatcatg tccatcatca aggaggaggt cctcgcctac gtggtgcagc  960
tgccgctgta cggggtcatc gacaccccct gctggaagct ccacacgagc ccccctgtgca  1020
ccaccaacac caaggagggc tccaacatct gcctgacgcg gaccgaccgc gggtggtact  1080
gcgacaacgc cggcagcgtg tccttcttcc cccaggccga gacctgcaag gtccagagca  1140
accgggtgtt ctgcgacacc atgaactccc tcacgctgcc gagcgaggtg aacctgtgca  1200
acgtcgacat cttcaacccc aagtacgact gcaagatcat gacctccaag accgacgtga  1260
gctccagcgt gatcacctcc ctcggcgcga tcgtcagctg ctacgggaag acgaagtgca  1320
ccgccagcaa caagaaccgc ggcatcatca agaccttctc caacgggtgc gactacgtga  1380
gcaacaaggg cgtggacacc gtctccgtgg gcaacaccct gtactacgtg aacaagcagg  1440
aggggaagag cctgtacgtc aagggcgagc ccatcatcaa cttctacgac cccctcgtgt  1500

-continued

```
tcccgtccga cgagttcgac gccagcatct cccaggtgaa cgagaagatc aaccagagcc  1560
tggccttcat ccggaagtcc gacgagctgc tgcaccacgt caacgccggg aagagcacga  1620
ccaacatcat gatcaccacc atcatcatcg tgatcatcgt gatcctcctg tccctgatcg  1680
cggtcggcct cctgctgtac tgcaaggccg cagcacgcc cgtgaccctc tccaaggacc  1740
agctgagcgg gatcaacaac atcgccttct ccaactgagg actagtgcat cacatttaaa  1800
agcatctcag cctaccatga gaataagaga agaaaatga agatcaatag cttattcatc  1860
tcttttttctt tttcgttggt gtaaagccaa caccctgtct aaaaaacata aatttcttta  1920
atcatttttgc ctcttttctc tgtgcttcaa ttaataaaaa atggaaagaa cctagatcta  1980
aaaaaaaaaa aaaaaaaaaa aaaaaaaaaa aaaaaaaaaa aaaaaaaaaa aaaaaaaaaa  2040
aaatgcatcc cccccccccc cccccccccc ccccccccca aaggctcttt tcagagccac  2100
cagaatt                                                             2107

SEQ ID NO: 33         moltype = RNA  length = 2044
FEATURE               Location/Qualifiers
misc_feature          1..2044
                      note = RSV-Fdel554-574 long (GC) R2821
source                1..2044
                      mol_type = other RNA
                      organism = synthetic construct
SEQUENCE: 33
ggggcgctgc ctacggaggt ggcagccatc tccttctcgg catcaagctt accatggagc  60
tgcccatcct caaggccaac gccatcacca ccatcctgcg ggccgtgacg ttctgcttcg  120
ccagctccca gaacatcacc gaggagttct accagagcac ctgctccgcc gtcagcaagg  180
gctacctgtc cgccctccgg accgggtggt acacgagcgt gatcaccatc gagctgtcca  240
acatcaagga gaacaagtgc aacggcaccg acgcgaaggt gaagctgatc aaccaggagc  300
tcgacaagta caagaacgcc gtcaccgagc tgcagctgct catgcagagc acgaccgccg  360
ccaacaaccg cgcgcggcgc gagctgccgc ggttcatgaa ctacaccctg aacaacacca  420
agaagacgaa cgtgaccctc tccaagaagc gcaagcggcg cttcctgggg ttcctgctcg  480
gcgtgggggag cgccatcgcc tccggcatcg ccgtcagcaa ggtgctgcac ctggaggcg  540
aggtgaacaa gatcaagtcc gccctcctga gcaccaacaa ggccgtcgtg tccctgagca  600
acggggtgtc cgtcctcacc agcaaggtgc tggacctgaa gaactacatc gacaagcagc  660
tcctgcccat cgtgaacaag cagtcctgcc ggatcagcaa catcgagacg gtcatcgagt  720
tccagcagaa gaacaaccgc ctgctcgaga tcacccggga gttcagcgtg aacgccggcg  780
tgaccaccccc cgtctccacg tacatgctga caacagcga gctgctcctc ctgatcaacg  840
acatgcccat caccaacgac cagaagaagc tgatgagcaa caacgtccgt gatcgtgcgc  900
agcagtccta cagcatcatg tccatcatca aggaggaggt cctcgcctac gtggtggcagc  960
tgccgctgta cggggtcatc gacaccccct gctggaagct ccacgagc cccctgtgca  1020
ccaccaacac caaggagggc tccaacatct gcctgacgcg gaccgaccgc gggtggtact  1080
gcgacaacgc cggcagcgtg tccttcttcc ccaggcgga acctgcaag gtccagagca  1140
accgggtgtt ctgcgacacc atgaactccc tcacgctgcc gagcgaggtg aacctgtgca  1200
acgtcgacat cttcaacccc aagtacgact gcaagatcat gacctccaag accgacgtga  1260
gctccagcgt gatcacctcc ctcggcgcga tcgtcagctg ctacgggaag acgaagtgca  1320
ccgccagcaa caagaaccgc ggcatcatca agacctttcc caacgggtgc gactacgtga  1380
gcaacaaggg cgtggacacc gtctccgtgg gcaacaccct gtactacgtg aacaagcagg  1440
aggggaagag cctgtacgtc aagggcgagc ccatcatcaa cttctacgac cccctcgtgt  1500
tcccgtccga cgagttcgac gccagcatct cccaggtgaa cgagaagatc aaccagagcc  1560
tggccttcat ccggaagtcc gacgagctgc tgcaccacgt caacgccggg aagagcacga  1620
ccaacatcat gatcaccacc atcatcatcg tgatcatcgt gatcctcctg tccctgatcg  1680
cggtcggcct cctgctgtac tgcaaggccg ctgaggact agtgcatcac atttaaaagc  1740
atctcagcct accatgagaa taagagaaag aaaatgaaga tcaatagctt attcatctct  1800
ttttctttttt cgttggtgta aagccaacac cctgtctaaa aaacataaat ttctttaatc  1860
attttgcctc ttttctctgt gcttcaatta ataaaaatg gaaagaacct agatctaaaa  1920
aaaaaaaaaa aaaaaaaaaa aaaaaaaaaa aaaaaaaaaa aaaaaaaaaa aaaaaaaaaa  1980
tgcatccccc cccccccccc cccccccccc ccccccaaag gctcttttca gagccaccag  2040
aatt                                                              2044

SEQ ID NO: 34         moltype = RNA  length = 1558
FEATURE               Location/Qualifiers
misc_feature          1..1558
                      note = RSV-N (GC) R2831
source                1..1558
                      mol_type = other RNA
                      organism = synthetic construct
SEQUENCE: 34
ggggcgctgc ctacggaggt ggcagccatc tccttctcgg catcaagctt accatggccc  60
tgagcaaggt gaagctcaac gacaccctga acaaggacca gctgctctcc agctccaagt  120
acaccatcca gcgcagcacg ggcgactcca tcgacacccc caactacgac gtccagaagc  180
acatcaacaa gctgtgcggg atgctgctca tcaccgagga cgccaaccac aagttcaccg  240
gcctgatcgg gatgctgtac gcgatgagcc ggctcggccg cgaggacacg atcaagatcc  300
tgcgggacgc cggtaccac gtgaaggcca acggcgtgga cgtcaccacc cacgccagg  360
acatcaacgg caaggagatg aagttcgagg tgctgaccct cgcctccctg acgaccgaga  420
tccagatcaa catcgagatc gagagccgga gtcctacaa gagatgctg aaggagtgg  480
gggaggtggc cccggagtac cgccacgaca gcccgactg cggcatgatc atcctctgca  540
tcgcgggcct ggtcatcacc aagctggccg cggggacgg gtccggcctc accgcggtga  600
tccgccgggc caacaacgtg ctgaagaacg agatgaagcg ctacaagggg ctgctccca  660
aggacatcgc caacagcttc tacgaggtct cgagaagca ccccactc atcgacgtgt  720
tcgtgcactt cggcatcgcc cagtccagca cgcggggcgg gtcccgcgtc gagggcatct  780
tcgcgggct gttcatgaac gcgtacgcg ccggccaggt gatgctgcgg tggggcgtgc  840
tcgccaagag cgtcaagaac atcatgctgg ggcacgcctc cgtgcaggcc gagatgggagc  900
```

```
aggtggtcga ggtgtacgag tacgcgcaga agctgggcgg cgaggccggg ttctaccaca    960
tcctcaacaa cccgaaggcc agcctgctgt ccctcaccca gttcccgcac ttcagcagcg   1020
tggtcctggg gaacgccgcc ggcctgggga tcatgggcga gtaccgcggg accccgcgga   1080
accaggacct ctacgacgcg gccaaggcct acgccgagca gctgaaggag aacggcgtga   1140
tcaactactc cgtgctggac ctcaccgccg aggagctgga ggcgatcaag caccagctga   1200
accccaagga caacgacgtc gagctctgag gactagtgca tcacatttaa aagcatctca   1260
gcctaccatg agaataagag aaagaaaatg aagatcaata gcttattcat ctcttttttct   1320
ttttcgttgg tgtaaagcca acaccctgtc taaaaaacat aaatttcttt aatcattttg   1380
cctcttttct ctgtgcttca attaataaaa aatggaaaga acctagatct aaaaaaaaaa   1440
aaaaaaaaaa aaaaaaaaaa aaaaaaaaaa aaaaaaaaaa aaaaaaaaaa aaatgcatc    1500
cccccccccc cccccccccc cccccccccc aaaggctctt ttcagagcca ccagaatt     1558

SEQ ID NO: 35          moltype = RNA    length = 967
FEATURE                Location/Qualifiers
misc_feature           1..967
                       note = RSV-M2-1 (GC) R2833
source                 1..967
                       mol_type = other RNA
                       organism = synthetic construct
SEQUENCE: 35
ggggcgctgc ctacggaggt ggcagccatc tccttctcgg catcaagctt accatgagcc     60
gccgaaccc ctgcaagttc gagatccgcg ccactgcct gaacgggaag cggtgccact     120
tctcccacaa ctacttcgag tggccgcccc acgccctcct ggtgcgccag aacttcatgc    180
tgaaccggat cctcaagagc atggacaagt ccatcgacac cctgagcgag atctccggcg    240
ccgcggagct ggaccgcacc gaggagtacg ccctcggggt cgtgggcgtg ctggagagct    300
acatcgggtc catcaacaac atcacgaagc agagcgcctg cgtcgccatg tccaagctgc    360
tcaccgagct gaacagcgac gacatcaaga agctgcggga caacgaggag ctcaactccc    420
ccaagatccg cgtgtacaac accgtgatca gctacatcga gtccaaccgg aagaacaaca    480
agcagaccat ccacctgctg aagcgcctcc ccgccgacgt cctgaagaag acgatcaaga    540
acaccctgga catccacaag agcatcacca tcaacaaccc gaaggagctc accgtgtccg    600
acacgaacga ccacgcgaag aacaacgaca ccacctgagg actagtgcat cacatttaaa    660
agcatctcag cctaccatga gaataagaga aagaaaatga agatcaatag cttattcatc    720
tctttttctt tttcgttggt gtaaagccaa caccctgtct aaaaaacata aatttcttta    780
atcattttgc ctcttttctc tgtgcttcaa ttaataaaaa atggaaagaa cctagatcta    840
aaaaaaaaaa aaaaaaaaaa aaaaaaaaaa aaaaaaaaaa aaaaaaaaaa aaaaaaaaaa    900
aaatgcatcc cccccccccc cccccccccc ccccccccca aaggctcttt tcagagccac    960
cagaatt                                                              967

SEQ ID NO: 36          moltype = DNA    length = 75
FEATURE                Location/Qualifiers
source                 1..75
                       mol_type = other DNA
                       organism = Homo sapiens
SEQUENCE: 36
gcggctcggc cattttgtcc cagtcagtcc ggaggctgcg gctgcagaag taccgcctgc     60
ggagtaactg caaag                                                     75

SEQ ID NO: 37          moltype = RNA    length = 24
FEATURE                Location/Qualifiers
misc_feature           1..24
                       note = histone stem-loop sequence
source                 1..24
                       mol_type = other RNA
                       organism = synthetic construct
SEQUENCE: 37
caaaggctct tttcagagcc acca                                           24
```